US010492962B2

(12) United States Patent
Greening, II et al.

(10) Patent No.: US 10,492,962 B2
(45) Date of Patent: *Dec. 3, 2019

(54) ABSORBENT ARTICLES COMPRISING SUBSTANTIALLY IDENTICAL CHASSIS AND SUBSTANTIALLY IDENTICAL FLAPS

(71) Applicant: The Procter & Gamble Company, Cincinnati, OH (US)

(72) Inventors: Nelson Edward Greening, II, Cincinnati, OH (US); Masaharu Nishikawa, Cincinnati, OH (US); Gary Dean LaVon, Liberty Township, OH (US)

(73) Assignee: The Procter & Gamble Company, Cincinnati, OH (US)

(*) Notice: Subject to any disclaimer, the term of this patent is extended or adjusted under 35 U.S.C. 154(b) by 248 days.

This patent is subject to a terminal disclaimer.

(21) Appl. No.: 15/267,785

(22) Filed: Sep. 16, 2016

(65) Prior Publication Data

US 2017/0079851 A1 Mar. 23, 2017

Related U.S. Application Data

(60) Provisional application No. 62/220,570, filed on Sep. 18, 2015.

(51) Int. Cl.
| | |
|---|---|
| *A61F 13/15* | (2006.01) |
| *A61F 13/58* | (2006.01) |
| *A61F 13/551* | (2006.01) |
| *A61F 13/56* | (2006.01) |
| A61F 13/49 | (2006.01) |
| A61F 13/493 | (2006.01) |

(52) U.S. Cl.
CPC ........ *A61F 13/58* (2013.01); *A61F 13/55105* (2013.01); *A61F 13/5633* (2013.01); *A61F 13/49* (2013.01); *A61F 13/493* (2013.01); *A61F 13/49011* (2013.01)

(58) Field of Classification Search
CPC .......... A61L 15/58; A61L 15/56; A61F 13/49; A61F 13/493; A61F 13/55105; A61F 13/49011
USPC .............. 604/385.02, 385.01, 385.29, 385.3, 604/385.24, 385.27; 206/438
See application file for complete search history.

(56) References Cited

U.S. PATENT DOCUMENTS

| | | | |
|---|---|---|---|
| 2,075,189 | A | 3/1937 | Galligan et al. |
| 3,025,199 | A | 3/1962 | Harwood |
| 3,848,594 | A | 11/1974 | Buell et al. |
| 3,860,003 | A | 1/1975 | Buell |
| 4,107,364 | A | 8/1978 | Sisson |
| 4,209,563 | A | 6/1980 | Sisson |
| 4,515,595 | A | 5/1985 | Kievit et al. |

(Continued)

FOREIGN PATENT DOCUMENTS

| | | |
|---|---|---|
| EP | 0 589 859 A1 | 3/1994 |
| EP | 1891919 | 2/2008 |

(Continued)

OTHER PUBLICATIONS

All Office Actions for U.S. Appl. No. 15/267,742.

(Continued)

*Primary Examiner* — Jacqueline F Stephens
(74) *Attorney, Agent, or Firm* — Richard L. Alexander

(57) ABSTRACT

In one embodiment, taped and pant articles of the present disclosure may comprise first and second chassis and first and second belt flaps that are at least substantially identical.

20 Claims, 21 Drawing Sheets

(56) References Cited

U.S. PATENT DOCUMENTS

| | | |
|---|---|---|
| 4,610,678 A | 9/1986 | Weisman et al. |
| 4,662,875 A | 5/1987 | Hirotsu et al. |
| 4,673,402 A | 6/1987 | Weisman et al. |
| 4,695,278 A | 9/1987 | Lawson |
| 4,704,115 A | 11/1987 | Buell |
| 4,795,454 A | 1/1989 | Dragoo |
| 4,834,735 A | 5/1989 | Alemany et al. |
| 4,834,741 A | 5/1989 | Sabee |
| 4,846,815 A | 7/1989 | Scripps |
| 4,888,231 A | 12/1989 | Angstadt |
| 4,894,060 A | 1/1990 | Nestegard |
| 4,909,803 A | 3/1990 | Aziz et al. |
| 4,940,464 A | 7/1990 | VanGompel et al. |
| 4,946,527 A | 8/1990 | Battrell |
| 5,092,861 A | 3/1992 | Nomura et al. |
| 5,151,092 A | 9/1992 | Buell et al. |
| 5,167,897 A | 12/1992 | Weber et al. |
| 5,221,274 A | 6/1993 | Buell et al. |
| 5,246,433 A | 9/1993 | Hasse et al. |
| 5,330,458 A | 7/1994 | Buell et al. |
| 5,360,420 A | 11/1994 | Cook et al. |
| 5,366,782 A | 11/1994 | Curro et al. |
| 5,518,801 A | 5/1996 | Chappell et al. |
| 5,562,646 A | 10/1996 | Goldman et al. |
| 5,569,234 A | 10/1996 | Buell et al. |
| 5,599,335 A | 2/1997 | Goldman et al. |
| 5,607,537 A | 3/1997 | Johnson et al. |
| 5,622,589 A | 4/1997 | Johnson et al. |
| 5,628,097 A | 5/1997 | Benson et al. |
| 5,643,588 A | 7/1997 | Roe et al. |
| 5,662,638 A | 9/1997 | Johnson et al. |
| 5,669,894 A | 9/1997 | Goldman et al. |
| 5,674,216 A | 10/1997 | Buell et al. |
| 5,702,551 A | 12/1997 | Huber et al. |
| 5,735,840 A | 4/1998 | Kline et al. |
| 5,772,825 A | 6/1998 | Schmitz |
| 5,779,831 A | 7/1998 | Schmitz |
| 5,876,391 A | 3/1999 | Roe |
| 5,897,545 A | 4/1999 | Kline et al. |
| 5,916,661 A | 6/1999 | Benson et al. |
| 5,928,212 A | 7/1999 | Kline et al. |
| 5,957,908 A | 9/1999 | Kline et al. |
| 5,968,025 A | 10/1999 | Roe et al. |
| 5,971,153 A | 10/1999 | Bauer et al. |
| 6,042,673 A | 3/2000 | Johnson et al. |
| 6,079,562 A | 6/2000 | Bauer et al. |
| 6,107,537 A | 8/2000 | Elder et al. |
| 6,107,539 A | 8/2000 | Palumbo et al. |
| 6,118,041 A | 9/2000 | Roe et al. |
| 6,120,487 A | 9/2000 | Ashton |
| 6,120,489 A | 9/2000 | Johnson et al. |
| 6,153,209 A | 11/2000 | Vega et al. |
| 6,251,097 B1 | 6/2001 | Kline et al. |
| 6,410,129 B2 | 6/2002 | Zhang et al. |
| 6,426,444 B2 | 7/2002 | Roe et al. |
| 6,432,098 B1 | 8/2002 | Kline et al. |
| 6,545,197 B1 | 4/2003 | Muller et al. |
| 6,586,652 B1 | 7/2003 | Roe et al. |
| 6,617,016 B2 | 9/2003 | Zhang et al. |
| 6,627,787 B1 | 9/2003 | Roe et al. |
| 6,669,618 B2 | 12/2003 | Reising et al. |
| 6,723,035 B2 | 4/2004 | Franklin et al. |
| 6,726,792 B1 | 4/2004 | Johnson et al. |
| 6,763,944 B2 | 7/2004 | Ronn et al. |
| 6,776,316 B2 | 8/2004 | VanEperen et al. |
| 6,790,798 B1 | 9/2004 | Suzuki et al. |
| 6,825,393 B2 | 11/2004 | Roe et al. |
| 6,861,571 B1 | 3/2005 | Roe et al. |
| 6,971,153 B2 | 12/2005 | Tokizawa et al. |
| 7,028,841 B2 | 4/2006 | Otsubo |
| 7,048,124 B2 | 5/2006 | Osterdahl et al. |
| 7,059,474 B2 | 6/2006 | Tippey |
| 7,222,732 B2 | 5/2007 | Ronn et al. |
| 7,967,805 B2 | 6/2011 | Ohnishi et al. |
| 8,079,994 B2 | 12/2011 | Richlen et al. |
| 8,092,438 B2 | 1/2012 | Betts et al. |
| 8,321,049 B2 | 11/2012 | Healey et al. |
| 8,439,814 B2 | 5/2013 | Piantoni et al. |
| 8,585,666 B2 | 11/2013 | Weisman et al. |
| 9,226,861 B2 | 1/2016 | LaVon et al. |
| 2002/0072723 A1 | 6/2002 | Ronn et al. |
| 2003/0088220 A1 | 5/2003 | Molander et al. |
| 2003/0233082 A1 | 12/2003 | Kline et al. |
| 2004/0097895 A1 | 5/2004 | Busam et al. |
| 2004/0097897 A1 | 5/2004 | Ronn et al. |
| 2004/0158212 A1 | 8/2004 | Ponomarenko et al. |
| 2005/0130821 A1 | 6/2005 | Reising et al. |
| 2005/0215970 A1 | 9/2005 | Kline et al. |
| 2005/0215971 A1 | 9/2005 | Roe et al. |
| 2005/0222550 A1 | 10/2005 | Mitsui et al. |
| 2005/0234419 A1 | 10/2005 | Kline et al. |
| 2006/0030831 A1 | 2/2006 | Matsuda et al. |
| 2006/0052763 A1 | 3/2006 | Tachibana |
| 2007/0074381 A1 | 4/2007 | Raycheck et al. |
| 2007/0078426 A1 | 4/2007 | Kline et al. |
| 2007/0078427 A1 | 4/2007 | Raycheck et al. |
| 2007/0093769 A1 | 4/2007 | Kline et al. |
| 2007/0213678 A1 | 9/2007 | Thorson et al. |
| 2007/0287983 A1 | 12/2007 | Lodge |
| 2008/0021747 A1 | 1/2008 | Moeller et al. |
| 2008/0082071 A1 | 4/2008 | Bryant et al. |
| 2008/0107861 A1 | 5/2008 | Dalal et al. |
| 2009/0094941 A1 | 4/2009 | Burns, Jr. et al. |
| 2009/0098995 A1 | 4/2009 | Burns, Jr. et al. |
| 2009/0264851 A1 | 10/2009 | Richlen et al. |
| 2009/0266733 A1* | 10/2009 | Betts .................... A61F 15/001 206/440 |
| 2009/0312730 A1 | 12/2009 | LaVon et al. |
| 2011/0046772 A1 | 2/2011 | Healey et al. |
| 2011/0077609 A1 | 3/2011 | Kuwano |
| 2011/0160687 A1 | 6/2011 | Welch et al. |
| 2011/0178490 A1 | 7/2011 | LaVon et al. |
| 2011/0247199 A1 | 10/2011 | LaVon et al. |
| 2011/0272315 A1 | 11/2011 | Dixon |
| 2012/0246915 A1 | 10/2012 | LaVon et al. |
| 2013/0018351 A1 | 1/2013 | Desai |
| 2013/0072887 A1* | 3/2013 | LaVon .................... A61F 13/49 604/368 |
| 2013/0110068 A1 | 5/2013 | Nelson et al. |
| 2013/0211355 A1 | 8/2013 | Nishikawa et al. |
| 2013/0211356 A1 | 8/2013 | Nishikawa et al. |
| 2013/0211357 A1 | 8/2013 | Nishikawa et al. |
| 2013/0244355 A1 | 9/2013 | Chen et al. |
| 2013/0270065 A1 | 10/2013 | Papsdorf et al. |
| 2013/0306226 A1 | 11/2013 | Zink et al. |
| 2016/0136004 A1 | 5/2016 | LaVon et al. |

FOREIGN PATENT DOCUMENTS

| | | |
|---|---|---|
| JP | 03-231660 | 10/1991 |
| JP | 2003-180751 | 7/2003 |
| JP | 2004-188225 | 7/2004 |
| JP | 2005-126119 | 5/2005 |
| JP | 2008-289640 | 12/2008 |
| WO | WO 01/056524 A1 | 8/2001 |
| WO | WO-2007146153 | 12/2007 |
| WO | WO-2011/126828 | 10/2011 |

OTHER PUBLICATIONS

All Office Actions for U.S. Appl. No. 13/074,058.
All Office Actions for U.S. Appl. No. 13/371,919.
All Office Actions for U.S. Appl. No. 13/372,940.
All Office Actions for U.S. Appl. No. 14/953,471.
All Office Actions for U.S. Appl. No. 13/764,954.
All Office Actions for U.S. Appl. No. 16/192,854.
All Office Actions for U.S. Appl. No. 13/764,964.
All Office Actions for U.S. Appl. No. 16/162,976.

* cited by examiner

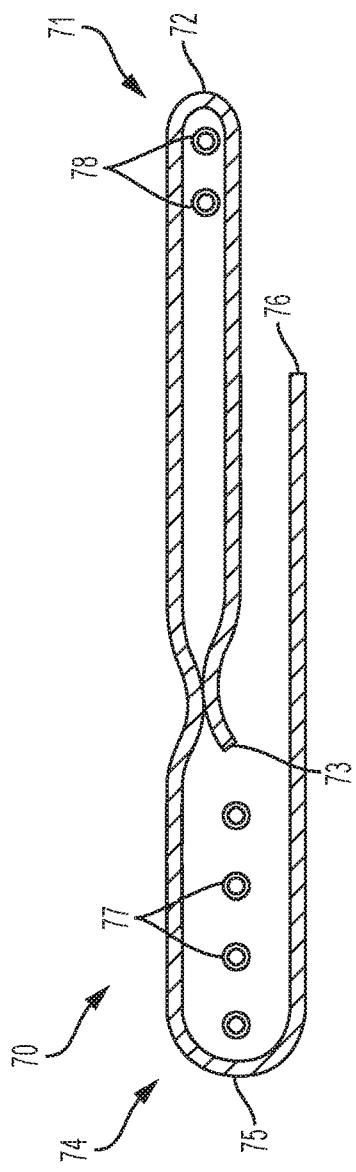
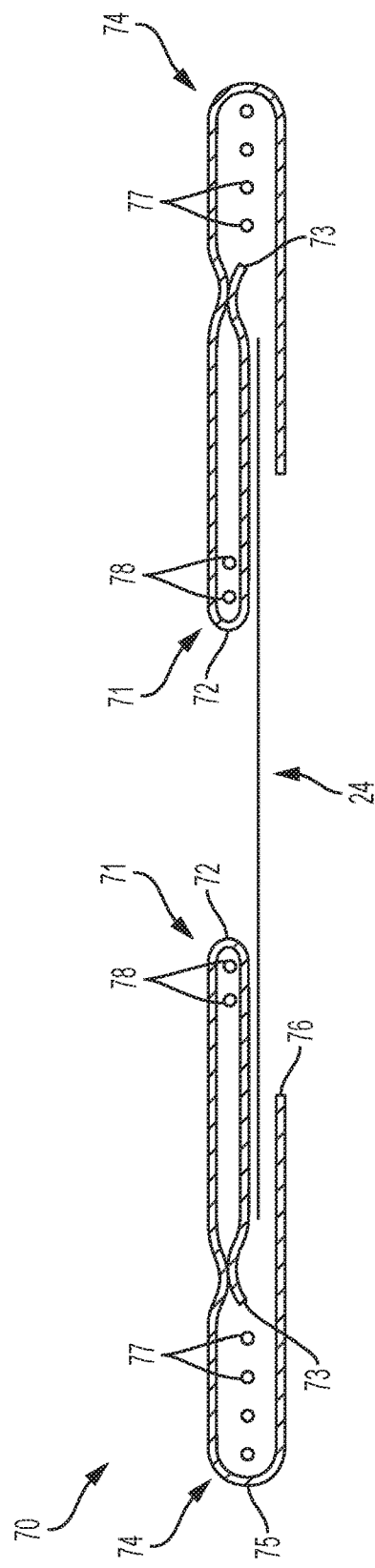

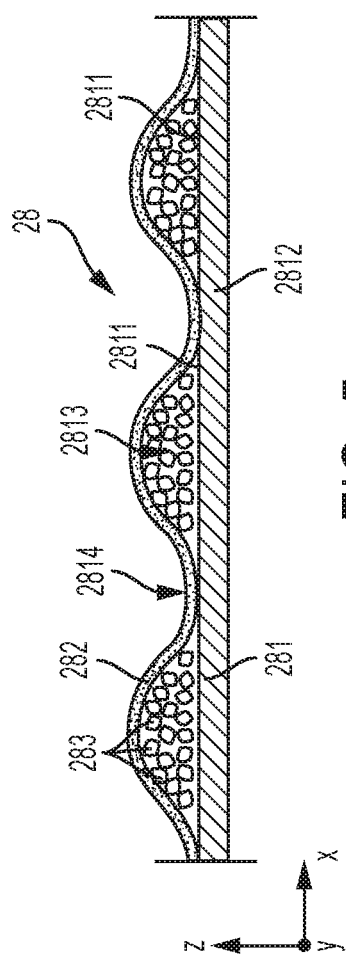
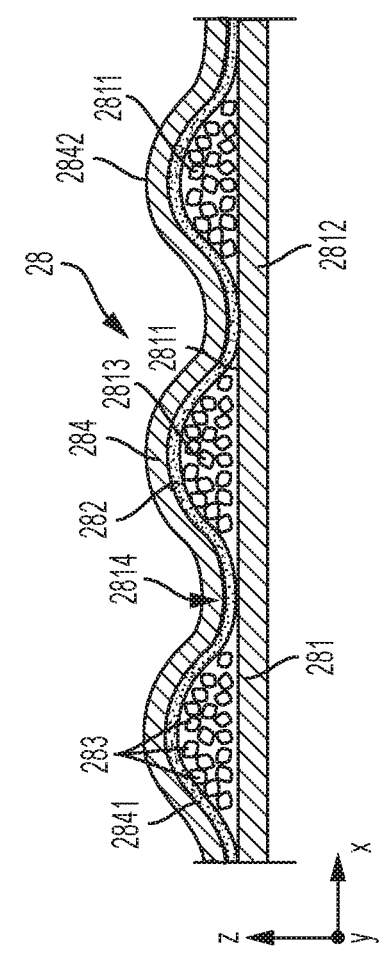

ABSORBENT ARTICLES COMPRISING SUBSTANTIALLY IDENTICAL CHASSIS AND SUBSTANTIALLY IDENTICAL FLAPS

CROSS REFERENCE TO RELATED APPLICATIONS

This application claims the benefit, under 35 USC 119(e), to U.S. Provisional Patent Application No. 62/220,570 filed on Sep. 18, 2015, which is herein incorporated by reference in its entirety.

FIELD

This invention relates to absorbent articles comprising substantially identical chassis and flaps and more particularly to an array of taped and pant absorbent articles comprising substantially identical chassis and flaps.

BACKGROUND

Disposable absorbent articles such as diapers are designed to absorb and contain bodily waste to prevent soiling of the body and clothing. These articles are typically available in taped and pant type articles, as well as inserts. Typically, taped articles are packaged without being pre-closed, whereas pant articles are pre-closed. Pant articles are often used for potty training, but not necessarily.

Taped and pant articles are commonly sold by the same company, but are typically made at different manufacturing sites and/or made on different manufacturing lines. Further, these different forms typically comprise different ears or flaps and a different chassis, including different compositions and dispositions of cores and leg cuffs.

Beyond the expense and complexity with making these articles separately, there is often a fundamentally different fit and performance between taped and pant articles.

This is often true even when they are made by the same company and sold under a common brand name and/or trade name.

It is an object of the present application to disclose how to make substantial portions of taped and pant articles in the same manner, such that there is a substantial structural overlap between components of taped and pant articles. It is an object of the present application to disclose the use of the same (or substantially the same) chassis and flaps on both pant and taped articles. And, it is an object of the present application to disclose how to display and arrange said articles for sale.

SUMMARY

In one embodiment, an array of taped and pant articles of the present disclosure may comprise a first and second package of absorbent articles. The first package may comprise a taped article comprising a first chassis and a first belt flap. The first belt flap may comprise first and second nonwovens and a first elastic layer disposed therebetween. The first belt flap may be joined to the first chassis via a first belt flap adhesive. The second package may comprise a pant article comprising a second chassis and a second flap. The second belt flap may comprise third and fourth nonwovens and a second elastic layer disposed therebetween. The second belt flap may be joined to the second chassis via a second belt flap adhesive. The first and second chassis may be at least substantially identical, such that:

each of the first and second chassis comprise the same or substantially the same dimensions of one or more of: core width at the lateral centerline, core width at one of the front or rear core end, a distance from a left outer cuff distal edge to a right outer cuff distal edge, a distance from a left inner cuff distal edge to a left outer cuff distal edge, a distance from a left inner cuff proximal edge to a right inner cuff proximal edge, a distance from a left inner cuff proximal edge to a left outer cuff distal edge, a free height of the inner cuff, inner cuff hem fold width, inner cuff elastics length, outer cuff elastics length, core length, and backsheet width;

each of the first and second chassis comprise at least substantially identical chemical compositions of one or more of a topsheet, backsheet film, backsheet nonwoven, core SAPs (Super Absorbent Polymer), core pulp, core nonwoven, core tissue, leg cuff film, leg cuff nonwoven, SAP adhesive, core nonwoven adhesive, leg cuff elastic adhesive, and backsheet nonwoven/film adhesive; and each of the first and second chassis comprise substantially the same or substantially the same basis weight of one or more of the topsheet, backsheet film, backsheet nonwoven, core SAPs, core pulp, leg cuff nonwoven, leg cuff film, SAP adhesive, leg cuff adhesive, and backsheet nonwoven/film adhesive.

The first and second belt flaps may be at least substantially identical, such that:

each of the first and second belt flaps comprise a same, or substantially the same, longitudinal distance m;

each of the first and second belt flaps comprise a same, or substantially the same, transverse distance n;

each of the first and second belt flaps comprise a same, or substantially the same, longitudinal distance, o, between an end edge of the first chassis and an end edge of the first belt flap and an end edge of the second chassis and an end edge of the second belt flap;

each of the first and second belt flaps comprise a same, or substantially the same, longitudinal distance, p, between the end edge of the first chassis and a proximal edge of the first belt flap and the end edge of the second chassis and a proximal edge of the second belt flap;

each of the first and second belt flaps comprise a same, or substantially the same, longitudinal distance, q, between an end edge of a first flap-to-chassis adhesive pattern and the end edge of the first belt flap and the end edge of the second chassis and an end edges of the second belt flap;

each of the first and second belt flaps comprise a same, or substantially the same, transverse distance, r, between the end edge of a first flap-to-chassis adhesive pattern and the end edge of the first belt flap and the end edge of the second chassis and the end edges of the second belt flap;

each of the first and second belt flaps comprise identical chemical compositions of the first and third nonwovens;

each of the first and second belt flaps comprise identical chemical compositions of the second and fourth nonwovens;

each of the first and second belt flaps comprise identical chemical compositions of the first and second adhesives;

each of the first and second belt flaps have the same, or substantially the same, basis weights of the first and third nonwovens;

each of the first and second belt flaps have the same, or substantially the same, basis weights of the second and fourth nonwovens;

each of the first and second belt flaps have the same, or substantially the same, basis weights of the first and second adhesives;

The taped article may not be pre-closed, while the pant article may be pre-closed. The taped and pant articles may be manufactured by the same manufacturer. And the first package may comprise a first user weight range and the second package may comprise a second user weight range. The first and second weight ranges may overlap, at least in part.

In another embodiment, taped and pant articles of the present disclosure may comprise a first and second package of absorbent articles. The first package may comprise a taped article comprising a first chassis. The second package comprise a pant article comprising a second chassis. The first and second chassis may be at least substantially identical, such that:

the first and second chassis have at least one identical component cross sectional order and disposition of a topsheet, backsheet, core, including the core wrap, in at least one the front waist region, back waist region, and crotch region; and a first core pulp width of the first chassis is at least substantially identical to a second core pulp width of the second chassis.

The taped article may not be pre-closed, while the pant article may pre-closed. The taped and pant articles may be manufactured by the same manufacturer. And the first package may comprise a first weight range and the second package may comprise a second weight range. The first and second weight ranges may overlap, at least in part.

In another embodiment, taped and pant articles of the present disclosure may comprise a first and second package of absorbent articles. The first package may comprise a taped article comprising a first chassis. The second package may comprise a pant article comprising a second chassis. The first and second chassis may be at least substantially identical. The taped article may not be pre-closed, while the pant article may be pre-closed to form a waist opening and leg openings. The taped and pant articles may be manufactured by the same manufacturer. The first package may comprise indication of a first size, and the second package may comprise indication of a second size. The first and second sizes may be different. The first package may comprise size X articles and the second package comprises size X+1 articles.

BRIEF DESCRIPTION OF THE DRAWINGS

FIG. 2 is a schematic cross section view of an exemplary embodiment of a folded outer leg cuff, suitable in one embodiment of the invention.

FIG. 3 is a schematic cross section view of an exemplary embodiment of a folded outer leg cuff, suitable in one embodiment of the invention.

FIG. 5 is a schematic cross section view of an example of an absorbent core suitable in one embodiment of the invention.

FIG. 6 is a schematic cross section view of another example of an absorbent core suitable in one embodiment of the invention.

DETAILED DESCRIPTION OF THE INVENTION

Figure 1A:
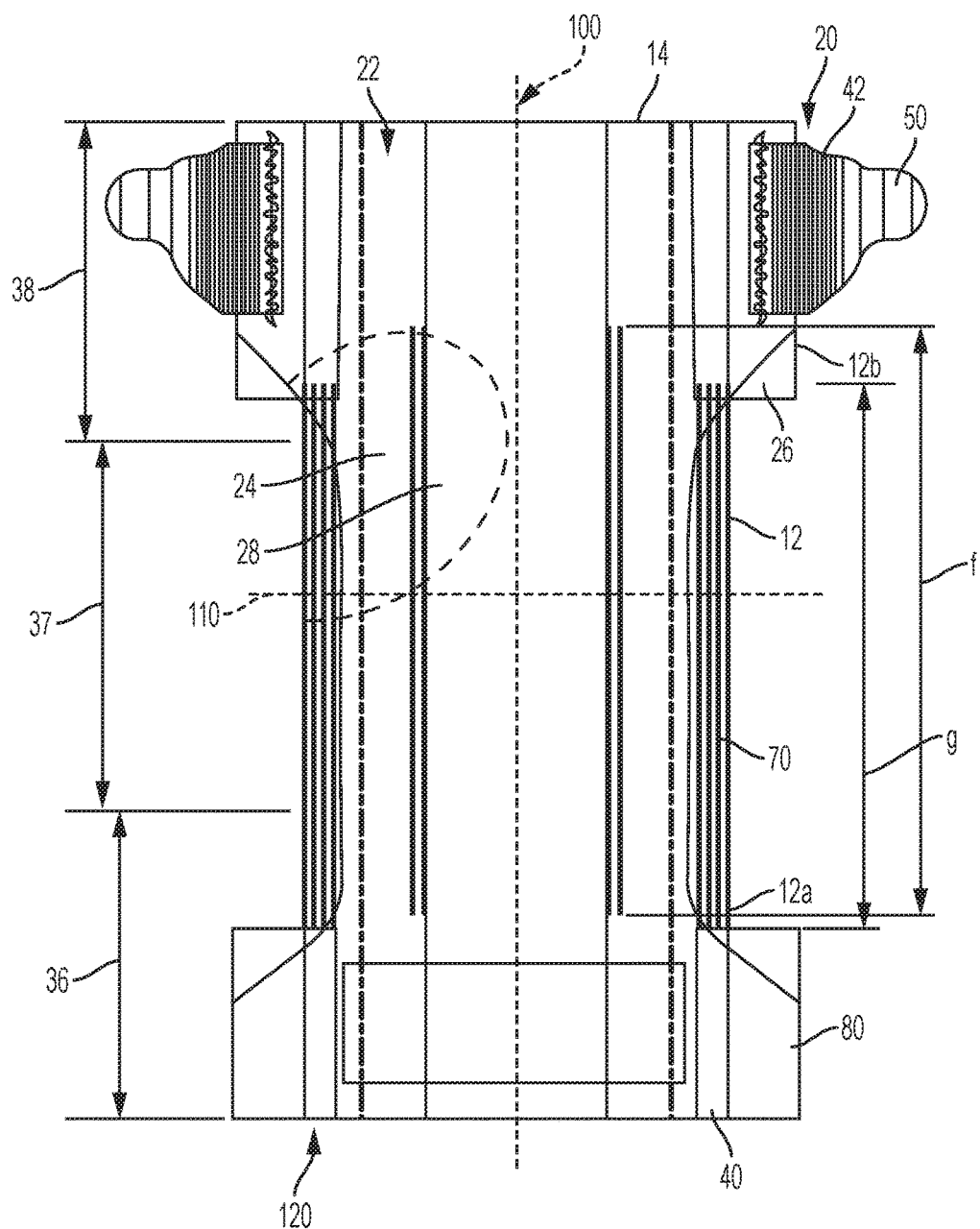
FIG. 1a is a plan view of an exemplary absorbent article laid out flat, suitable in one embodiment of the invention.

As used herein, the following terms shall have the meaning specified thereafter:

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Proximal" and "Distal" refer respectively to the location of an element relatively near to or far from the longitudinal or lateral centerline of a structure (e.g., the proximal edge of a longitudinally extending element is located nearer to the longitudinal centerline than the distal edge of the same element is located relative to the same longitudinal centerline).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal"

"Lateral" refers to a direction running from a longitudinally extending edge to an opposing longitudinally extending edge of the article and generally at a right angle to the longitudinal direction. Directions within 45 degrees of the lateral direction are considered to be "lateral."

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure, e.g., hydrostatic pressure (aside from natural forces such as gravity). A layer or a layered structure that is water-impermeable according to this definition may be permeable to water vapor, i.e., may be "vapor-permeable."

"Extendibility" and "extensible" mean that the width or length of the component in a relaxed state can be extended or increased.

"Elasticated" and "elasticized" mean that a component comprises at least a portion made of elastic material.

"Elongatable material," "extensible material," or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Elastomeric material" is a material exhibiting elastic properties. Elastomeric materials may include elastomeric films, scrims, nonwovens, and other sheet-like structures.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers," "prefastened diapers," "pull-on diapers," "training pants," "diaper-pants," and "pre-closed diapers."

"Identical" means the objects being compared are the same (e.g., backsheet film A compared to backsheet film B, topsheet A compared to topsheet B, chassis A compared to chassis B, portions of article A compared to the same portions of article B, etc.).

"Substantially identical" means the objects being compared have such close resemblance as to be essentially the same—as understood by one having ordinary skill in the art. "At least substantially identical" encompasses "identical."

"Closed form" means opposing waist regions are joined, as packaged, either permanently or refastenably to form a continuous waist opening and leg openings. Suitable closed form pant articles of the present disclosure are disclosed in U.S. Pat. No. 9,072,632.

"Open form" means opposing waist regions are not initially joined to form a continuous waist opening and leg openings but comprise a closure means such as a fastening system to join the waist regions to form the waist and leg openings before or during application to a wearer of the article. Suitable open form taped articles of the present disclosure are disclosed in U.S. Ser. No. 62/220,265, filed on Sep. 18, 2015. "Array" means a display of packages comprising disposable absorbent articles of different article constructions (e.g., different elastomeric materials [compositionally and/or structurally] in the side panels, side flaps and/or belts flaps, different graphic elements, different product structures, fasteners or lack thereof) said packages having the same brand and/or sub-brand and/or the same trademark registration and/or having been manufactured by or for a common manufacturer and said packages available at a common point of sale, e.g. oriented in proximity to each other in a given area of a retail store. An array is marketed as a line-up of products normally having like packaging elements (e.g., packaging material type, film, paper, dominant color, design theme, etc.) that convey to consumers that the different individual packages are part of a larger line-up. Arrays often have the same brand, for example, "Huggies," and same sub-brand, for example, "Pull-Ups." A different product in the array may have the same brand "Huggies" and the sub-brand "Little Movers." The differences between the "Pull-Ups" product of the array and the "Little Movers" product in the array may include product form, application style, different fastening designs or other structural elements intended to address the differences in physiological or psychological development. Furthermore, the packaging is distinctly different in that "Pull-Ups" is packaged in a predominately blue or pink film bag and "Little Movers" is packaged in a predominately red film bag.

Further regarding "Arrays," as another example an array may be formed by different products having different product forms manufactured by the same manufacturer, for example, "Kimberly-Clark", and bearing a common trademark registration for example, one product may have the brand name "Huggies," and sub-brand, for example, "Pull-Ups." A different product in the array may have a brand/sub-brand "Good Nites" and both are registered trademarks of The Kimberly-Clark Corporation and/or are manufactured by Kimberly-Clark. Arrays also often have the same trademarks, including trademarks of the brand, sub-brand, and/or features and/or benefits across the line-up.

"On-line Array" means an "Array" distributed by a common on-line source.

Absorbent Article

An absorbent article as disclosed herein may comprise a chassis. The chassis is defined by the backsheet, topsheet, absorbent core, leg cuffs, including the layers making up each of these components, as well as the adhesives joining them together. The absorbent article may also comprise flaps (including, and also referred to as side flaps, ears, side panels, belts, belt-like flaps, article flaps, etc.) and a fastening systems (including disposal means, fasteners, fastening components, etc.), as well as other components (including sensors, wetness indicators, lotions, waistbands, perfumes, etc.).

Taped and pant absorbent articles as disclosed herein may be manufactured by the same company on the same manufacturing line and may sold in an array under the same brand (e.g., Pampers and Huggies) and/or trade name (Cruisers, Swaddlers, and Easy Ups, Baby Dry, etc.).

Figure 1B:
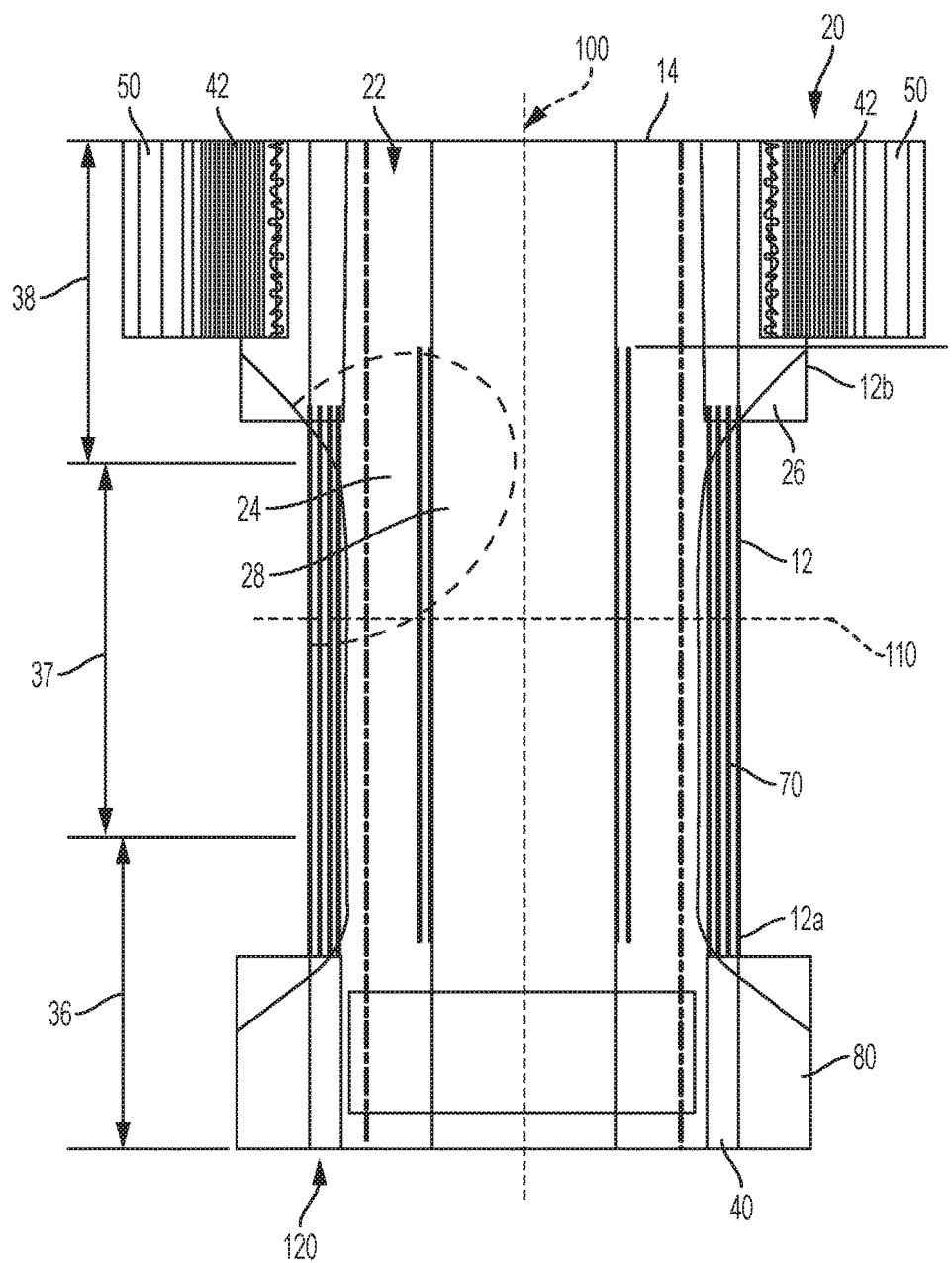
FIG. 1b is a plan view of an exemplary absorbent article laid out flat, suitable in one embodiment of the invention.
Figure 1C:
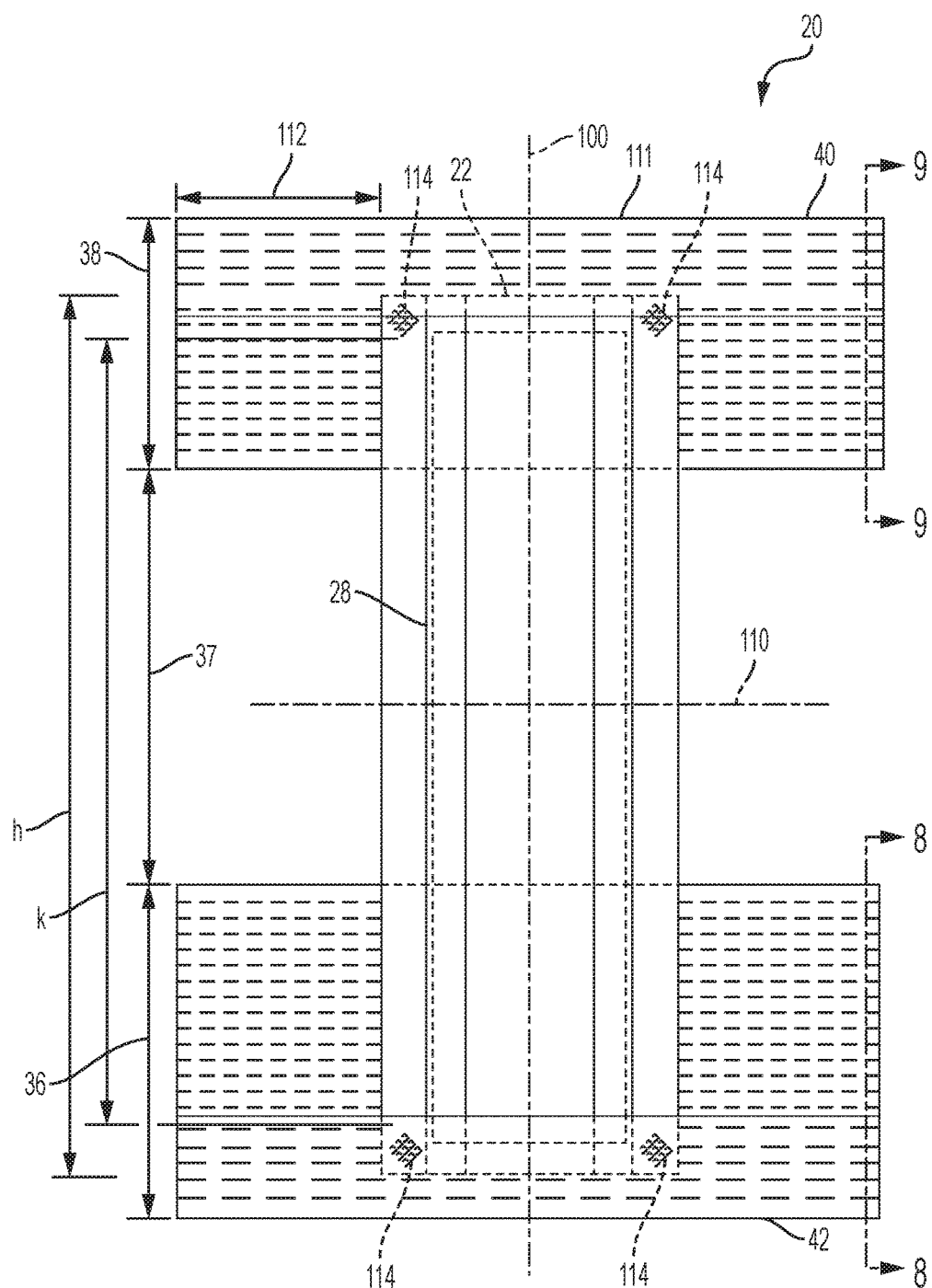
FIG. 1c is a plan view of an exemplary absorbent article laid out flat, suitable in one embodiment of the invention.
Figure 1D:
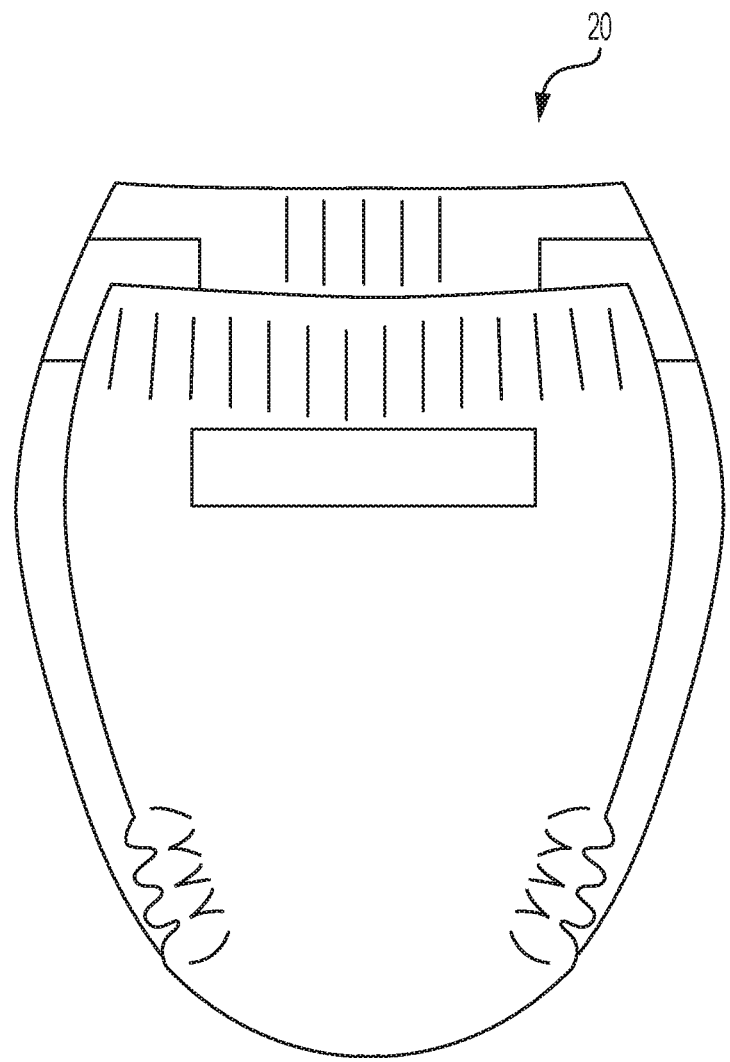
FIG. 1d is a perspective view of an exemplary taped article in a folded configuration, suitable in one embodiment of the invention.
Figure 1E:
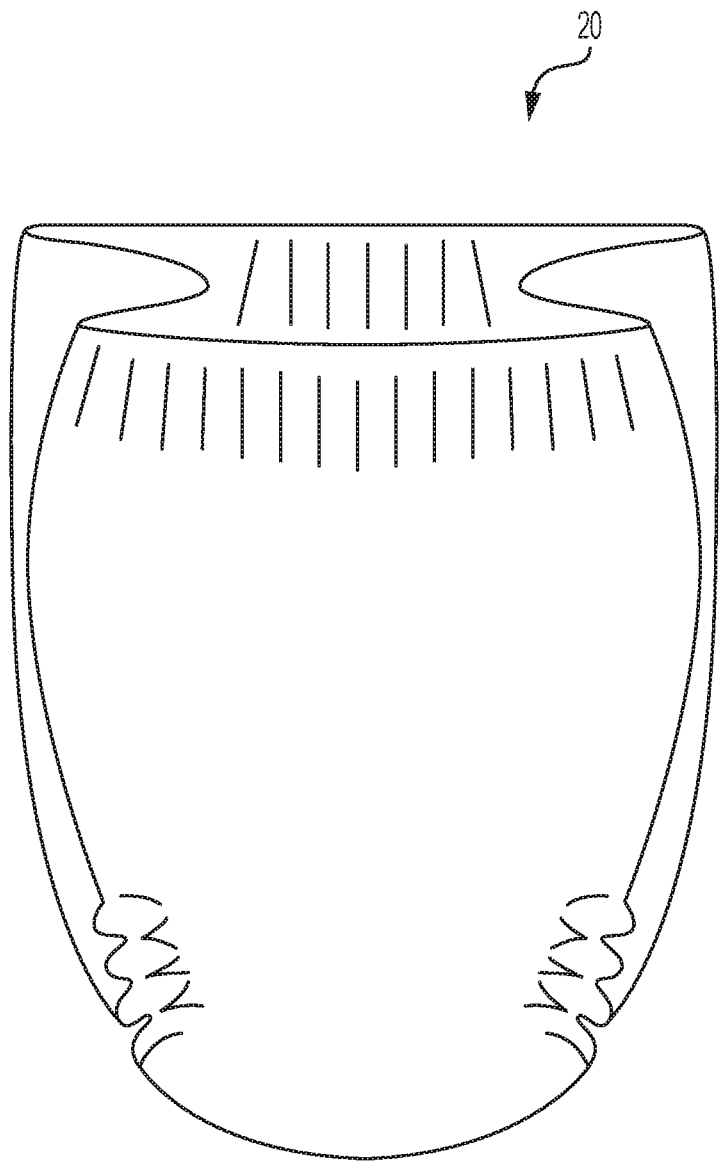
FIG. 1e is a perspective view of an exemplary pant article in a folded configuration, suitable in one embodiment of the invention.
Figure 1F:
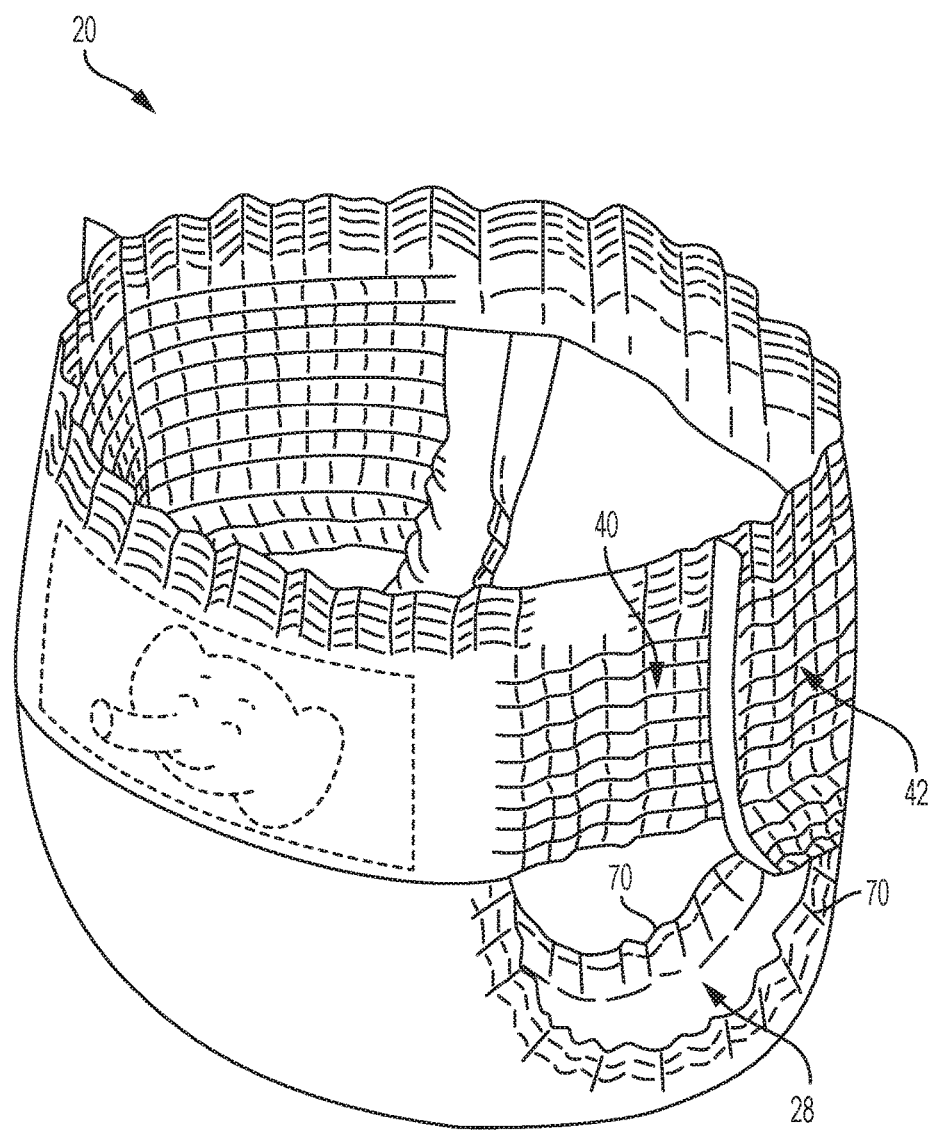
FIG. 1f is a perspective view of an exemplary pant article, suitable in one embodiment of the invention.
Figure 1G:
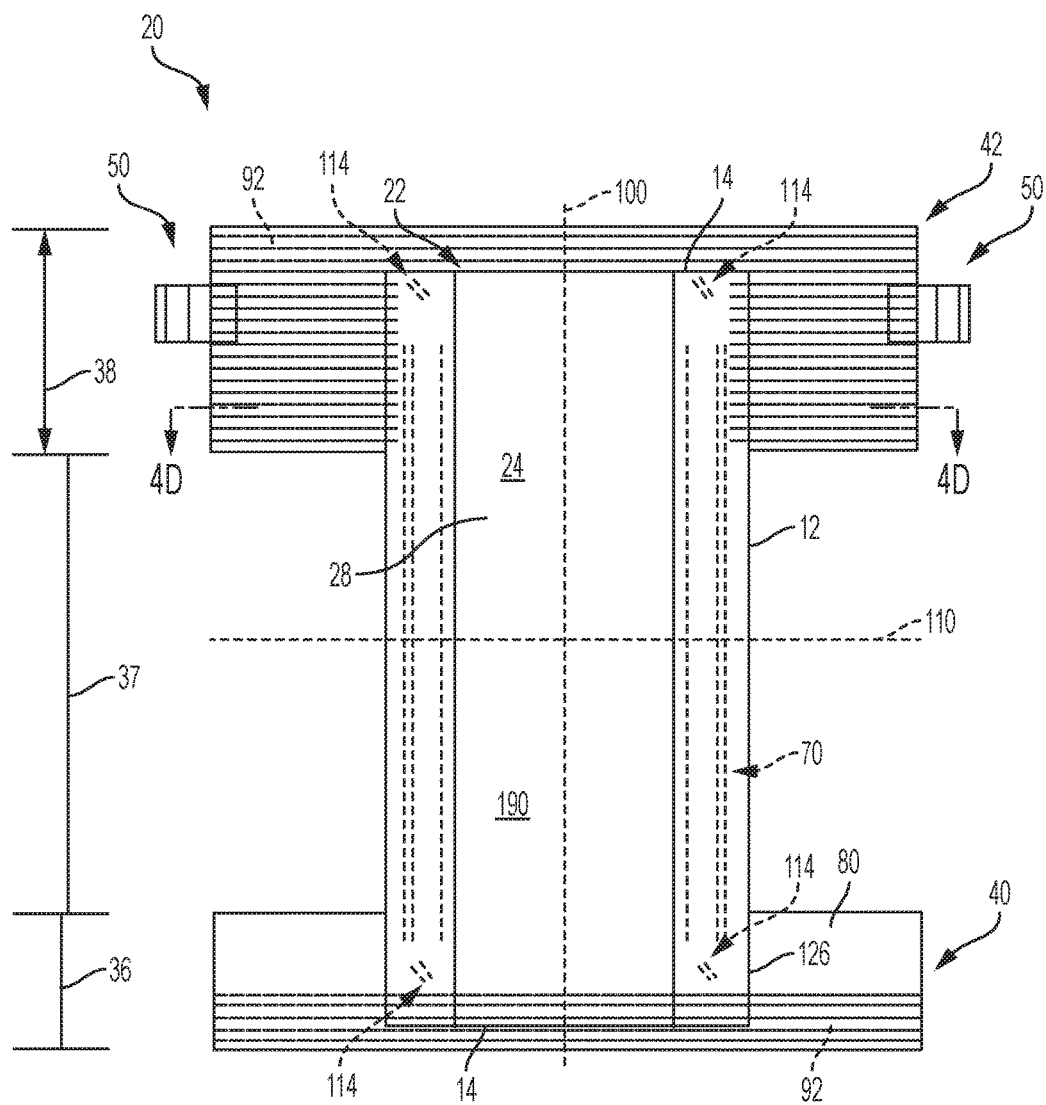
FIG. 1g is a plan view of an exemplary taped absorbent article laid out flat, suitable in one embodiment of the invention.

FIGS. 1a-c is a plan view of an exemplary, non-limiting embodiment of an absorbent article 20 of the present disclosure in a flat, uncontracted state (i.e., without elastic induced contraction). The garment-facing surface 120 of the absorbent article 20 is facing the viewer. The absorbent article 20 includes a longitudinal centerline 100 and a lateral centerline 110. The absorbent article 20 may comprise a chassis 22. The absorbent article 20 and chassis 22 are shown to have a front waist region 36, a rear (or back) waist region 38 opposed to the front waist region 36, and a crotch region 37 located between the front waist region 36 and the rear waist region 38. The waist regions 36 and 38 generally comprise those portions of the absorbent article 20 which, when worn, encircle the waist of the wearer. The waist regions 36 and 38 may include elastic elements such that they gather about the waist of the wearer to provide improved fit and containment. The crotch region 37 is that portion of the absorbent article 20 which, when the absorbent article 20 is worn, is generally positioned between the legs of the wearer.

Chassis

Because the chassis is made up of numerous components, it is understood that when comparing two or more chassis, the greater the overlap between the composition and disposition of the chassis components, the more identical they can be considered. The outer periphery of chassis 22 is defined by opposing longitudinally extending edges 12 and opposing laterally extending edges 14. The longitudinal edges 12 may be subdivided into a front longitudinal edge 12a, which is the portion of the longitudinal edge 12 in the front waist region 36, and a rear longitudinal edge 12b, which is the portion of the longitudinal edge 12 in the rear waist region 38. The chassis 22 may have opposing longitudinal edges 12 that are oriented generally parallel to the longitudinal centerline 100. However, for better fit, longitudinal edges 12 may be curved or angled to produce, for example, an "hourglass" shape diaper when viewed in a plan view. The chassis 22 may have opposing lateral edges 14 that are oriented generally parallel to the lateral centerline 110.

The chassis 22 may comprise a liquid permeable topsheet 24, a backsheet 26, and an absorbent core 28 between the topsheet 24 and the backsheet 26. The absorbent core 28 may have a body-facing surface and a garment-facing-surface. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In certain embodiments, the chassis 22 comprises the main structure of the absorbent article 20 with other features added to form the composite diaper structure. While the topsheet 24, the backsheet 26, and the absorbent core 28 may be assembled in a variety of well-known configurations, suitable configurations are described generally in U.S. Pat. Nos. 3,860,003; 5,151,092; 5,221,274; 5,554,145; 5,569, 234; 5,580,411; and 6,004,306.

The topsheet 24 is generally a portion of the absorbent article 20 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. One topsheet 24 useful herein is available from BBA Fiberweb, Brentwood, Tenn. as supplier code 055SLPV09U.

Any portion of the topsheet 24 may be coated with a lotion or skin care composition as is known in the art. Examples of suitable lotions include those described in U.S. Pat. Nos. 5,607,760; 5,609,587; 5,635,191; and 5,643,588. The topsheet 24 may be fully or partially elasticized or may be foreshortened so as to provide a void space between the topsheet 24 and the core 28. Suitable structures including elasticized or foreshortened topsheets are described in more detail in U.S. Pat. Nos. 4,892,536; 4,990,147; 5,037,416; and 5,269,775.

The absorbent core 28 may comprise a wide variety of liquid-absorbent materials 97 commonly used in disposable diapers and other absorbent articles. Examples of suitable absorbent materials include comminuted wood pulp, which is generally referred to as air felt, creped cellulose wadding, melt blown polymers, including co-form; chemically stiffened, modified or cross-linked cellulosic fibers; tissue, including tissue wraps and tissue laminates; absorbent foams; absorbent sponges; superabsorbent polymers (SAPs); absorbent gelling materials (AGMs); or any other known absorbent material or combinations of materials. The absorbent materials may be contained by one or more core wrap layers 95 (see FIG. 4a), which may include a core cover 95a (top layer) and a dusting layer 95b (bottom layer). In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. Non-limiting examples of suitable absorbent cores are described in greater details below.

Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316; and 5,625,222.

As will be seen and appreciated below, taped and pant articles may comprise identical of substantially identical absorbent cores 28, including core width (that is, pulp/AGM or SAP width). This may be particularly useful for achieving two different article forms that fit in a like manner. The identical or substantially identical nature of the absorbent cores may be particularly important, especially the materials utilized in the core as well as the overall composition of the absorbent core—for example the amount and type of AGM relative to the amount and type of absorbent fiber.

The backsheet 26 is generally positioned such that it may form at least a portion of the garment-facing surface 120 of the absorbent article 20. Backsheet 26 may be designed to prevent the exudates absorbed by and contained within the absorbent article 20 from soiling articles that may contact the absorbent article 20, such as bed sheets and undergarments. In certain embodiments, the backsheet 26 is substantially water-impermeable. Suitable backsheet 26 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the absorbent article 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. A suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer. The backsheet 26 may comprise an outer cover layer 26b and an inner layer 26a. The outer cover layer may be made of a soft, non-woven material. The inner layer may be a film material. The backsheet 26 may comprise a graphic patch layer. At least one of the layers may comprise a single color or multi-color prints on one or more of the surfaces. The inner layer may be made of a substantially liquid-impermeable film. The outer cover and an inner layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

The absorbent article 20 may include front flaps 40 and/or back flaps 42. The flaps 40, 42 may be partially or totally extensible, inextensible, elastic, or inelastic. The flaps 40, 42 may be formed from nonwoven webs, woven webs, knitted fabrics, polymeric and elastomeric films, apertured films, sponges, foams, scrims, and combinations and laminates thereof. In certain embodiments the flaps 40, 42 may be formed of a stretch laminate such as a nonwoven/elastomeric material laminate or a nonwoven/elastomeric material/nonwoven laminate. Stretch laminates may be formed by any method known in the art. For example, the flaps 40, 42 may be formed as a zero strain stretch laminate, which includes at least a layer of non-woven material and an elastomeric element. The elastomeric element is attached to the layer of non-woven material while in a relaxed or substantially relaxed state, and the resulting laminate is made stretchable (or more stretchable over a further range) by subjecting the laminate to an activation process which elongates the nonwoven layer permanently, but the elastomeric element temporarily. The nonwoven layer may be integral with at least a portion of the chassis 22, in which case the elastomeric element may be attached to the non-woven layer and the non-woven/elastomeric element laminate is subsequently activated. Alternatively, the nonwoven layer may be a separate component, in which case the elastomeric element is attached to the nonwoven layer to form the laminate, which is then coupled to the chassis. If one or more layers of the side panel are provided separately, the laminate may be activated either before or after attachment to the main portion. The zero strain activation processes is further disclosed in U.S. Pat. Nos. 5,167,897 and 5,156,793. A suitable elastic flap may be an activated laminate comprising an elastomeric film (such as is available from Tredegar Corp, Richmond, Va., as supplier code X25007) disposed between two nonwoven layers (such as is available from BBA Fiberweb, Brentwood, Tenn. as supplier code FPN332). In an alternative embodiment, the flaps may comprise a plurality of elastic strands disposed between a pair of nonwoven layers. In such an embodiment the flaps may be continuous from one distal edge of the flap across the chassis to an opposing distal edge of the flap. The absorbent article 20 may further include a disposal tape. The disposal tape may be located on an exterior surface of the chassis and/or an external surface of one of the flaps.

Flaps

Because the flaps may be made up of numerous components (including different nonwovens composition, nonwoven fold dispositions, elastics compositions, elastic spacing, elastic strain, etc.), it is understood that when comparing two or more flaps, the greater the overlap between the composition and disposition of the flap elements, the more identical they can be considered. Taped and pant articles of the present disclosure may comprise identical or substantially identical flaps.

The flaps 40, 42 may be discrete from or integral with the chassis. A discrete flap is formed as separate element which is joined to the chassis 22. In some embodiments, this includes a plurality of flaps, e.g. 2 or 4 (often referred to as ear panels or side flaps) being joined to the side edges of the chassis in the front and/or rear waist regions. In other embodiments this may include a front and/or back belt-like flaps being joined across the front and back (or rear) waist regions of the chassis, at least across end edges of the chassis (see FIGS. 1g-1k).

Figure 4A:
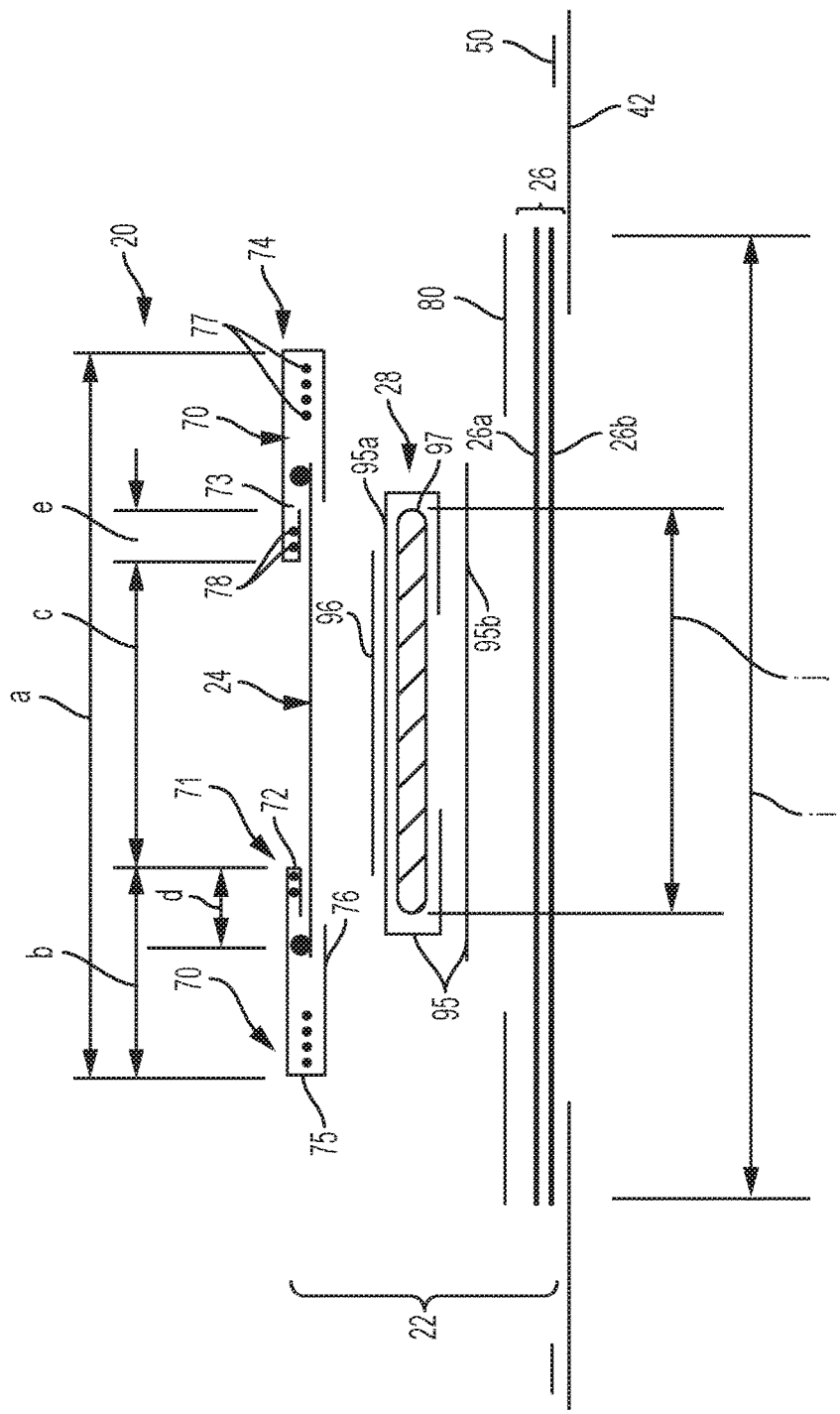
FIG. 4a is a schematic cross section view of an exemplary absorbent article, suitable in one embodiment of the invention.
Figure 11:
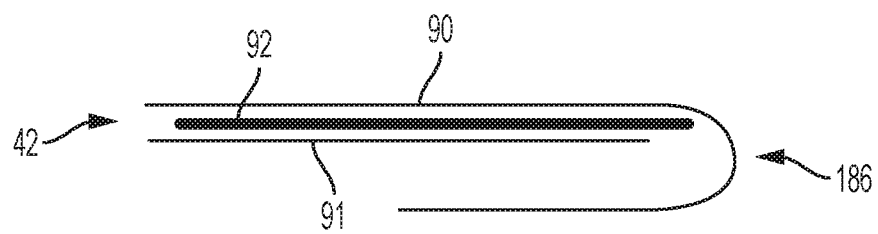
FIG. 11 is a schematic cross section view of a front belt-like flap suitable in one embodiment of the invention, taken along 8-8 of FIG. 1c.
Figure 12:
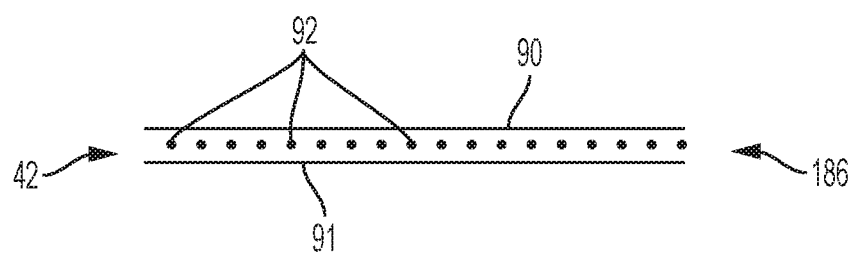
FIG. 12 is a schematic cross section view of a front belt-like flap suitable in one embodiment of the invention, taken along 8-8 of FIG. 1c.

Referring to FIGS. 8-12, the belt-like flaps 40 and 42 may comprise an inner nonwoven layer 90 and an outer nonwoven layer 91 and elastics 92 therebetween. The inner and outer nonwoven layers may be joined using adhesive or thermoplastic bonds. Various suitable belt-like flap configurations can be found in Ser. No. 13/764,990, filed on Feb. 12, 2012, now U.S. Pat. No. 9,072,632, and claiming priority to U.S. App. No. 61/598,012, filed on Feb. 13, 2012, titled DISPOSABLE PULL-ON GARMENT, by the Procter & Gamble Company. As shown in FIGS. 11 and 4e, a film layer may be used as the elastic instead of elastic strands illustrated in FIGS. 8, 9, 10, and 12). The film layer may be apertured as disclosed in U.S. Pat. Nos. 6,410,129; 7,087,287; and U.S. Pub. No. 2007-0287348.

An integral flap is a portion, one or more layers, of the chassis 22 that projects laterally outward from the longitudinal edge 12. The integral flap may be formed by cutting the chassis to include the shape of the flap projection.

As shown in FIGS. 1a-1c, 1f-1h, 1k, articles of the present disclosure may have flaps in both the front and back waist regions. FIGS. 1i and 1j illustrate articles having flaps in only the back waist region. Articles of the present disclosure may also have flaps in only the front waist region. Further, the flaps in the front and/or the back waist regions may not comprise any elastics, or may comprise substantial zones that are not elasticized.

The flap elastics, including strands, scrims, ribbons, bands, and/or films, may comprise elastic profiles as disclosed in U.S. Pat. No. 9,072,632 and U.S. Ser. No. 13/893,604.

As shown in FIGS. 8-12, the inner and/or outer nonwovens 90 and 91 of the belt-like flap may form an end edge 186 that defines the waist opening. The inner and/or outer nonwovens may be folded over one another or upon themselves, or may co-terminate to form the end edge 186. Please note that the nonwoven configurations of 91 and 92 in FIGS. 8-12 may be used for a belt-like flap in the front or the back waist regions, and may be mixed in matched in the front or back waist regions as desired.

Figure 1H:
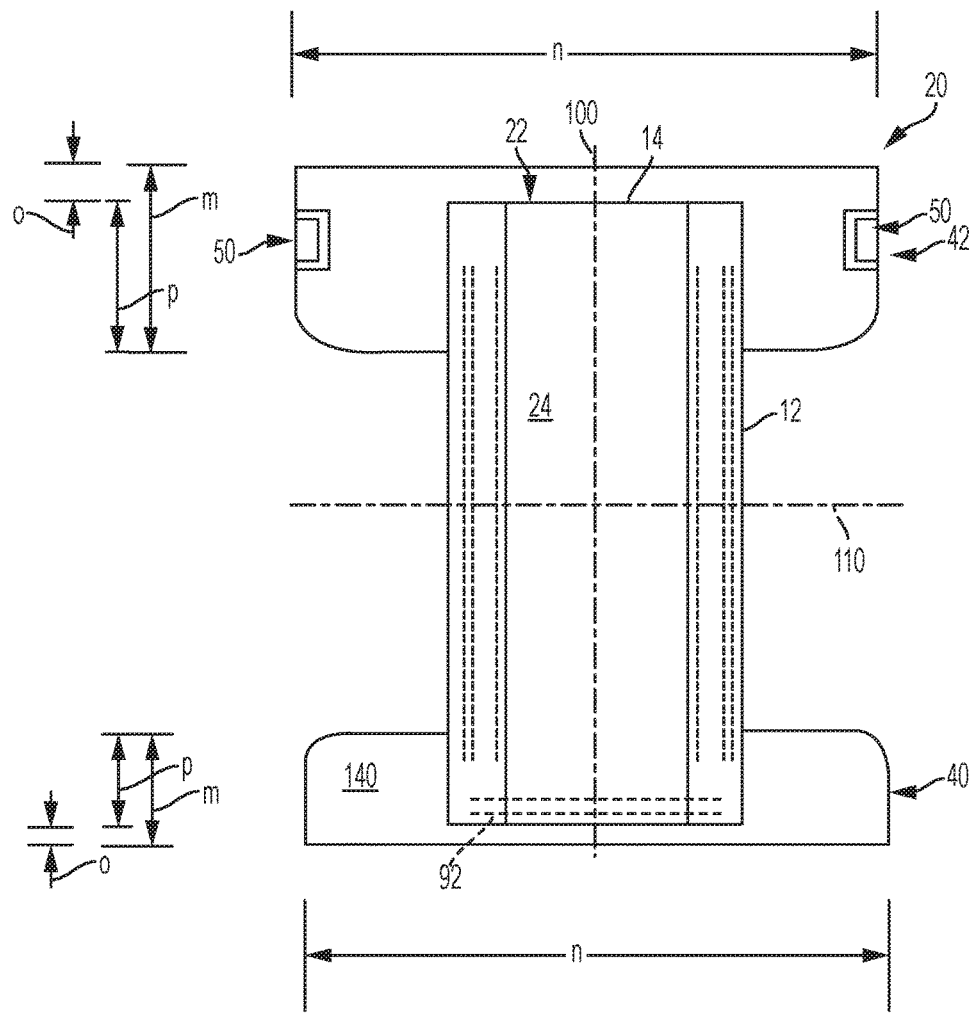
FIG. 1h is a plan view of an exemplary taped absorbent article laid out flat, suitable in one embodiment of the invention.
Figure 1I:
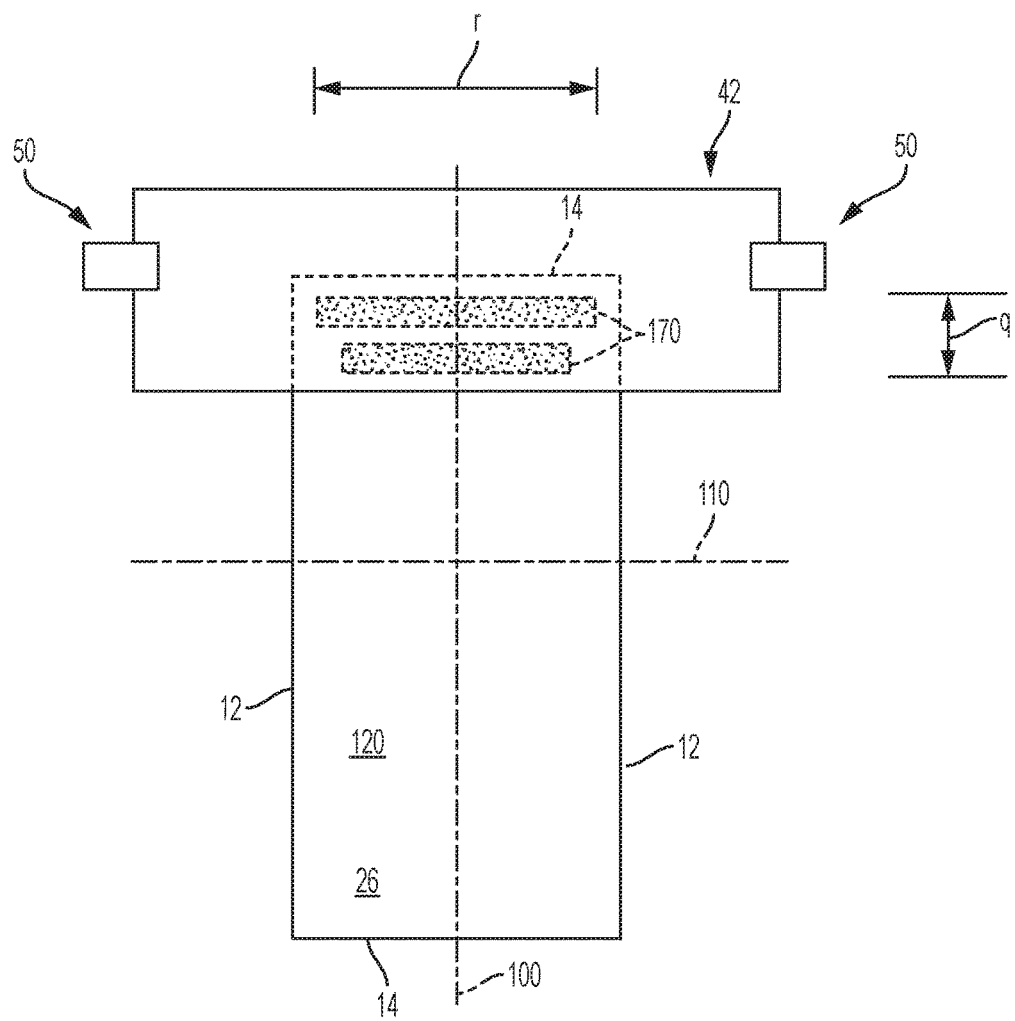
FIG. 1i is a plan view of an exemplary taped absorbent article laid out flat, suitable in one embodiment of the invention.
Figure 1J:
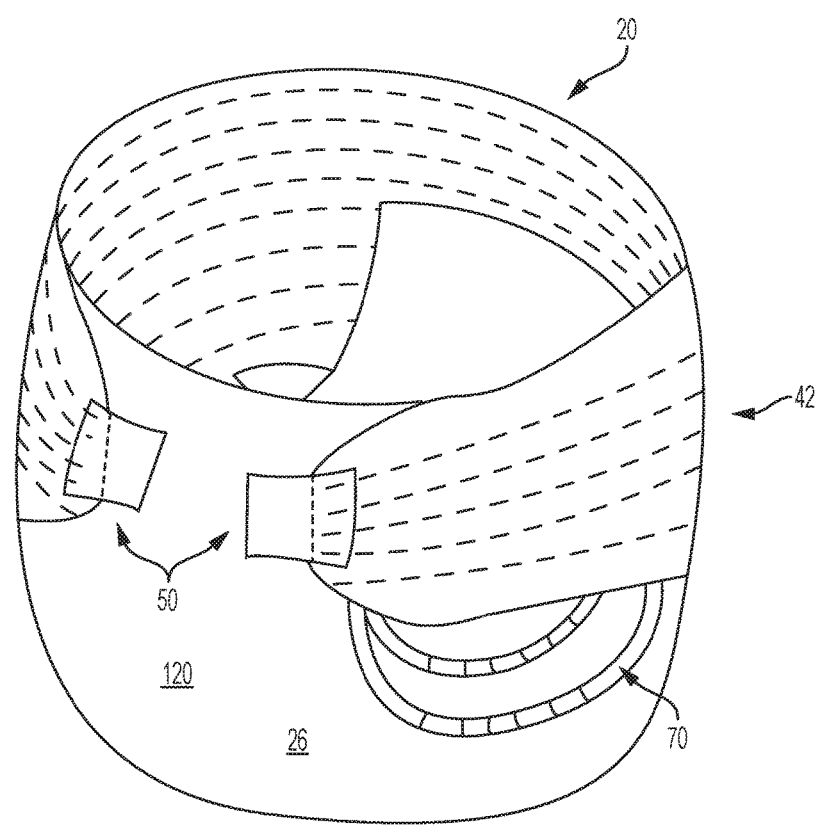
FIG. 1j is a perspective view of an exemplary taped article in a fastened configuration, disposed as it would be around a wearer, suitable in one embodiment of the invention.
Figure 1K:
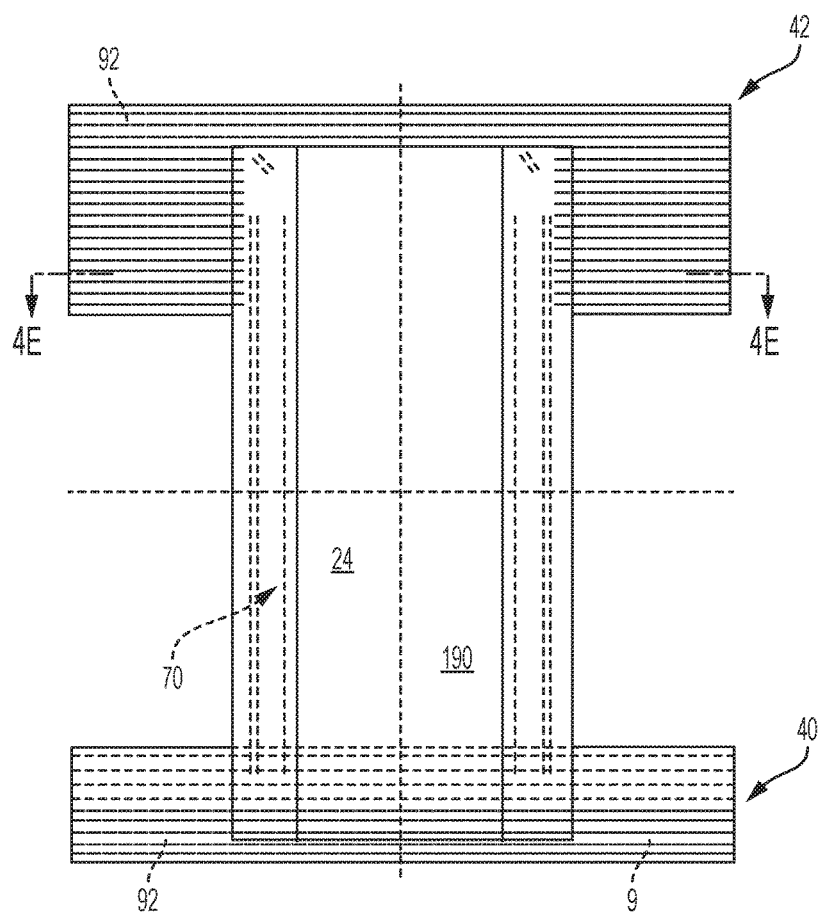
FIG. 1k is a plan view of an exemplary pant absorbent article laid out flat, suitable in one embodiment of the invention.

As shown in FIG. 1h, proximal edges of the flaps (in the front waist region and/or the back waist region) may be shaped to achieve better fit.

The flaps may be joined to the chassis via adhesive. The adhesive 170 may have a pattern as illustrated in FIG. 1i.

Flap Nonwovens

Nonwoven webs used to form the flaps can be formed by direct extrusion processes during which the fibers and webs are formed at about the same point in time, or by preformed fibers which can be laid into webs at a distinctly subsequent point in time. Example direct extrusion processes include but are not limited to: spunbonding, spunlaid, meltblowing, solvent spinning, electrospinning, carded, film fibrillated, melt-film fibrillated, air-laid, dry-laid, wet-laid staple fibers, and combinations thereof typically forming layers.

As used herein, the term "spunbonded fibers" refers to small diameter fibers, which are formed by extruding molten thermoplastic material as filaments from a plurality of fine, usually circular capillaries of a spinneret. Spunbond fibers are quenched and generally not tacky when they are deposited onto a collecting surface. Spunbond fibers are generally continuous.

As used herein, the term "meltblown fibers" means fibers formed by extruding a molten thermoplastic material through a plurality of fine, usually circular, die capillaries as molten threads or filaments into converging high velocity gas (e.g. air) streams, which attenuate the filaments of molten thermoplastic material to reduce their diameter. Thereafter, the meltblown fibers are carried by the high velocity gas stream and are deposited on a collecting surface to form a web of randomly disbursed meltblown fibers.

Example "laying" processes include wetlaying and drylaying. Example drylaying processes include but are not limited to airlaying, carding, and combinations thereof typically forming layers. Combinations of the above processes yield nonwovens commonly called hybrids or composites. Example combinations include but are not limited to spunbond-meltblown-spunbond (SMS), spunbond-carded (SC), spunbond-airlaid (SA), meltblown-airlaid (MA), and combinations thereof, typically in layers. Combinations which include direct extrusion can be combined at about the same point in time as the direct extrusion process (e.g., spinform and coform for SA and MA), or at a subsequent point in time. In the above examples, one or more individual layers can be created by each process. For instance, SMS can mean a three layer, 'sms' web, a five layer 'ssmms' web, or any reasonable variation thereof wherein the lower case letters designate individual layers and the upper case letters designate the compilation of similar, adjacent layers. The fibers in a nonwoven web are typically joined to one or more adjacent fibers at some of the overlapping junctions. This includes joining fibers within each layer and joining fibers between layers when there is more than one layer. Fibers can be joined by mechanical entanglement, by chemical bond or by combinations thereof.

In some embodiments, nonwoven fabric can be unbonded nonwoven webs, electrospun nonwoven webs, flashspun nonwoven webs (e.g., TYVEK™ by DuPont), or combinations thereof. These fabrics can comprise fibers of polyolefins such as polypropylene or polyethylene, polyesters, polyamides, polyurethanes, elastomers, rayon, cellulose, copolymers thereof, or blends thereof or mixtures thereof.

The nonwoven fabrics can also comprise fibers that are homogenous structures or comprise bicomponent structures such as sheath/core, side-by-side, islands-in-the-sea, and other bicomponent configurations. For a detailed description of some nonwovens, see "Nonwoven Fabric Primer and Reference Sampler" by E. A. Vaughn, Association of the Nonwoven Fabrics Indus-3d Edition (1992).

In some examples, suitable non-woven fiber materials may include, but are not limited to polymeric materials such as polyolefins, polyesters, polyamide, or specifically, polypropylene (PP), polyethylene (PE), poly-lactic acid (PLA), polyethylene terephthalate (PET) and/or blends thereof. In some examples, the fibers may be formed of PP/PE blends such as described in U.S. Pat. No. 5,266,392 to Land, the disclosure of which is incorporated by reference herein. Nonwoven fibers may be formed of, or may include as additives or modifiers, components such as aliphatic polyesters, thermoplastic polysaccharides, or other biopolymers. Further useful nonwovens, fiber compositions, formations of fibers and nonwovens and related methods are described in U.S. Pat. No. 6,645,569 to Cramer et al.; U.S. Pat. No. 6,863,933 to Cramer et al.; and U.S. Pat. No. 7,112,621 to Rohrbaugh et al.; and in co-pending U.S. patent application Ser. Nos. 10/338,603 and 10/338,610 by Cramer et al.; and Ser. No. 13/005,237 by Lu et al., the disclosures of which are incorporated by reference herein.

The nonwoven fabrics can include fibers or can be made from fibers that have a cross section perpendicular to the fiber longitudinal axis that is substantially non-circular. Substantially non-circular means that the ratio of the longest axis of the cross section to the shortest axis of the cross section is at least about 1.1. The ratio of the longest axis of the cross section to the shortest axis of the cross section can be about 1.1, about 1.2, about 1.5, about 2.0, about 3.0, about 6.0, about 10.0, or about 15.0. In some embodiments, this ratio can be at least about 1.2, at least about 1.5, or at least about 2.0. These ratios can be, for example, no more than about 3.0, no more than about 6.0, no more than about 10.0, or no more than about 15.0. The shape of the cross section perpendicular to the fiber longitudinal axis of the substantially non-circular fibers can be rectangular (e.g., with rounded corners) which are also referred to as "flat" fibers, trilobal, or oblong (e.g., oval) in the cross section. These substantially non-circular fibers can provide more surface area to bond to the elastomeric fiber than nonwoven fabrics with fibers that are circular in cross section. Such an increase in surface area can increase the bond strength between the elastomeric film and fibers.

Bicomponent Flap Materials

An approach to improving consumer perceptions of component materials involves forming a nonwoven web of "bicomponent" polymer fibers, by spinning such fibers, laying them to form a batt and then consolidating them by calender-bonding with a pattern, selected to provide visual effects. Such bicomponent polymer fibers may be formed by spinnerets that have two adjacent sections, that express a first polymer from one and a second polymer from the other, to form a fiber having a cross section of the first polymer in one portion and the second polymer in the other (hence the term "bicomponent"). The respective polymers may be selected so as to have differing melting temperatures and/or expansion-contraction rates. These differing attributes of the two polymers, when combined in a side by side or asymmetric sheath-core geometry, cause the bicomponent fiber products to curl in the spinning process, as they are cooled and drawn from the spinnerets. The resulting curled fibers then may be laid down in a batt and calender-bonded in a pattern. It is thought that the curl in the fibers adds loft and fluff to the web, enhancing visual and tactile softness signals.

Nonwoven webs can be made of bicomponent or multicomponent fibers. One of the components of the fibers, preferably the outer component, may be a soft polymer, such as polyethylene or elastic polyolefin, elastic polyurethane. For example, in a sheath/core bi-component fiber, the sheath can be made of polyethylene while core can be made of polypropylene. Often, the individual components comprise polyolefins such as polypropylene or polyethylene, or their copolymers, polyesters, thermoplastic polysaccharides or other biopolymers. In some embodiments, a nonwoven may be a PE/PET (polyethylene/polyethylene terephthalate) core/sheath bicomponent material, wherein the core is the PET and the outer sheath is PE.

In articles that have permanent side seams, the bicomponent material for the belt outer nonwoven can lead to a higher quality and softer seam. For example, the polyethylene of the outer sheath has a lower melting point than polypropylene of the core (or of nonwovens made completely from polypropylene). When creating the permanent side seams, other than by adhesive, but either through thermal, pressure, or ultrasonic bonding, or combinations thereof, only enough heat or pressure is required to soften or melt the polyethylene. The polyethylene of the front belt outer nonwoven, for example, can then bond with the polyethylene from the corresponding rear belt outer nonwoven. Thus, a belt made with bicomponent outer nonwoven material can require a lower bonding force to make, yet still require a high bond force to break.

The bicomponent materials also may have less adhesive bleed-through. Adhesive bleed-through is often a problem associated with the bonding of nonwovens, so materials that minimize bleed-through are advantageous, and also may allow lower basis weight nonwovens to be used, or alternatively or in conjunction, allow an increased basis weight of adhesive to be used.

Other Flap Nonwovens Materials and Treatments

Various efforts have been made to provide or alter features of nonwoven web materials with the objective of enhancing consumer perceptions of the materials. These efforts have included selection and/or manipulation of fiber chemistry, basis weight, loft, fiber density, configuration and size, tinting and/or opacifying, embossing or bonding in various patterns, etc. For example, one approach has involved simply increasing the basis weight of the web, otherwise manufactured through a spunlaid/spunbond process that includes deg. formation of a batt of loose spun fibers and then consolidating by calender-bonding in a pattern. All other variables remaining constant, increasing the basis weight of such a web will have the effect of increasing the number of fibers per unit surface area, and correspondingly, increasing apparent thickness, fiber density and/or loft.

One approach to improving consumer perception of softness of a nonwoven material is described in U.S. Pat. Nos. 5,296,289, 5,626,571, and WO9937839. It is an object of these patents to provide a nonwoven web which has been stretched to provide greater coverage with minimal sacrifices in strength as a result of stretching in the machine direction or the cross direction.

Another approach has involved subjecting the web to a hydroenhancing or hydroengorgement process following by optional calender-bonding, to fluff the fibers and increase caliper and loft. Web can be made of one layer of fiber or multi-layer of fibers. Each layer can be made of same material or different. It is believed that the hydroenhancing/ hydroengorgement process increases loft and caliper in a manner that enhances visual and tactile softness signals.

Still another approach involves changing nonwoven bond pattern to improve loft. Calendar bonding the nonwoven fibers with certain bond shape (Patent #US2014088535A1) loft of the nonwoven can be improved. Nonwoven fibers can be mono-component or bi-component.

Sleek or silky feel is often preferred over rough texture. Nonwoven silkiness is often measured using dynamic Coefficient of Friction (CoF). Silky nonowovens exhibit CoF dimensionless number between 0.2-0.5. CoF number reduces as silkiness of the material increases. Various approaches can be used to deliver silky feel. Combining loft with silky feel can improve consumer perception of nonwoven softness.

In another approach, nonwoven web can be made of mono-component fiber. However, the fiber is made of lower modulus polyolefin such as polyethylene, or polymer blend to impart silky soft feel. For example, polypropylene nonwoven can be coarse. However, when blended with elastomeric polypropylene (Vistamaxx™ from Exxon), it can help improve the feel of the fiber.

In another approach, nonwoven web can be made of elastomeric polymer. For example, elastomeric polyolefins are used in fibers spinning and to make nonwoven web. Such webs have a very sleek feel, and elastic properties, that is often desired for consumer products.

In another approach, additives can be added to polymer before spinning fiber. During fiber spinning and subsequent process steps to make the nonwoven web, the additives migrate to the fiber surface to provide a silky feel. Amine and amide based additives are commonly used up to 5%.

In another approach, a sleek chemical finish can be coated on the fibers or nonwoven webs. Chemical finishes based on oil, silicone, esters, fatty acids, surfactant etc. can be employed. Softeners such as anionic, cationic or nonionic can also be used to improve drape, and touch. Various coating techniques, like roll coating, screen coating, gravure coating, slot coating, spray coating, can be used to apply finish.

In another approach, nonwoven fiber diameter can be reduced to produce fine fibers and to provide silk like feel. Meltblown fiber is one technology to reduce fiber diameter to less than 20 microns. Alternatively, nanofibers, having a diameter of less than 1 micron, made from a melt film fibrillation process with a polymer composition disclosed in U.S. Pat. No. 8,835,709 can be used.

Drape, or the bending or pliability of material without any external force or under its own weight are other parameters that affect consumer perceptions about the material. These can be influenced by variety of factors such as fiber chemistry, thickness, nonwoven bond pattern etc. Pliability or Drape is linked to bending stiffness, which is related to inherent elastic modulus and thickness of material. It has proven to be advantageous for the nonwoven fabric to have a minimum and a maximum bending stiffness, since for instance in the use of the nonwoven fabric in contour matching, as in medical and hygiene articles, too stiff a material would be undesirable. Polyolefin resin with lower elastic modulus and/or lower crystallinity enables lower bending stiffness. One can blend lower elastic modulus materials (elastomer) with traditional fiber making polyolefin resin to make lower modulus fibers. Optimizing bonding can also alter the bending stiffness of the web in the direction desired. Bonds with larger aspect ratio of longitudinal dimension to lateral dimension provides better drape in lateral dimension while providing right rigidity and strength for web handling. Another factor affecting drape is the thickness of the web. The thicker the web is, the lower is the flexibility or pliability. Combining right thickness with fiber chemistry or bond pattern, better drape can be achieved while delivering web performance suitable for processing. The nonwoven fabric with a bending stiffness in MD direction in the range of 1-20 mm and in CD direction in the range of 1-15 mm are desired for belt making.

Nonwoven webs used to make product can often be subjected to "activation" process, either before combining with elastic or after combining. The activation or incremental stretching requires nonwoven webs to have extensibility in addition to softness. Nonwoven webs made with high melt flow rate polymers as disclosed in U.S. Pat. No. 8,926,877 or similar extensible nonwovens can be used when activation is preferred.

In some embodiments, the nonwovens may be microtextured or corrugated. Disclosure regarding the method and results of such processes may be found in U.S. filings Ser. Nos. 13/893,405, 13/893,735, and 13/893,634.

In order to enhance softness perceptions of the laminate, nonwovens may be treated by hydrojet impingement, which may also be known as hydroenhancement, hydroentanglement or hydroengorgement. Such nonwovens and processes are described in, for example, U.S. Pat. Nos. 6,632,385 and 6,803,103, and U.S. Pat. App. Pub. No. 2006/0057921, the disclosures of which are incorporated herein by reference.

Other examples of nonwoven web that may be useful in the present laminate may be an SMS web (spunbond-meltblown-spunbond web) made by Avgol Nonwovens LTD, Tel Aviv, Israel, under the designation XL-S70-26; a softband SSS (spunbond-spunbond-spunbond) web made by Pegas Nonwovens AS in Znojmo, Czech Republic, under the designation 18 XX 01 00 01 00 (where XX=the variable basis weight); an SSS web made by Gulsan Sentetik Dok San VE TIC AS, in Gaziantep, Turkey, under the designation SBXXF0YYY (where XX=the variable basis weight, and YYY=the variable cross direction width); an HESB (hydroenhanced spunbond) web made by First Quality Nonwovens Inc., in Hazelton, Pa., under the designation SEH2503XXX (where XXX=the variable cross direction width); and a bicomponent SS web.

A nonwoven web useful as a component to form one or both of layers may be pre-bonded, prior to aperturing as described below. A batt of fibers may be calendered and pre-bonded in a pattern, to consolidate the batt/fibers and create a pattern of bonds that adds tensile strength and dimensional stability, converting the batt of fibers to a coherent and useable nonwoven web material. The web may be imparted with a pattern of pre-bonding as described in, for example, U.S. Pat. No. 5,916,661 (pre-bonding in a pattern of "point calendered bonds 200 to form a coherent web structure") and co-pending U.S. application Ser. No. 13/893,405 (pattern of "primary fiber bonds"). The pre-bonding may consist of a pattern of thermal bonds, mechanical bonds or adhesive bonds, although in some circumstances thermal bonding may be preferred.

The nonwovens described herein may be used for the belt nonwovens, including for the belt outer nonwoven and/or the belt inner nonwoven. The nonwovens may also be used for other article components, such as topsheet, backsheet, wrapping layer, outer cover, or specific subcomponents, such as landing zones, flaps, etc.

Apertured Flap Nonwovens

One or more of the nonwoven layers of the belt may be apertured. Using a nonwoven web that has been apertured in the manner described below to form one or both of nonwoven web layers in a belt as described above can provide attractive and interesting effects. The apertures and the material surrounding them interact with the contraction-induced rugosities in the web layer as the belt is moved and stretched as, for example, during wear. Apertures in a layer will open, close, change shape and shift relative the other layer, providing a visual impression of complexity, depth and added texture.

An example of a process for creating apertures in a pre-bonded nonwoven web is described in U.S. Pat. Nos. 5,916,661 and 5,629,097. This process involves rolling the pre-bonded nonwoven web through the nip between a pair of rollers, one of which bears a pattern of raised bonding protrusions, and supplying heating energy to heat the fibers beneath the protrusions in the nip. When appropriately controlled pressure and heating energy are provided at the nip, a pattern of suitable bonds or "weakened, melt-stabilized locations" having rod shapes or other shapes results. At the bond sites, the polymer fibers of the web are melted, compressed and thereby fused, such that the fused polymer material at the bond sites is relatively thin (in the z-direction) and frangible. Upon subsequent cross direction incremental stretching of the bonded nonwoven web as described in the above-cited patents, the material at the bond sites or "melt-stabilized locations" breaks and apertures open in a direction transverse to the long dimension of the rod shapes. For example, a nonwoven web may be thermal/calender bonded with a bonding pattern of rod shapes having their long dimension oriented in the machine direction. Following such bonding, the web may be subjected to an incremental stretching process to stretch the web in the cross direction. When the bonding process has been appropriately controlled to create relatively thin, frangible bond sites, this causes the rod-shaped bonds to break open, creating apertures through the web. Advantageously, fibers of the nonwoven web along the edges of the apertures are fused as a result of the bonding process. In comparison to a process in which apertures are simply punched or cut through the web without application of heating energy, the bonding/stretching process described in the above-cited patent does not cut the fibers, which can result in loose fibers and fraying about the edges of the punched or cut apertures. In contrast, the bonding/stretching process described herein tends not to create loose fibers, and provides more neatly defined edges about the apertures. Following incremental stretching, the web may be allowed to relax, which may cause the apertures to close to some extent, but they will still be present. Processes for aperturing may be additionally found in U.S. filings Ser. Nos. 14/032,595 and 14/032,622.

In another example, the web may be bonded by compression bonding without the application of externally-produced or additional heating energy. Examples of suitable compression bonding systems utilizing rollers are described in, for example, U.S. Pat. Nos. 4,854,984 and 4,919,738. In these types of mechanisms, a first roller and second roller are arranged with their axes in parallel and urged together to form a nip. The first roller may have on its surface one or more bonding protrusions arranged in a pattern. The first roller and second roller may be urged together by one or more actuators such as bellows-type pneumatic actuators acting directly or indirectly on one or both of their axles, to provide and regulate compression, beneath the protrusions at the nip, of the web material as it passes therethrough, in the manner described in the aforementioned patents. A compression bonding mechanism such as, but not limited to, the mechanism described in the aforementioned patents, provides bonding of a nonwoven web material through rapid compression of superimposed fibers beneath the bonding protrusions, along the roller nip line. Without intending to be bound by theory, it is believed that rapid compression beneath the protrusions causes the respective materials to be rapidly deformed and partially expressed together from beneath the protrusions, to form structures of deformed, compressed and entangled fiber material beneath and/or around the protrusions. Welds or weld-like structures at or about the protrusions result. In some circumstances compression bonding provides advantages, including relative simplicity and cost effectiveness. It may reduce or eliminate the need for more complex bonding systems that require a system to supply externally produced or additional heating energy. Without intending to be bound by theory, it is believed that these advantages are substantially independent of variations in line speeds in at least some circumstances, including line speeds within currently known economically and technically feasible ranges for manufacture of disposable diapers and training pants. Following such creation of compression bonds, the web may be incrementally stretched to create apertures at the bond sites, in the manner taught by U.S. Pat. No. 5,916,661.

As noted, as suggested in U.S. Pat. No. 5,916,661, prior to aperturing, the nonwoven web may be pre-bonded with a relatively dense pattern of thermal/calender bonds. Following that, a pattern of apertures may simply be punched or cut through the web. A relatively dense pattern of bonding can serve to minimize loose cut fibers and fraying, and help maintain defined edges of apertures formed by cutting or punching.

It will be appreciated that the apertures created need not necessarily be rod-shaped. Other examples of shapes and patterns are described in provisional application Ser. No. 61/820,987. Also, the apertures may be rod-shaped, arc-shaped, other curved finite paths, circular, oval, elliptical or polygon, and any combinations thereof. It may be desired in some circumstances, however, that the longest dimension of a majority of the individual apertures be oriented along the machine direction of the nonwoven web—particularly when the web or components of it are formed by processes that produce a machine direction bias in the fibers such as spunbonding or spunlaying processes. (For purposes herein, "oriented along the machine direction" means that the machine direction vector component of the longest dimension of an aperture is greater than the cross direction vector component.) Because of such fiber orientation, this reduces chances that sections of fibers between adjacent apertures along the machine direction will fray or tear away. At the same time, however, while it may be desired in some circumstances that the longest dimension of a majority of the apertures be oriented along the machine direction, it may also be desired that the longest dimension is not parallel with the machine direction. In one example in which the apertures are elliptical or oval-shaped, it may be desired that their longest dimensions are oriented along angle(s) between greater than 0 and less than 45 degrees of the machine direction. It will be appreciated that this may add to visual and actual texturing effects, by causing the material along the edges of the apertures to move in a more complex manner in the machine, cross and z-directions as the belt is stretched and moved as during wear. It will also be appreciated that the apertures may be arranged in varying patterns, such as but not limited evenly-spaced and aligned rows and columns, offset rows and columns, diagonal patterns, shaped patterns, etc.

Additionally, the pattern of the apertures may be substantially similar or identical to the pattern of the pre-bonds (if present), in one or more of machine-direction spacing, cross-direction spacing, aperture shape and aperture size. For example, a pattern of pre-bonds may have substantially similar machine and cross direction spacing as the pattern of apertures. Using respective patterns of pre-bonds and apertures that are substantially similar in one or more respects noted can help give the material a more uniform, orderly and/or coherent appearance, and may also help enhance tensile strength as compared with a web in which respective patterns of pre-bonds and apertures do not have such similarities.

Using a nonwoven web that has been apertured in the manner described above to form one or both of nonwoven web layers in a belt as described above, can provide attractive and interesting effects. The apertures and the material surrounding them interact with rugosities in the web layer, providing a visual impression of complexity, depth and added texture. Apertures with various shapes, and angles relative the machine direction, can result in z-direction projections and/or ridges along the edges of the apertures when the belt structure contracts. Examples of patterns may be found in U.S. filings Ser. Nos. 14/032,595 and 14/032,622.

For example, when the belt structure contracts in either the lateral or longitudinal direction, "flaps" created by the depicted aperture shapes may stand up and add z-direction loft in addition to the height of the rugosities. The added loft may contribute to tactile and visual perceptions of added softness and/or breathability. Additionally, with expansion and contraction of the belt structure the "flaps" may open and close, alternately revealing and concealing any contrasting appearance and/or color of the underlying layer, and giving the belt structure a more complex and lively appearance.

It may be appreciated that the pattern of apertures selected may be coordinated with the pattern of adhesive selected to adhere the laminate, for varying effects. Again, see U.S. filings Ser. Nos. 14/032,595 and 14/032,622 for examples of adhesive patterns.

For example, a pattern of apertures may be selected that is somewhat independent of the pattern of rugosities created by a pattern of adhesive. The adhesive pattern may be selected so as to provide, for example, orderly machine direction rows but disordered or random cross direction columns of rugosities. The pattern of apertures may be sized and ordered so as to fall randomly on the rugosities in the machine and/or cross directions. As a result, the apertures will be positioned relative the rugosities in a somewhat random fashion, providing a particular visual effect. In another example, the pattern of adhesive may be selected to provide substantially orderly machine direction rows and cross-direction columns of rugosities. The apertures may be patterned, for example, so as to cause them to fall on the peaks of the rugosities, in, for example, substantially evenly-spaced rows and substantially evenly-distributed numbers. In this latter example, the apertures are positioned substantially at the peaks of the rugosities at a location on the nonwoven web layer at which they will experience the most movement (having another visual effect), as the belt is stretched and moved, as during wear of the article. Similarly, the apertures may be patterned in coordination with the spacing between the elastic members such as strands, such that they are substantially evenly distributed relative the locations of the strands in the belt. For example, a pattern of apertures may have an aperture spacing ASC along the cross direction that is a substantially even multiple or substantially even divisor of the elastic band spacing ESC in the cross direction in any given portion, or even the entirety, of the belt. Similarly, a pattern of apertures may have an aperture spacing ASM along the machine direction that is a substantially even multiple or substantially even divisor of the rugosity spacing RSM in the machine direction in any given portion, or even the entirety, of the belt. In one example, RSM≈ASM, so each divides into the other substantially evenly by 1. In the same example, ESC≈3 ASC, so ESC divides substantially evenly into ASC by 3. Another example may be wherein the pattern of adhesive deposits is configured to produce rugosities with peaks and valleys that are substantially continuous along the cross direction (i.e., having few or no interruptions at the elastic strands or elsewhere); this may be accomplished by a pattern of substantially continuous, linear deposits of adhesive between layers along the cross direction. The pattern of apertures may be configured such that the aperture spacing ASM along the machine direction is a substantially even multiple or substantially even divisor of the rugosity spacing RSM in the machine direction.

The visual effects of an apertured nonwoven layer in a belt may be multiplied if both layers are apertured. In the event aperturing of both layers is desired, however, it may be desirable that that the apertures of the respective layers are offset relative each other, in other words, that they do not align when the material is stretched against elastic-induced contraction to pull out the rugosities. This may be deemed important to avoid giving the belt a ragged appearance, or to avoid portions of the wearer's skin showing through the belt, or both. For this reason, it may be desired that the spacing of the aperture patterns in the respective layers differ. Alternatively, where substantially identical aperture patterns are present in both layers, it may be desired that the patterns are not in phase with each other in either or both the machine direction and cross direction, when the belt is stretched against elastic-induced contraction to pull out the rugosities.

The visual effects of an apertured nonwoven layer in a belt may be enhanced if the material of one layer has a color that visually contrasts with the color of the other layer. The material of one or both layers may be tinted, pigmented or printed in one or more colors or shades (including white) such that the colors or shades of the respective layers visually contrast. The contrasting color or shade of one layer can then be seen through apertures of the other layer for interesting visual effect. Herein, a "visual contrast" between colors or shades of two respective layers of material means that the value of delta E* determined through the Visual Contrast method, described in U.S. filings Ser. Nos. 14/032,595 and 14/032,622, is equal to or greater than 2.0. For enhanced visual contrast, it may be preferred that the value of delta E* be equal to or greater than 3.5.

Nonwoven web materials of the type typically used to form such belts are generally highly breathable. (Breathability, typically reflected in measurable vapor permeability of the material, is desired to avoid overhydration of the wearer's skin beneath the article.) Accordingly, it not necessary or desirable to provide apertures merely for the purpose of increasing breathability. Because the materials are already highly breathable aperturing may have little effect in this regard. However, it is believed that the visible presence of apertures in the material may in some circumstances give consumers the impression of high breathability, or reinforce or increase such impression—which may provide a marketing advantage for the manufacturer.

Leg Gasketing System

The absorbent article 20 may include a leg gasketing system 70. FIGS. 2 and 3 depict schematic cross section views of exemplary leg gasketing systems. The leg gasketing system 70 may comprise an inner leg cuff 71 comprising an inner cuff folded edge 72 and an inner cuff material edge 73. The leg gasketing system 70 may further comprise an outer cuff 74 comprising an outer cuff folded edge 75 and an outer cuff material edge 76.

In one embodiment, the leg gasketing system 70 may comprise only the inner leg cuff 71. In another embodiment, the outer cuffs 74 may not comprise the outer cuff folded edge 75.

The inner and outer leg cuffs may be formed by films and/or nonwovens and may be joined using adhesives (see tackdown bond 114 on FIG. 1C). In one embodiment, the leg gasketing system 70 comprises one web of material. In another embodiment, at least part of the leg gasketing system 70 may be formed with a separate web material, a part of the topsheet 24 and/or part of the backsheet 26.

In one embodiment, the outer leg cuff 74 comprises elastic members 77 positioned in a lateral array between the outer cuff folded edge 75 and outer cuff material edge 76; the outer leg cuff 74 optionally comprises at least two elastic members 77, at least three elastic member 77, at least four elastic members 77, at least five elastic members 77, at least six elastic members 77. In one embodiment, the elastic members 77 may be disposed between the outer cuff folded edge 75 and the inner cuff material edge 73.

In one embodiment, the elastic members 77 and 78 are spaced at least 2 mm apart from one edge to the other edge, optionally at least 3 mm apart; optionally at least 3.5 mm apart; optionally at least 4 mm apart. In one embodiment, the outermost elastic members 77 and 78 are less than about 2 mm from the outer cuff material edge 76 and inner cuff material edge 73; optionally less than about 1.5 mm, less than about 1 mm.

In one embodiment, the leg gasketing system 70 has an inner leg cuff 71 comprised of an inner cuff folded edge 72 and an inner cuff material edge 73. The leg gasketing system 70 may further comprise an outer cuff 74 comprising an outer cuff folded edge 75 and an outer cuff material edge 76.

The leg gasketing system may comprise a first material comprising the inner leg cuff 71 and a second material comprising the outer cuff 74. In one embodiment when there are two materials, the proximal edges of the outer cuff 74 are coterminous. In another embodiment when there are two materials, the proximal edges of the outer cuff 74 are spaced greater than about 2 mm apart; greater than about 4 mm; greater than about 6 mm; greater than about 10 mm apart. In one embodiment, the proximal material edges of the cuff are both bonded to the inner cuff. In still another embodiment when there are two materials, only one of the proximal material edges of the outer cuff 74 are bonded to the inner cuff. In one embodiment, the proximal material edges of the outer cuff are held together with any suitable bonding means. Further, the first and second material may overlap and be joined together along a longitudinal edge of each material by any suitable bonding means.

In one embodiment, the web of material is folded laterally inward to form the outer cuff folded edge 75 and folded laterally outward to form the inner cuff folded edge 72.

In one embodiment, the leg gasketing system is spaced laterally inward of the chassis edge by about 10 mm, optionally about 20 mm, optionally about 30 mm. In another embodiment, the laterally outboard edge of the chassis is defined in part by the laterally distal edge of the outer leg cuff. In another embodiment, the backsheet and polymeric film is spaced laterally inward of the outer cuff edge by about 10 mm; optionally about 20 mm; optionally about 30 mm; optionally about 40 mm.

In one embodiment, the height of the inner leg cuff 71 is at least about 30 mm, at least about 32 mm, at least about 35 mm, at least about 38 mm. In one embodiment, the height of the outer leg cuff 74 is at least about 23 mm, at least about 25 mm, at least about 27 mm, at least about 30 mm. The height of the inner cuff is measured from inner cuff folded edge to the first point of connection to a material beyond the inner cuff material edge. The outer cuff height is measured from the outer cuff folded edge to the first point of connection the inner cuff has to a material beyond the inner cuff material edge. Thus, the inner and outer cuffs are measured from their respective folded edges to the point where the inner cuff is connected to the first material beyond the inner cuff material edge.

In one embodiment of the present invention, the backsheet polymeric film is less than about 50 mm wider than the absorbent core; optionally less than about 40 mm wider, less than about 30 mm wider. In one embodiment, the backsheet polymeric film is at least about 20 mm more narrow than the chassis width (not including flaps); optionally at least about 40 mm more narrow than the chassis width; optionally at least about 60 mm more narrow than the chassis width; optionally at least about 80 mm more narrow than the chassis width; optionally at least about 100 mm more narrow than the chassis width; optionally at least about 120 mm more narrow than the chassis width. Of course In one embodiment of the present invention, the leg gasketing system is joined to the topsheet and/or backsheet by a slot coated adhesive. In one embodiment, at least about 12 gsm of adhesive is applied; optionally at least about 15 gsm of adhesive is applied; optionally at least about 20 gsm of adhesive is applied; optionally, at least about 25 gsm of adhesive is applied; optionally at least about 40 gsm of adhesive is applied; optionally at least about 60 gsm of adhesive is applied. In one embodiment, the adhesive is at least about 1 mm wide; optionally at least about 3 mm wide; optionally at least about 7 mm wide. In one embodiment, the adhesive is at least about 2 mm inboard of the outboard lateral edge of the film; optionally at least 4 mm inboard of the outboard lateral edge of the film; optionally at least about 6 mm inboard of the outboard lateral edge of the film. In one embodiment, the leg cuff is joined to the topsheet and/or backsheet by two overlapping and redundant spiral adhesive sprays; optionally three overlapping and redundant spiral adhesive sprays. In one embodiment, the leg gasketing system is joined to the topsheet and/or backsheet by a mechanical bond, a pressure bond, or an ultrasonic bond.

In one embodiment of the present invention, an opacity strengthening patch 80 may be included. Suitable strengthening patches are disclosed in U.S. Application No. 61/480,663.

In one embodiment, the material of the leg gasketing system 70 is made from a substantially liquid impervious material. The material may be selected from the group consisting of an SMS nonwoven, SMMS nonwoven material, or a nonwoven component layer comprising "N-fibers".

Various nonwoven fabric webs may comprise spunbond, meltblown, spunbond ("SMS") webs comprising outer layers of spunbond thermoplastics (e.g., polyolefins) and an interior layer of meltblown thermoplastics. In one embodiment of the present invention, the leg gasketing cuff 70 comprises a nonwoven component layer having fine fibers ("N-fibers") with an average diameter of less than 1 micron (an "N-fiber layer") may be added to, or otherwise incorporated with, other nonwoven component layers to form a nonwoven web of material. In some embodiments, the N-fiber layer may be used to produce a SNS nonwoven web or SMNS nonwoven web, for example.

The leg gasketing cuff 70 may comprise a first nonwoven component layer comprising fibers having an average diameter in the range of about 8 microns to about 30 microns, a second nonwoven component layer comprising fibers having a number-average diameter of less than about 1 micron, a mass-average diameter of less than about 1.5 microns, and a ratio of the mass-average diameter to the number-average diameter less than about 2, and a third nonwoven component layer comprising fibers having an average diameter in the range of about 8 microns to about 30 microns. The second nonwoven component layer is disposed intermediate the first nonwoven component layer and the third nonwoven component layer.

The N-fibers may be comprised of a polymer, e.g., selected from polyesters, including PET and PBT, polylactic acid (PLA), alkyds, polyolefins, including polypropylene (PP), polyethylene (PE), and polybutylene (PB), olefinic copolymers from ethylene and propylene, elastomeric polymers including thermoplastic polyurethanes (TPU) and styrenic block-copolymers (linear and radial di- and tri-block copolymers such as various types of Kraton), polystyrenes, polyamides, PHA (polyhydroxyalkanoates) and e.g. PHB (polyhydroxubutyrate), and starch-based compositions including thermoplastic starch, for example. The above polymers may be used as homopolymers, copolymers, e.g., copolymers of ethylene and propylene, blends, and alloys thereof. The N-fiber layer may be bonded to the other nonwoven component layers by any suitable bonding technique, such as the calender bond process, for example, also called thermal point bonding.

In some embodiments, the use of an N-fiber layer in a nonwoven web may provide a low surface tension barrier that is as high as other nonwoven webs that have been treated with a hydrophobic coating or a hydrophobic melt-additive, and still maintain a low basis weight (e.g., less than 15 gsm or, alternatively, less than 13 gsm). The use of the N-fiber layer may also provide a soft and breathable (i.e., air permeable) nonwoven material that, at least in some embodiments, may be used in single web layer configurations in applications which previously used double web layer configurations. Furthermore, in some embodiments, the use of the N-fiber layer may at least reduce the undesirable migration of hydrophilic surfactants toward the web and, therefore, may ultimately result in better leak protection for an associated absorbent article. Also, when compared to an SMS web having a similar basis weight, the use of a nonwoven web comprising the N-fiber layer may decrease the number of defects (i.e., holes or pinholes through the mechanical bond site) created during the mechanical bonding process. N-fibers are further discussed in WO 2005/095700 and U.S. patent application Ser. No. 13/024,844.

In one embodiment, the folded outer leg cuff web of material has a basis weight of 10 gsm; optionally 13 gsm; optionally 15 gsm; optionally 18 gsm (basis weight here is based on a single web of material).

In one embodiment, the inner leg cuff 71 web of material has an opacity of from about 15% to about 50% hunter opacity; optionally from about 20% to about 45% hunter opacity. In one embodiment, the outer leg cuff 74 web of material has an opacity of from about 45% to about 75% hunter opacity; optionally from about 50% to about 70% hunter opacity; optionally less than about 75% hunter opacity; optionally less than about 70% hunter opacity.

In one embodiment, the inner leg cuff 71 web of material has an air permeability of less than about 50 $m^3/m^2/min$; optionally less than about 45 $m^3/m^2/min$. In one embodiment, the outer leg cuff 74 web of material has an air permeability of greater than about 5 $m^3/m^2/min$; optionally greater than about 10 $m^3/m^2/min$; optionally greater than about 15 $m^3/m^2/min$; optionally greater than about 20 $m^3/m^2/min$.

The gasketing cuffs 70 may be substantially inelastic or may be elastically extensible to dynamically fit at the wearer's leg. The gasketing cuff 70 may be formed with one or more elastic members 77 and 78 (such as elastic strands) operatively joined to the topsheet 24, backsheet 26, or any other suitable substrate used in the formation of the absorbent article 20. Suitable gasketing cuff construction is further described in U.S. Pat. No. 3,860,003.

The inner leg cuff 71 may span the entire longitudinal length of the absorbent article 20. Alternatively, the inner cuff 71 may span only the entire longitudinal length of the chassis 22. The inner leg cuff 71 may be formed by a flap and an elastic member 78 (such as elastic strands). The inner leg cuff 71 may be a continuous extension of any of the existing materials or elements that form the absorbent article 20.

The inner leg cuff 71 may comprise a variety of substrates such as plastic films and woven or nonwoven webs of natural fibers (e.g., wood or cotton fibers), synthetic fibers (e.g., polyester or polypropylene fibers), or a combination of natural and synthetic fibers. In certain embodiments, the inner leg cuffs may comprise a nonwoven web such as spunbond webs, meltblown webs, carded webs, and combinations thereof (e.g., spunbond-meltblown composites and variants). Laminates of the aforementioned substrates may also be used to form the inner leg cuffs. Suitable inner leg cuffs may comprise a nonwoven available from BBA Fiberweb, Brentwood, Tenn. as supplier code 30926. Suitable elastic member is available from Invista, Wichita, Kans. as supplier code T262P. Further description of diapers having inner leg cuffs and suitable construction of such leg cuffs may be found in U.S. Pat. Nos. 4,808,178 and 4,909,803. The elastic member 78 may span the longitudinal length of the inner leg cuff 71. In other embodiments, the elastic member 78 may span at least the longitudinal length of the inner leg cuff 71 within the crotch region 37. It is desirable that the elastic member 78 exhibits sufficient elasticity such that the inner leg cuff 71 remains in contact with the wearer during normal wear, thereby enhancing the properties of the inner leg cuff 71. The elastic member 78 may be connected to the inner cuffs leg at opposing longitudinal ends. In certain embodiments, the inner leg cuffs may be folded over onto itself so as to encircle the elastic member 78.

The inner leg cuff 71 and/or outer cuff 74 may be treated, in full or in part, with a lotion, as described above with regard to topsheets, or may be fully or partially coated with a hydrophobic surface coating as detailed in U.S. application Ser. No. 11/055,743, which was filed Feb. 10, 2005. Hydrophobic surface coatings usefully herein may include a non-aqueous, solventless, multicomponent silicone composition. The silicone composition includes at least one silicone polymer and is substantially free of aminosilicones. A particularly suitable hydrophobic surface coating is available from Dow Corning MI, Salzburg as supplier code 0010024820.

Absorbent Core

Figure 7:
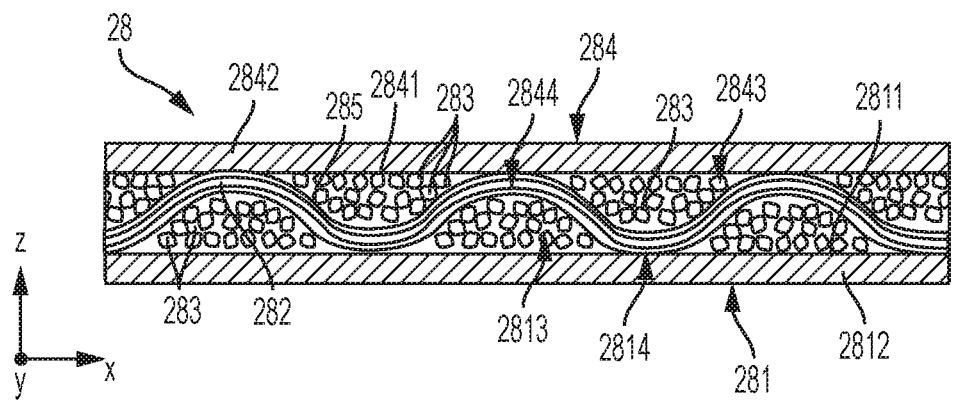
FIG. 7 is a schematic cross section view of another example of an absorbent core suitable in one embodiment of the invention.

In one embodiment, an absorbent article includes an absorbent core 28 that is substantially cellulose free. Cross-sectional views of examples of suitable absorbent cores are schematically represented in FIGS. 5-7. The absorbent core

28 is the element of the absorbent article whose primary function is to absorb and retain liquid body exudates. Additional elements may be added between the topsheet and the absorbent core of an absorbent article to facilitate the acquisition and the distribution of body exudates. Such elements may include, for example, an acquisition layer 96 (see FIG. 4a) and/or a distribution layer as it is well known in the art. The acquisition and/or distribution layers may themselves be substantially cellulose free (for example made entirely of a nonwoven material) or include a significant amount of cellulosic material. Although an absorbent core generally includes absorbent materials in particulate form having a high retention capacity such as, for example absorbent polymers, these materials do not need to be present along the entire length of the absorbent core. It may be advantageous to provide an absorbent core with a greater amount of absorbent material in the crotch area and/or the front waist region in comparison to the rear waist region which may include only a little amount, if any, of absorbent polymers. In one embodiment, an absorbent core 28 comprises first and second layers of material 281, 282 and an absorbent material 283 disposed between the first and second layers 281, 282. In one embodiment the first and second layers of material can be a fibrous material chosen from at least one of a nonwoven fibrous web, a woven fibrous web and a layer of thermoplastic adhesive material. Although the first and second layers can be made of a same material, in one embodiment, the first layer 281 is a nonwoven fibrous web and the second layer 282 is a layer of thermoplastic adhesive material. A nonwoven fibrous web 281 can include synthetic fibers, such as mono-constituent fibers of PE, PET and PP, multi-constituent fibers such as side by side, core/sheath or island in the sea type fibers. Such synthetic fibers may be formed via a spunbonding process or a meltblowing process. The nonwoven fibrous web 281 may include a single layer of fibers but it may also be advantageous to provide the nonwoven web with multiple layers of fibers such as multiple layers of spunbond fibers, multiple layers of meltblown fibers or combinations of individual layer(s) of spunbond and meltblow fibers. In one embodiment, the nonwoven web 281 can be treated with an agent (such as a surfactant) to increase the surface energy of the fibers of the web. Such an agent renders the nonwoven web more permeable to liquids such as urine. In another embodiment, the nonwoven web can be treated with an agent (such as a silicone) that lowers the surface energy of the fibers of the nonwoven web. Such an agent renders the nonwoven web less permeable to liquids such as urine.

The first layer 281 comprises a first surface 2811 and a second surface 2812 and at least regions 2813 of the first surface are in direct facial relationship with a significant amount of absorbent material 283. In one embodiment an absorbent material is deposited on the first surface 2811 in a pattern to form regions 2813 on the first layer 281, which are in direct facial relationship with a significant amount of absorbent polymer material 283 and regions 2814 on the first web that are in facial relationship with only an insignificant amount of absorbent material. By "direct facial relationship with a significant amount of absorbent material" it is meant that some absorbent material is deposited on top of the regions 2813 at a basis weight of at least 100 g/m$^2$, at least 250 g/m$^2$ or even at least 500 g/m$^2$. The pattern may include regions that all have the same shape and dimensions (i.e. projected surface area and/or height). In the alternative the pattern may include regions that have different shape or dimensions to form a gradient of regions. At least some of the regions 2813 can have a projected surface area of between 1 cm$^2$ and 150 cm$^2$ or even between 5 cm$^2$ and 100 cm$^2$. By "facial relationship with an insignificant amount of absorbent material" it is meant that some absorbent material may be deposited on top of the regions 2814 at a basis weight of less than 100 g/m$^2$, less than 50 g/m$^2$ or even substantially no absorbent material. At least some of the regions 2814 can have a projected surface area of between 1 cm$^2$ and 150 cm$^2$ or even between 5 cm$^2$ and 100 cm$^2$. The aggregate projected surface area of all the regions 2813 can represent between 10% and 90% or even between 25% and 75% of the total projected surface area of the first surface 2811 of the first layer 281. In one embodiment, the second layer 282 is a layer of a thermoplastic adhesive material. "Thermoplastic adhesive material" as used herein is understood to mean a polymer composition from which fibers are formed and applied to the absorbent material with the intent to immobilize the absorbent material in both the dry and wet state. Non-limiting examples of thermoplastic adhesive material may comprise a single thermoplastic polymer or a blend of thermoplastic polymers. The thermoplastic adhesive material may also be a hot melt adhesive comprising at least one thermoplastic polymer in combination with other thermoplastic diluents such as tackifying resins, plasticizers and additives such as antioxidants. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are polymers prepared using single-site or metallocene catalysts. In exemplary embodiments, the tackifying resin has typically a Mw below 5,000 and a Tg usually above room temperature, typical concentrations of the resin in a hot melt are in the range of about 30 to about 60% by weight, and the plasticizer has a low Mw of typically less than 1,000 and a Tg below room temperature, with a typical concentration of about 0 to about 15%.

The thermoplastic adhesive material 282 can be disposed substantially uniformly within the absorbent material 283. In the alternative, the thermoplastic adhesive material 282 can be provided as a fibrous layer disposed on top of the absorbent material 283 and the regions 2814 of the first surface 2811 that are in facial relationship with only an insignificant amount of absorbent material. In one embodiment, a thermoplastic adhesive material is applied at an amount of between 1 and 20 g/m$^2$, between 1 and 15 g/m$^2$ or even between 2 and 8 g/m$^2$. The discontinuous deposition of absorbent material on the first layer 281 imparts an essentially three-dimensional structure to the fibrous layer of thermoplastic material 282. In other words, the layer of thermoplastic adhesive material follows the topography resulting from the absorbent material 283 deposited on the first nonwoven fibrous web 281 and the regions 2814 that only include insignificant amounts of absorbent material. Without intending to be bound by any theory, it is believed that the thermoplastic adhesive materials disclosed herein enhance immobilization of the absorbent material in a dry and wet state.

In one embodiment, the absorbent core 28 may further comprise a second layer of a nonwoven fibrous material 284. This second layer may be provided of the same material as the nonwoven fibrous layer 281, or in the alternative may be provided from a different material. It may be advantageous for the first and second nonwoven fibrous layers 281, 284 to be different in order to provide these layers with different functionalities. In one embodiment, the surface energy of the first nonwoven layer can be different than the surface energy of the second nonwoven layer. In one embodiment, the surface energy of the second nonwoven layer is greater than the surface energy of the first nonwoven layer. Among over benefits, it is believed that when the surface energy of the second nonwoven layer is greater than the surface energy of the first nonwoven layer, liquids such as urine will be able to penetrate the second nonwoven layer more easily in order to reach and be retained by the absorbent material while at the same time reducing the chances that the liquid may penetrate and go through the first layer. This may be particularly advantageous when the first nonwoven layer is disposed against the backsheet of an absorbent article. The different surface energies of each layer may be obtained, for example, by applying a different amount of an agent such as a surfactant to the second nonwoven layer than the amount of surfactant (if any) applied to the first nonwoven layer. This may also be achieved by applying a different type of surfactant to the second nonwoven layer than the surfactant applied to the first nonwoven layer. This may still be achieved by applying a material to the first nonwoven layer that lowers its surface energy. In addition to having different surface energies, or in the alternative, the first and second nonwoven fibrous layers 281, 284 may also be different structurally. In one embodiment, the first nonwoven layer 281 may include different layers of fibers than the second nonwoven layer. For example, the second nonwoven layer 284 may only include one or more layers of spunbond fibers whereas the first nonwoven layer 281 includes one or more layers of spundbond fibers and one or more layers of meltblown fibers. In another embodiment, both nonwoven fibrous layers 281, 284 may include one or more layers of spunbond fibers and one or more layers of meltblown fibers but the first and second layers 281, 284 differ in terms of at least one of the chemical composition of the fibers used to form the nonwoven material, the denier of the fibers and/or the basis weight of the nonwoven material. In addition to or in the alternative than the above the first and second nonwoven layers 281, 284 may also differ in terms of at least one of their respective hydrohead values, their respective porosity, their respective Frazier permeability and their respective tensile properties. The second nonwoven layer 284 may applied directly on top of the first nonwoven layer 281, the absorbent material 283 and the thermoplastic adhesive material 282. As a result, the first and second nonwoven layers 281 and 284 further encapsulate and immobilize the absorbent material 283.

The regions 2813 may have any suitable shape in the x-y dimension of the absorbent core. In one embodiment, the regions 2813 form a pattern of disc that are spread on the first surface of the first web 281. In one embodiment, the regions 2813 form a pattern of longitudinal "strips" that extend continuously along the longitudinal axis of the absorbent core (i.e. along the y dimension). In an alternative embodiment, these strips may be are arranged to form an angle of at between 10 and 90 degrees, between 20 and 80 degrees, between 30 and 60 degrees, or even 45 degrees relative to the longitudinal axis of the absorbent article.

In one embodiment, the second nonwoven layer 284 has a first surface 2841 and a second surface 2842 and an absorbent material 283 applied to its first surface 2841 in order to form a pattern of regions 2843 that are in direct facial relationship with a significant amount of absorbent material 283 and regions 2844 on the first surface 2841 that are in facial relationship with only an insignificant amount of absorbent material as previously discussed. In one embodiment, a thermoplastic adhesive material 285 may further be applied on top of the second nonwoven layer 284 as previously discussed in the context of the first web/absorbent material/thermoplastic adhesive material composite. The second nonwoven layer 284 may then be applied on top of the first nonwoven layer 281. In one embodiment, the pattern of absorbent material present on the second nonwoven layer 284 may be the same as the pattern of absorbent material present on the first nonwoven layer 281. In another embodiment, the patterns of absorbent material that are present on the first and second nonwoven layers are different in terms of at least one of the shape of the regions, the projected surface areas of the regions, the amount of absorbent material present on the regions and the type of absorbent material present on the regions. It is believed that when the patterns of absorbent material that are present on the first and second nonwoven layers are different, each layer/absorbent composite may have different functionalities such as for example, different absorbent capacities and/or different acquisition rates of liquids. It can be beneficial for example to provide an absorbent core with a structure where the second pattern formed by the regions 2843 of absorbent material (i.e. on the second nonwoven layer 284) exhibits a slower acquisition rate than the first pattern of regions 2813 of absorbent material in order to allow liquids, such as urine, to reach and be absorbed by the absorbent material deposited on the first nonwoven layer 281 before expansion of the absorbent material in the regions 2843. Such a structure avoids any significant gel blocking by the absorbent material present in the regions 2843. It can also be advantageous to apply the second layer/absorbent material/thermoplastic adhesive material composite in such a way that at least some of or even all of the regions 2813 of the first nonwoven layer 281 that are in direct facial relationship with a significant amount of absorbent material are also in substantial facial relationship with corresponding regions 2844 of the second web 284, which are in facial relationship with an insignificant amount of absorbent material.

The absorbent core 28 may also comprise an auxiliary adhesive which is not illustrated in the figures. The auxiliary adhesive may be deposited on at least one of or even both the first and second nonwoven layers 281, 284 before application of the absorbent material 283 in order to enhance adhesion of the absorbent material as well as adhesion of the thermoplastic adhesive material 282, 285 to the respective nonwoven layers 281, 284. The auxiliary adhesive may also aid in immobilizing the absorbent material and may comprise the same thermoplastic adhesive material as described hereinabove or may also comprise other adhesives including but not limited to sprayable hot melt adhesives, such as H.B. Fuller Co. (St. Paul, Minn.) Product No. HL-1620-B. The auxiliary adhesive may be applied to the nonwoven layers 281, 284 by any suitable means, but according to certain embodiments, may be applied in about 0.5 to about 1 mm wide slots spaced about 0.5 to about 2 mm apart. Non-limiting examples of suitable absorbent material 283 include absorbent polymer material such as cross linked polymeric materials that can absorb at least 5 times their weight of an aqueous 0.9% saline solution as measured using the Centrifuge Retention Capacity test (Edana 441.2-01). In one embodiment, the absorbent material 283 is absorbent polymer material which is in particulate form so as to be flowable in the dry state.

As previously discussed, the absorbent material 283 present in the absorbent cores 28 of an absorbent article, does not need to be present along the entire length of the absorbent core. In one embodiment, the back section 328 of an absorbent article includes an insignificant amount of absorbent material 283 whereas at least the middle 228 and/or the front section 128 include a greater amount of absorbent material than the back section 328. For example, the back section 328 may include less than 5 grams, or less than 3 grams, less than 2 grams or even less than 1 g of a particulate absorbent polymer material. The middle section 228 may include at least 5 grams, or at least 8 grams, or even at least 10 grams of a particulate absorbent polymer material. The front section 128 may include between 1 and 10 grams, or between 2 and 8 grams of a particulate absorbent polymer material.

Flaps

The flaps 40, 42 may be discrete from or integral with the chassis. A discrete flap is formed as separate element which is joined to the chassis 22. In some embodiments, this includes a plurality of flaps, e.g. 2 or 4 (often referred to as ear panels or side flaps) being joined to the side edges of the chassis in the front and/or rear waist regions (see FIGS. 1a and 1b). In other embodiments this may include a front and/or back belt-like flaps being joined across the front and back (or rear) waist regions of the chassis, at least across end edges of the chassis (see FIGS. 1c, 1f-1k, 4a-4e).

Figure 8:
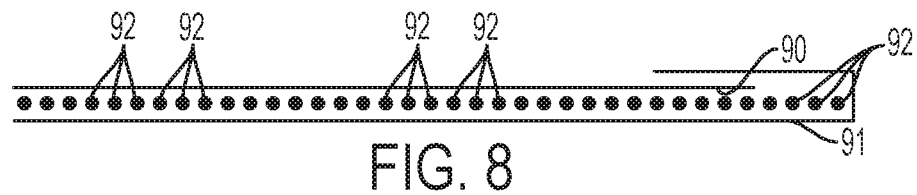
FIG. 8 is a schematic cross section view of a back belt-like flap suitable in one embodiment of the invention, taken along 8-8 of FIG. 1c.
Figure 9:
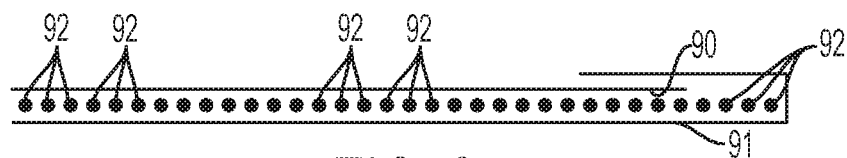
FIG. 9 is a schematic cross section view of a front belt-like flap suitable in one embodiment of the invention, taken along 9-9 of FIG. 1c.
Figure 10:
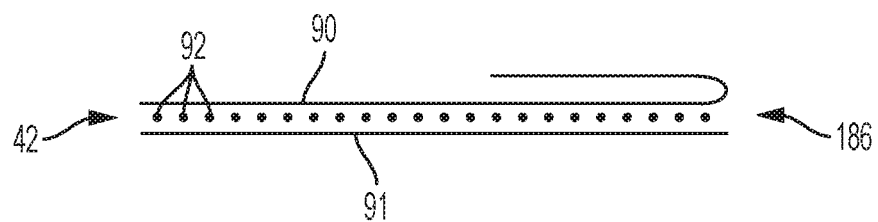
FIG. 10 is a schematic cross section view of a front belt-like flap suitable in one embodiment of the invention, taken along 8-8 of FIG. 1c.

Referring to FIG. 8, the belt-like flaps 40 and 42 may comprise an inner nonwoven layer 90 and an outer nonwoven layer 91 and elastics 92 therebetween. The inner and outer nonwoven layers may be joined using adhesive or thermoplastic bonds. Various suitable belt-like flap configurations can be found in U.S. App. No. 61/598,012, filed on Feb. 13, 2012, titled DISPOSABLE PULL-ON GARMENT, by the Procter & Gamble Company.

An integral flap is a portion, one or more layers, of the chassis 22 that projects laterally outward from the longitudinal edge 12. The integral flap may be formed by cutting the chassis to include the shape of the flap projection.

While many of the embodiments illustrated in this application having belt-like flaps are pant articles, taped articles may have belt-like flaps disposed in one or both waist regions as well.

Fastening System

The absorbent article 20 may also include a fastening system 50. When fastened, the fastening system 50 interconnects the front waist region 36 and the rear waist region 38 resulting in a waist circumference that may encircle the wearer during wear of the absorbent article 20. This may be accomplished by flaps in the back waist region interconnecting with flaps in the front waist region or by flaps in the back waist region interconnecting with the chassis in the front waist region. The fastening system 50 may comprises a fastener such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 50 may also provide a means for holding the article in a disposal configuration as disclosed in U.S. Pat. No. 4,963,140. The fastening system 50 may also include primary and secondary fastening systems, as disclosed in U.S. Pat. No. 4,699,622. The fastening system 50 may be constructed to reduce shifting of overlapped portions or to improve fit as disclosed in U.S. Pat. Nos. 5,242,436; 5,499,978; 5,507,736; and 5,591,152.

The belt flaps may comprise fasteners designed to refastenably engage a landing zone area of the chassis, as well as refastenably engage a landing zone area on an exterior area of the belt flap, such that the belt flap overlaps itself to better swaddle the wearer—exemplary embodiments of this configuration are disclosed in U.S. Pat. No. 9,408,758.

The fasteners on taped articles may be folded to keep the engaging material (e.g., hooks, adhesive, etc.) from engaging an unintended portion of the article. When folded, the engaging material may contact a non-engagement surface such as a film, a polymer layer, or a non-tacky adhesive layer. When taken out of the package, the fastener may be unfolded and engaged with a landing zone (often in the front region of the chassis). Fasteners on taped articles are often transversely oriented.

Fasteners on pant articles are often longitudinally oriented. Fasteners on pant articles may be disposed on a front belt, which is designed to engage the back belt or may be disposed on a back belt, which is designed to engage the front belt, resulting in an overlapping seam. The engaging material may be disposed on a garment-facing surface, designed to engage a wearer-facing surface, so that the engaging material is not oriented toward the wearer, thus avoiding possible irritation to the wearer's skin.

CROSS SECTION EMBODIMENTS

One way to compare product chassis is to analyze the cross section of the products in the front waist region, rear waist region and crotch region. Particularly, it may be useful to look at the cross sectional order of components and disposition of the components. For example, referring to FIG. 4a, one embodiment of the chassis has a layered configuration comprising a backsheet 26 disposed on the garment side of the chassis 22, the backsheet 26 comprising a nonwoven garment-facing layer 26b and a film layer 26a disposed inwardly of the nonwoven garment-facing layer 26b. The chassis 22 further comprises an absorbent core 28 disposed inwardly of the backsheet 26, a topsheet 24 disposed inwardly of the absorbent core 28 and laterally opposing inner leg cuffs 71 having at least a portion of the leg cuff disposed inwardly of the topsheet 24. The inner leg cuff 71 comprising inner leg elastics 78 disposed laterally inward of at least one of the side edges of the backsheet 26 and the side edges of the topsheet 24 and/or the side edges of the absorbent core 28. The article 20 further comprising outer leg cuffs 74 wherein at least a portion of the outer leg cuff 74 is disposed laterally outward of the side edge of the topsheet 24. The outer leg cuff 74 having a portion of the leg gasketing system 70 disposed laterally outward of the side edge of the backsheet film 26a. The outer leg cuff 74 further comprises elastics 77 disposed laterally outward of at least one of the topsheet 24 and backsheet film 26a. Furthermore, the topsheet 24, backsheet 26, and leg gasketing system 70 of this embodiment have the same longitudinal extent and extend from a first end edge of the chassis 20 in the front waist region 36 to a second end edge of the chassis 22 in the rear waist region 38. The absorbent article 20 of this embodiment also comprises at least one flap 42 wherein the flap 42 comprises laterally opposing flap portions disposed outwardly of the side edges of the chassis 22 and a laterally extending waistband portion 112 of the flap 42 disposed adjacent the waist edge 111 of the flap 42 and longitudinally outward of the chassis 22.

Figure 4B:
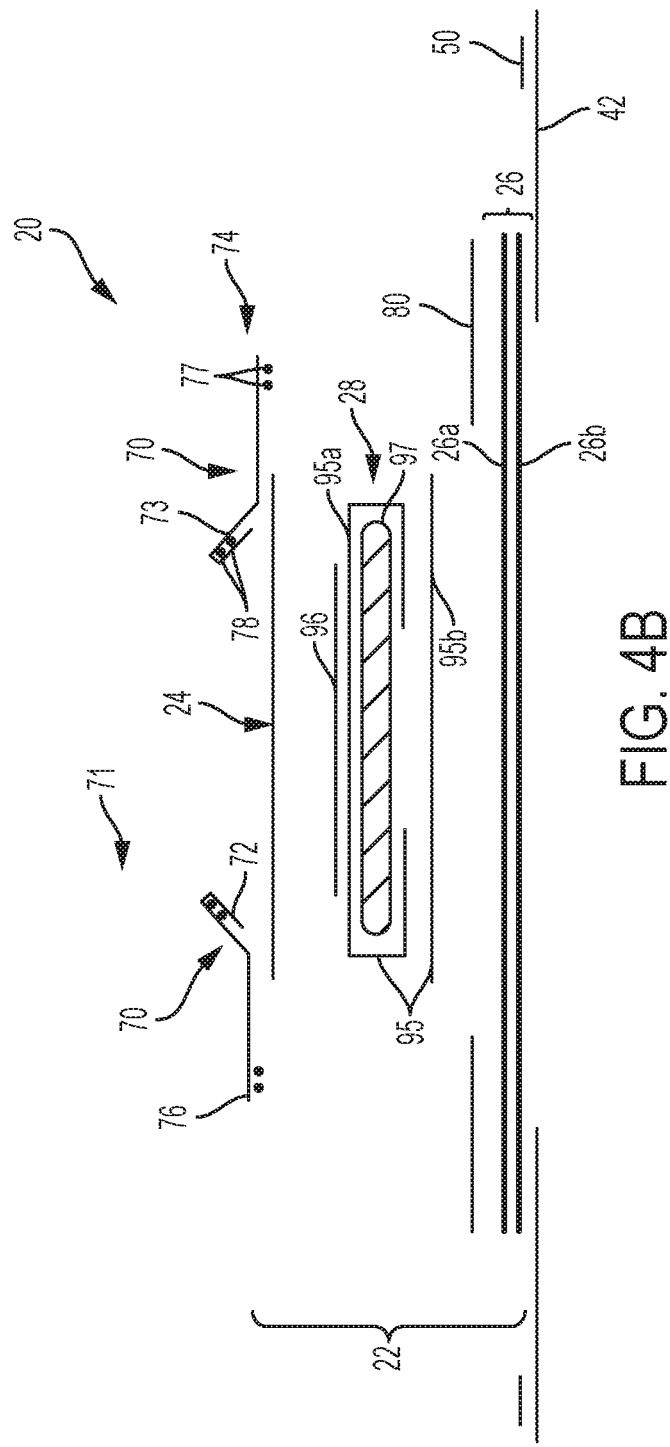
FIG. 4b is a schematic cross section view of an exemplary absorbent article, suitable in one embodiment of the invention.

Referring to FIG. 4b, the cross sectional order of components and disposition of the components of the chassis 22 is the same except for the disposition of the leg gasketing system 70.

Figure 4C:
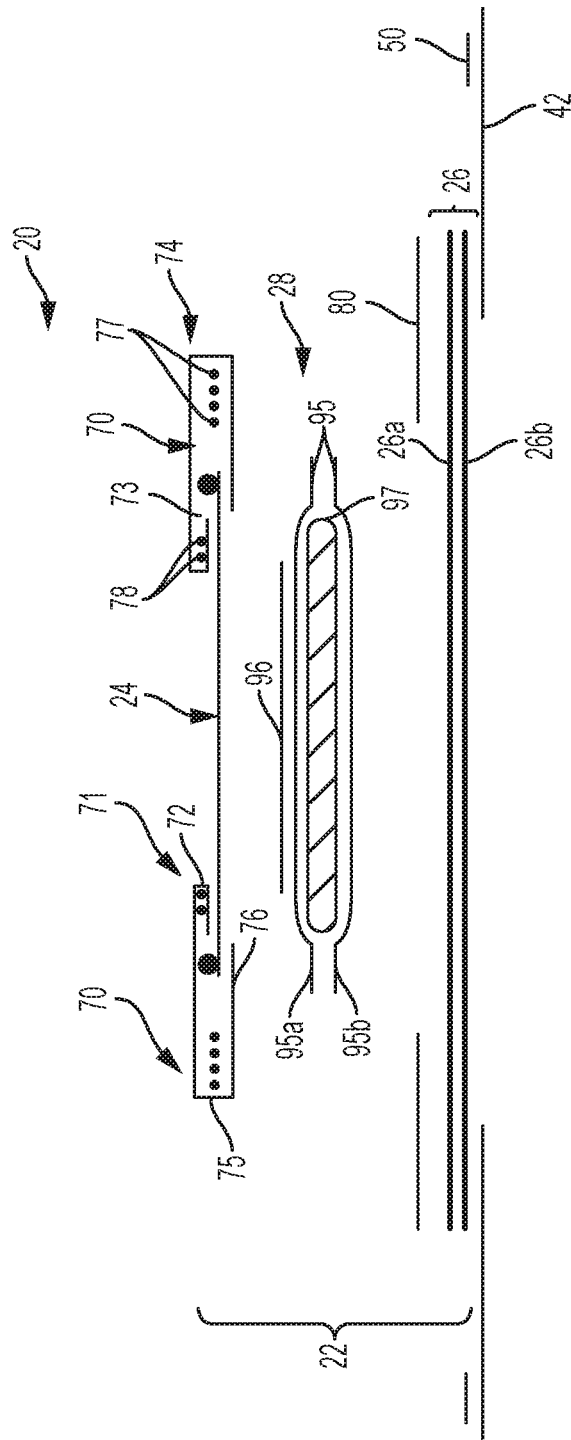
FIG. 4c is a schematic cross section view of an exemplary absorbent article, suitable in one embodiment of the invention.
Figure 4D:
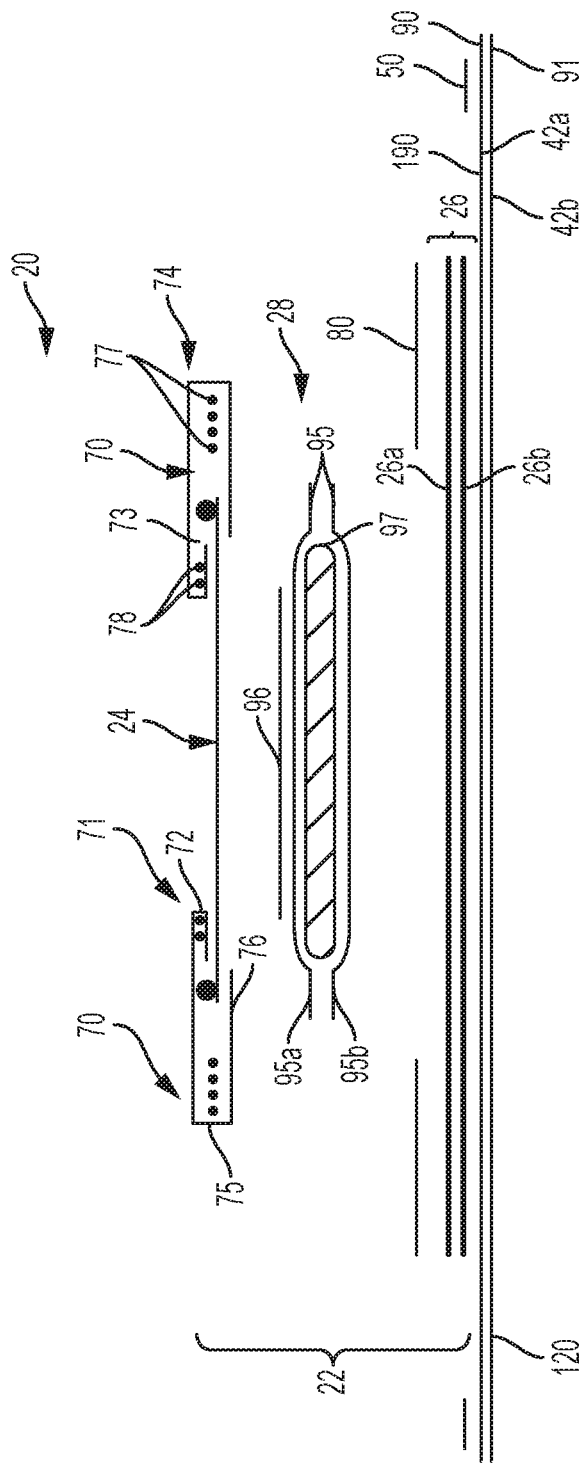
FIG. 4d is a schematic cross section view taken along 4d-4d of FIG. 1g, illustrating one suitable embodiment of the present disclosure.
Figure 4E:
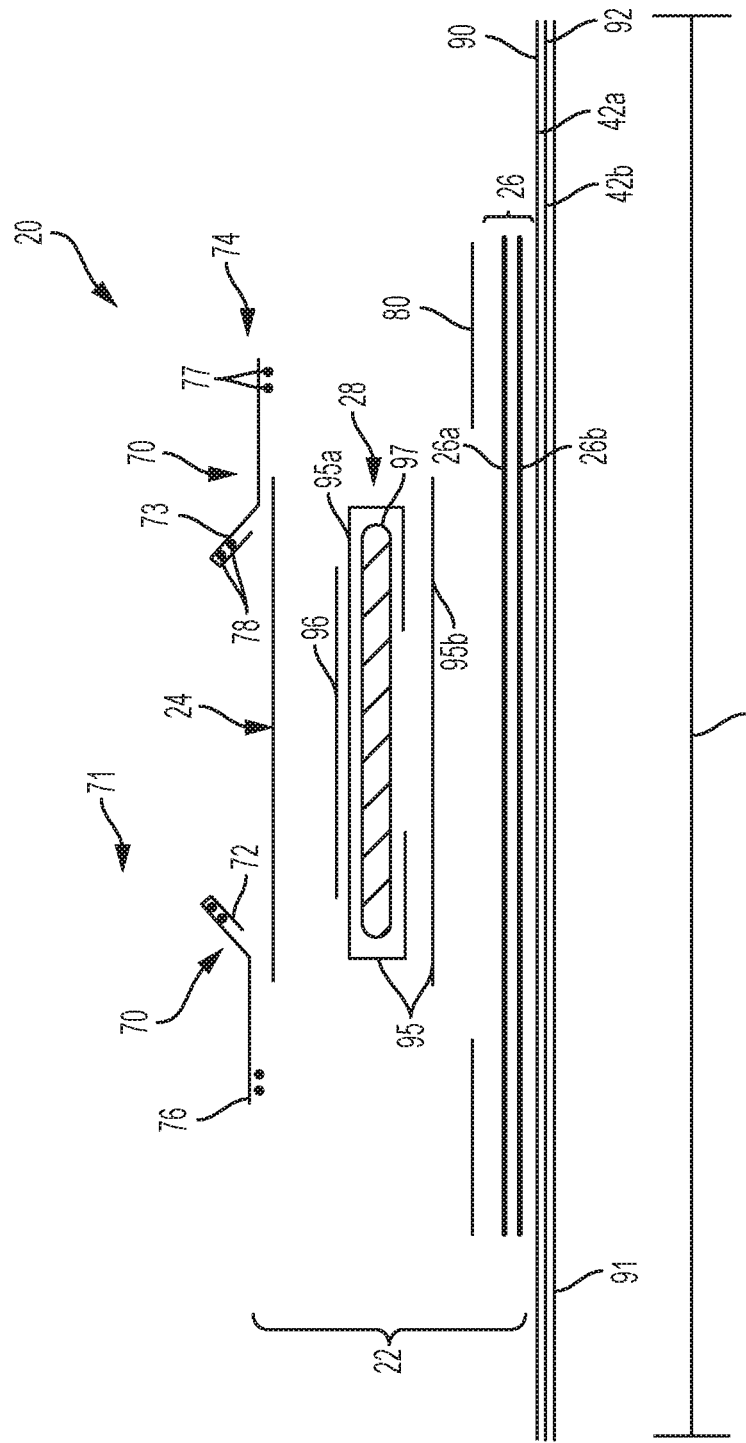
FIG. 4e is a schematic cross section view taken along 4e-4e of FIG. 1k, illustrating one suitable embodiment of the present disclosure.

Referring to FIG. 4c, the cross sectional order of components and disposition of the components of the chassis 22 is the same except for the disposition of the core 28 and core wrap 95.

In another embodiment, the chassis 22 may comprise a waistband material disposed inwardly (on the body-facing side) of the backsheet.

For clarity, two embodiments that are identical to FIG. 4a that have different dispersions or patterns of SAP within the core would still be considered to have identical cross sectional order of components and disposition of the components in at least one cross section.

With regard to disposition of the components, it may be desirable to compare key distances between components. Particularly, it may be desirable to measure and compare one or more of the following:

The distance from a left outer cuff distal edge to a right outer cuff distal edge (FIG. 4a-Distance a)
The distance from a left inner cuff proximal edge to a left outer cuff distal edge (FIG. 4a-Distance b)
The distance from a left inner cuff proximal edge to a right inner cuff proximal edge (FIG. 4a-Distance c)
The distance of the free height of the inner cuff (FIG. 4a-Distance d)
Inner cuff hem fold width (FIG. 4a-Distance e)
Inner cuff elastics length (FIG. 1a-Distance f)
Outer cuff elastics length (FIG. 1a-Distance g)
core length (FIG. 1c-Distance h)
backsheet width (FIG. 4a-Distance i)
core width (FIG. 4a-Distance j)
tackdown length (FIG. 1c-Distance k)
topsheet width
backsheet length
topsheet length Additionally, beyond comparing chassis, it may be desirable to compare the flap of a taped article to the flap of a pant article. More specifically, it may be desirable to compare the following aspects of the flaps: flap nonwoven and elastic dimension (e.g., length and width), flap nonwoven and elastic material composition, flap nonwoven and elastic disposition (e.g., folds, overlaps, etc.), flap nonwoven basis weight, flap elastics form (e.g., film, strands, bands, etc), flap elastic properties, flap glue patterns and glue basis weights.

With regard to disposition of the flaps, and components thereof, it may be desirable to compare key distances between components. Particularly, it may be desirable to measure and compare one or more of the following:

The longitudinal distance of a flap (FIGS. 2 and 9—Distance m)
The transverse distance of a flap (FIG. 2—Distance n)
The longitudinal distance between the end edge of the chassis and the end edge of the flap (FIG. 2—Distance o)
The longitudinal distance between the end edge of the chassis and the proximal edge of the flap (FIG. 2—Distance p)
The longitudinal distance between the end edges of the flap-to-chassis glue pattern (FIG. 3—Distance q)
The transverse distance between the side edges of the flap-to-chassis glue pattern (FIG. 3—Distance r)

For measurements of 100 mm or less, non-identical lengths within 5% of each other and widths within 10% of each other, including, but not limited to the distances above, may be considered to be substantially identical distances. For measurements greater than 100 mm, non-identical lengths within 2% of each other and widths within 5% of each other, including, but not limited to the distances above, may be considered to be substantially identical distances.

Process for Making Absorbent Articles

It may be desirable to utilize the chassis and flaps made on the same converting line in the same manufacturing facility using identical or substantially identical chassis and flap materials for both taped and pant absorbent articles. Alternatively, it may be desirable to utilize the chassis and flaps made on the same converting line type (referring specifically to the portion of the line that makes the chassis) in different manufacturing facilities using identical or substantially identical chassis and flap materials for both taped and pant absorbent articles.

It may be desirable to utilize the chassis and flaps made on different converting lines that use identical or substantially identical chassis and flap materials and chassis and flap converting processes for both taped and pant absorbent articles. These lines may be in the same or different locations.

U.S. Pub. No. 2011-0247199, U.S. patent application Ser. No. 13/074,048, and U.S. No. 13/371,919, filed on Feb. 13, 2012, titled CONVERTING LINES AND METHODS FOR FABRICATING BOTH TAPED AND PANT DIAPERS COMPRISING SUBSTANTIALLY IDENTICAL CHASSIS, by the Procter & Gamble Company disclose suitable converting lines capable of producing taped and pant articles of the current disclosure. These converting lines utilize a substantial number of the same processes and machinery to produce both taped and pant articles having the same or similar chassis.

Display of Absorbent Articles

There are a number of configurations for displaying the taped and pant absorbent articles of the present disclosure that may be desirable. In one embodiment, taped and pant absorbent articles from the same manufacturer may have identical or substantially identical chassis and flaps. It should be understood that the same manufacturer includes contract manufacturers making for or on behalf of another entity. Further, the identical or substantially identical chassis and flaps may be for the same size taped and pant articles or the identical or substantially identical chassis and flaps may be for different sized taped and pant absorbent articles.

Still further, it may be desirable to display identical or substantially identical chassis and flaps for the same size taped and pant articles up to a particular size (e.g., size 3) and then to use a taped size 3 chassis and flaps for pant size 4, and a taped size 4 chassis and flaps for a pant size 5, and a taped size 5 chassis and flaps for a pant size 6, and so on. The reason for offsetting sizes may be due to core capacity needs between taped and pant article wearers. Additionally, it may be due to the different flap configurations/orientations between pant and taped articles. Articles comprising full belts (e.g., the article of FIG. 1C) may need shorter chassis than the same sized article comprising discrete elastomeric flaps (e.g., the article of FIG. 1B).

It should be understood that size 1 in North America (NA) correlates to size Newborn (NB) in Asia, size 2 in NA correlates to size Small (S) in Asia, size 3 in NA correlates to size Medium (M) in Asia, size 4 in NA correlates to size Large (L) in Asia, and size 5 in NA correlates to size Extra-Large (XL) in Asia.

The sizes of the articles may be displayed on the packages comprising the articles and/or may be displayed on the articles themselves, via indicia. Further, instead of or in combination with the size indicia, the packages and/or articles may comprise weight ranges of the prospective wearers. There may be weight range overlap between taped and pant articles of different sizes or between taped articles of different sizes or overlap between pant articles of different sizes. Further, there may be indicia of article components or features and/or representative wearers using the article in an appropriate manner for the stage of development of that wearer. The package may comprise indicia illustrating a wearer with or without an apparent caregiver. The indicia may illustrate the wearer wearing the article and/or a separate indicia may illustrate the article component of feature. Descriptions of suitable stages of development indicia and methods of displaying packages comprising absorbent articles may be found in U.S. Pat. No. 7,222,732 to Ronn, titled MERCHANDISE DISPLAY SYSTEM FOR IDENTIFYING DISPOSABLE ABSORBENT ARTICLE CONFIGURATIONS FOR WEARERS.

Further, it is foreseen that identical or substantially identical chassis and flaps for infant, newborn, or toddler taped or pant articles may be used for adult absorbent articles (including adult diapers and inserts). For instance, a larger sized toddler diaper chassis and flaps (e.g., size 6) may be used for a small or medium sized adult diaper. Still further an infant, newborn, or toddler chassis and flaps may be used as an insert for adult incontinence products.

Packages

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 100 mm, less than about 95 mm, less than about 90 mm, less than about 85 mm, less than about 85 mm, but greater than about 75 mm, less than about 80 mm, less than about 78 mm, less than about 76 mm, or less than about 74 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 95 mm, from about 72 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 13:
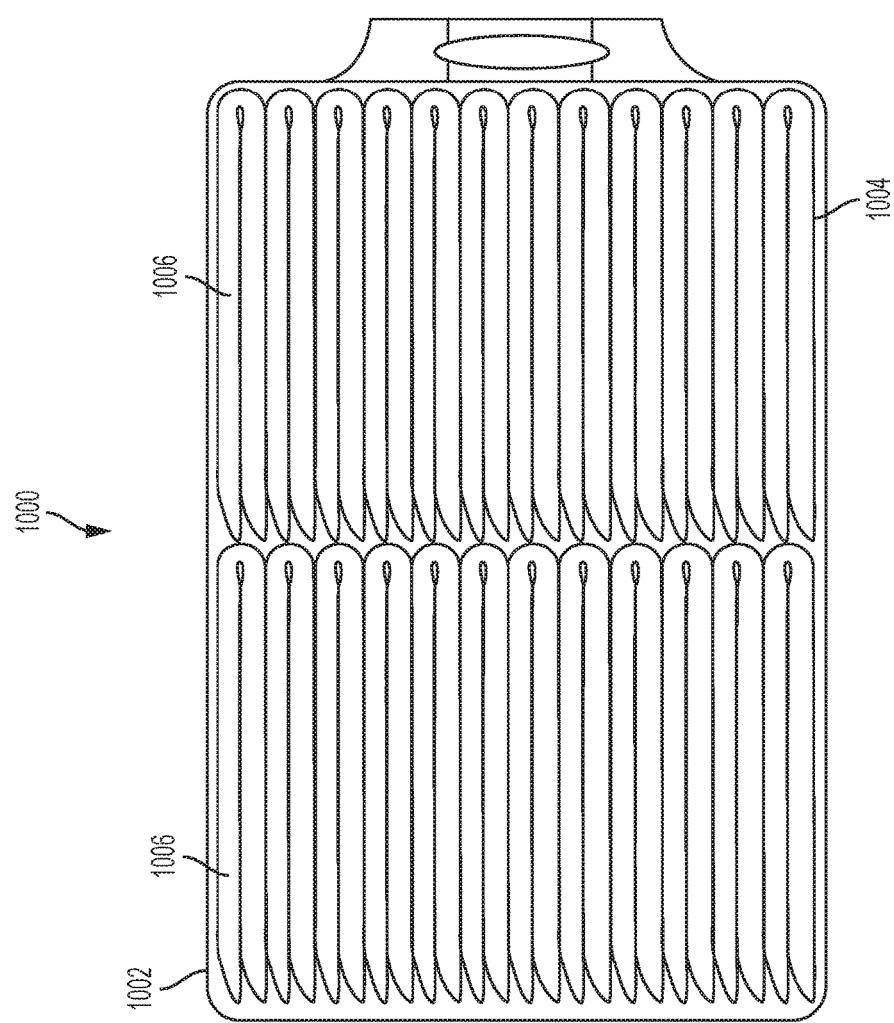
FIG. 13 illustrates an example package of a plurality of the absorbent articles (taped or pant) of the present disclosure.

FIG. 13 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 13). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

CHASSIS EXAMPLES

Examples 1-4 below are prophetic. Use of current brand and trade names is not an indication that the diapers of the examples have been made and marketed. Examples 1-3 are meant to represent inventive prototypes and designs conceived of by applicants. Example 4 is meant to represent some of the types of taped and pant articles known in the art prior to this application for the purpose of comparison against inventive Examples 1-3.

Example 1

Example 1 illustrates diaper and pant chassis that may utilize many of the same raw materials, specifications, machines, processes, and supply chains. Thus, it is expected that the same operators can make the taped and pant chassis of Example 1. And, it is expected that the same quality control measures can be used for them. Another benefit may be greater flexibility of a manufacturer to switch between taped and pant forms to adjust to market demands for one form over the other (versus building larger, more expensive inventories of both forms or alternatively, building and maintaining twice as many expensive taped and pant lines).

Diaper 1 is placed in a first package of absorbent articles and Diaper 2 is placed in a second package of absorbent articles and each of the packages are placed on the same shelf display area of the same store. Diaper 1 has the cross sectional order of components and disposition of the components of the chassis in FIG. 4A above and Diaper 2 has the cross sectional order of components and disposition of the components of the chassis in FIG. 4B above. Diapers 1 and 2 have substantially identical chassis.

Diaper 1:
Form: Taped diaper
Size: 3
Brand: Pampers
Tradename: Baby Dry
Manufacturer: The Procter & Gamble Company
Site of assembly: Plant X
Line type: A
Chassis Materials and Dimensions: Table Immediately Below

|  | Material | Basis Weight (gsm) | Longitudinal Distance (mm) | Transverse Distance (mm) | dtex |
|---|---|---|---|---|---|
| Topsheet (Nonwoven) | Polyolefin | 15 | 440 | 170 | |
| Backsheet (Film) | Polyolefin | 15 | 440 | 200 | |
| Backsheet (Nonwoven) | Polyolefin | 15 | 440 | 200 | |
| Core Wrap (Nonwoven) | Polyolefin | 15 | 360 | 140 | |
| Core-Super Absorbent Polymer | Sodium Polyacrylate | 9 (g) | Mixed with pulp | Mixed with pulp | |
| Core-Air Felt | Pulp | 5 (g) | 360 | 120 | |
| Acquisition Layer (Nonwoven) | Polyester | 40 | | | |
| Inner Leg Cuff (Nonwoven) | Polyolefin | 15 | 440 | | |
| Inner Leg Cuff Elastics | Spundex | | 280 | | 680 |
| Inner Leg Cuff Adhesive | Styrenic polymer hot melt | | | | |
| Outer Leg Cuff (Nonwoven) | Polyolefin | | 440 | | |
| Outer Leg Cuff Elastics | Spundex | | 260 | | 540 |

Chassis Formation:
Left Outer Cuff Distal Edge to Right Outer Cuff Distal Edge distance (front WR, crotch, rear WR): 200 mm
Left Inner Cuff Proximal Edge to Left Outer Cuff Distal Edge distance (front WR, crotch, rear WR): 70 mm
Left Inner Cuff Proximal Edge to Right Inner Cuff Proximal Edge distance (front WR, crotch, rear WR): 70 mm
Free height of each inner cuff: 40 mm
Backsheet film joined to nonwoven outer cover with adhesive Styrenic polymer hot melt in slot coat pattern
Dusting layer is joined to core cover-Inner cuff hem fold width: 15 mm
Cuff joined to TS with pressure bond
Flap Materials and Dimensions: Table Immediately Below

|  | Material | Basis Weight (gsm) | Transverse distance (mm) | Longitudinal distance (mm) | dtex |
|---|---|---|---|---|---|
| Front Ear (Nonwoven) | Polyolefin | 40 | 70 | 70 per each element | |
| Back Ear (Nonwoven) | Polyolefin | 45 | 100 | 50 per each element | |
| Back Ear (Film) | Styrenic polymers | 55 | 100 | 45 per each element | |
| Back Ear Adhesive | Styrenic polymer hot melt | | | | |

Diaper 2:
Form: Pant diaper
Size: 3
Brand: Pampers
Tradename: Easy Ups
Manufacturer: The Procter & Gamble Company
Site of assembly: Plant X
Line type: A
Chassis Materials and Dimensions: Table Immediately Below

|  | Material | Basis Weight (gsm) | Longitudinal Distance (mm) | Transverse Distance (mm) | dtex |
|---|---|---|---|---|---|
| Topsheet (Nonwoven) | Polyolefin | 15 | 440 | 170 | |
| Backsheet (Film) | Polyolefin | 15 | 440 | 180 | |

-continued

|  | Material | Basis Weight (gsm) | Longitudinal Distance (mm) | Transverse Distance (mm) | dtex |
|---|---|---|---|---|---|
| Backsheet (Nonwoven) | Polyolefin | 15 | 440 | 180 |  |
| Core Wrap (Nonwoven) | Polyolefin | 15 | 360 | 140 |  |
| Core-Super Absorbent Polymer | Sodium Polyacrylate | 9 (g) | Mixed with pulp | Mixed with pulp |  |
| Core-Air Felt | Pulp | 4.5 (g) | 360 | 120 |  |
| Acquisition Layer (Nonwoven) | Polyester | 40 |  |  |  |
| Inner Leg Cuff (Nonwoven) | Polyolefin | 15 | 440 |  |  |
| Inner Leg Cuff Elastics | Spundex |  | 280 |  | 680 |
| Inner Leg Cuff Adhesive | Styrenic polymer hot melt |  |  |  |  |
| Outer Leg Cuff (Nonwoven) | Polyolefin |  | 440 |  |  |
| Outer Leg Cuff Elastics | Spundex |  | 260 |  | 540 |

Chassis Formation:

Left Outer Cuff Distal Edge to Right Outer Cuff Distal Edge distance (front WR, crotch, rear WR): 200 mm Left Inner Cuff Distal Edge to Left Outer Cuff Distal Edge distance (front WR, crotch, rear WR): 70 mm Left Inner Cuff Proximal Edge to Right Inner Cuff Proximal Edge distance (front WR, crotch, rear WR): 70 mm Free height of each inner cuff: 40 mm Backsheet film joined to nonwoven outer cover with adhesive Styrenic polymer hot melt in slot coat pattern Dusting layer is joined to core cover-Inner cuff hem fold width: 15 mm Cuff joined to TS with pressure bond Flap Materials and Dimensions: Table Immediately Below

|  | Material | Basis Weight (gsm) | Transverse distance (mm) | Longitudinal distance (mm) | dtex |
|---|---|---|---|---|---|
| Front Belt Outer Layer (Nonwoven) | Polyolefin | 10 | 375 | 180 |  |
| Front Belt Inner Layer (Nonwoven) | Polyolefin | 10 | 375 | 140 |  |
| Front Belt Elastics | Spundex |  | 375 (prestretched 100%~270%) |  | 540 |
| Back Belt Outer Layer (Nonwoven) | Polyolefin | 10 | 375 | 220 |  |
| Back Belt Inner Layer (Nonwoven) | Polyolefin | 10 | 375 | 170 |  |
| Back Belt Elastics | Spundex |  | 375 (prestretched 100%~270%) |  | 540 |

Example 2

Example 2 illustrates diaper and pant chassis that may utilize many of the same raw materials, specifications, machines, processes, and supply chains. It is expected that the same quality control measures can be used for them.

Diaper 3 is placed in a third package of absorbent articles and Diaper 4 is placed in a fourth package of absorbent articles and each of the packages are displayed at a common retailer (e.g., Walmart). Diaper 3 has the cross sectional order of components and disposition of the components of the chassis in FIG. 4A above and Diaper 4 has the cross sectional order of components and disposition of the components of the chassis in FIG. 4B above. Diapers 3 and 4 have substantially identical chassis.

Diaper 3:
Form: Taped diaper
Size: 3
Brand: Pampers
Tradename: Baby Dry
Manufacturer: The Procter & Gamble Company
Site of assembly: Plant X
Line type: A
Chassis Materials and Dimensions: Table Immediately Below

| | Material | Basis Weight (gsm) | Longitudinal Distance (mm) | Transverse Distance (mm) | dtex |
|---|---|---|---|---|---|
| Topsheet (Nonwoven) | Polyolefin | 15 | 440 | 170 | |
| Backsheet (Film) | Polyolefin | 15 | 440 | 200 | |
| Backsheet (Nonwoven) | Polyolefin | 15 | 440 | 200 | |
| Core Wrap (Nonwoven) | Polyolefin | 15 | 360 | 140 | |
| Core-Super Absorbent Polymer | Sodium Polyacrylate | 9 (g) | Mixed with pulp | Mixed with pulp | |
| Core-Air Felt | Pulp | 5 (g) | 360 | 120 | |
| Acquisition Layer (Nonwoven) | Polyester | 40 | | | |
| Inner Leg Cuff (Nonwoven) | Polyolefin | 15 | 440 | | |
| Inner Leg Cuff Elastics | Spundex | | 280 | | 680 |
| Inner Leg Cuff Adhesive | Styrenic polymer hot melt | | | | |
| Outer Leg Cuff (Nonwoven) | Polyolefin | | 440 | | |
| Outer Leg Cuff Elastics | Spundex | | 260 | | 540 |

Chassis Formation:
Left Outer Cuff Distal Edge to Right Outer Cuff Distal Edge distance (front WR, crotch, rear WR): 200 mm
Left Inner Cuff Distal Edge to Left Outer Cuff Distal Edge distance (front WR, crotch, rear WR): 70 mm
Left Inner Cuff Proximal Edge to Right Inner Cuff Proximal Edge distance (front WR, crotch, rear WR): 70 mm
Free height of each inner cuff: 40 mm
Backsheet film joined to nonwoven outer cover with adhesive Styrenic polymer hot melt in slot coat pattern
Dusting layer is joined to core cover
Inner cuff hem fold width 15 mm
Cuff joined to TS with pressure bond
Flap Materials and Dimensions: Table Below:

| | Material | Basis Weight (gsm) | Transverse distance (mm) | Longitudinal distance (mm) | dtex |
|---|---|---|---|---|---|
| Front Ear (Nonwoven) | Polyolefin | 40 | 70 | 70 per each element | |
| Back Ear (Nonwoven) | Polyolefin | 45 | 100 | 50 per each element | |
| Back Ear (Film) | Styrenic polymers | 55 | 100 | 45 per each element | |
| Back Ear Adhesive | Styrenic polymer hot melt | | | | |

Diaper 4:
Form: Pant diaper
Size: 4
Brand: Pampers
Tradename: Easy Ups
Manufacturer: The Procter & Gamble Company
Site of assembly: Plant X
Line type: A
Chassis Materials and Dimensions: Table Immediately Below

| | Material | Basis Weight (gsm) | Longitudinal Distance (mm) | Transverse Distance (mm) | dtex |
|---|---|---|---|---|---|
| Topsheet (Nonwoven) | Polyolefin | 15 | 440 | 170 | |
| Backsheet (Film) | Polyolefin | 15 | 440 | 180 | |

-continued

|  | Material | Basis Weight (gsm) | Longitudinal Distance (mm) | Transverse Distance (mm) | dtex |
|---|---|---|---|---|---|
| Backsheet (Nonwoven) | Polyolefin | 15 | 440 | 180 |  |
| Core Wrap (Nonwoven) | Polyolefin | 15 | 360 | 140 |  |
| Core-Super Absorbent Polymer | Sodium Polyacrylate | 9 (g) | Mixed with pulp | Mixed with pulp |  |
| Core-Air Felt | Pulp | 4.5 (g) | 360 | 120 |  |
| Acquisition Layer (Nonwoven) | Polyester | 40 |  |  |  |
| Inner Leg Cuff (Nonwoven) | Polyolefin | 15 | 440 |  |  |
| Inner Leg Cuff Elastics | Spundex |  | 280 |  | 680 |
| Inner Leg Cuff Adhesive | Styrenic polymer hot melt |  |  |  |  |
| Outer Leg Cuff (Nonwoven) | Polyolefin |  | 440 |  |  |
| Outer Leg Cuff Elastics | Spundex |  | 260 |  | 540 |

Chassis Formation:
Left Outer Cuff Distal Edge to Right Outer Cuff Distal Edge distance (front WR, crotch, rear WR): 200 mm
Left Inner Cuff Distal Edge to Left Outer Cuff Distal Edge distance (front WR, crotch, rear WR): 70 mm
Left Inner Cuff Proximal Edge to Right Inner Cuff Proximal Edge distance (front WR, crotch, rear WR): 70 mm
Free height of each inner cuff: 40 mm Backsheet film joined to nonwoven outer cover with adhesive Styrenic polymer hot melt in slot coat pattern
Dusting layer is joined to core cover-Inner cuff hem fold width: 15 mm
Cuff joined to TS with pressure bond
Flap Materials and Dimensions: Table Immediately Below

|  | Material | Basis Weight (gsm) | Transverse distance (mm) | Longitudinal distance (mm) | dtex |
|---|---|---|---|---|---|
| Front Belt Outer Layer (Nonwoven) | Polyolefin | 10 | 375 | 180 |  |
| Front Belt Inner Layer (Nonwoven) | Polyolefin | 10 | 375 | 140 |  |
| Front Belt Elastics | Spundex |  | 375 (prestretched 100%~270%) |  | 540 |
| Back Belt Outer Layer (Nonwoven) | Polyolefin | 10 | 375 | 220 |  |
| Back Belt Inner Layer (Nonwoven) | Polyolefin | 10 | 375 | 170 |  |
| Back Belt Elastics | Spundex |  | 375 (prestretched 100%~270%) |  | 540 |

Example 3

Example 3 illustrates diaper and pant chassis that may utilize many of the same raw materials, specifications, machines, processes, and supply chains. It is expected that the same quality control measures can be used for them.
Diaper 5 is placed in a fifth package of absorbent articles, Diaper 6 is placed in a sixth package of absorbent articles, Diaper 7 is placed in a seventh package of absorbent articles, and Diaper 8 is placed in an eighth package of absorbent articles. Diapers 5-8 have identical or substantially identical chassis.
Diaper 5:
Form: Taped diaper
Size: 3
Brand: Pampers
Tradename: Baby Dry
Manufacturer: The Procter & Gamble Company
Site of assembly: Plant X
Line type: A Chassis Materials and Dimensions: Table Immediately Below

|  | Material | Basis Weight (gsm) | Longitudinal Distance (mm) | Transverse Distance (mm) | dtex |
|---|---|---|---|---|---|
| Topsheet (Nonwoven) | Polyolefin | 15 | 440 | 170 |  |
| Backsheet (Film) | Polyolefin | 15 | 440 | 200 |  |
| Backsheet (Nonwoven) | Polyolefin | 15 | 440 | 200 |  |
| Core Wrap (Nonwoven) | Polyolefin | 15 | 360 | 140 |  |
| Core-Super Absorbent Polymer | Sodium Polyacrylate | 9 (g) | Mixed with pulp | Mixed with pulp |  |
| Core-Air Felt | Pulp | 5 (g) | 360 | 120 |  |
| Acquisition Layer (Nonwoven) | Polyester | 40 |  |  |  |
| Inner Leg Cuff (Nonwoven) | Polyolefin | 15 | 440 |  |  |
| Inner Leg Cuff Elastics | Spundex |  | 280 |  | 680 |
| Inner Leg Cuff Adhesive | Styrenic polymer hot melt |  |  |  |  |
| Outer Leg Cuff (Nonwoven) | Polyolefin |  | 440 |  |  |
| Outer Leg Cuff Elastics | Spundex |  | 260 |  | 540 |

Chassis Formation:
Left Outer Cuff Distal Edge to Right Outer Cuff Distal Edge distance (front WR, crotch, rear WR): 200 mm
Left Inner Cuff Distal Edge to Left Outer Cuff Distal Edge distance (front WR, crotch, rear WR): 70 mm
Left Inner Cuff Proximal Edge to Right Inner Cuff Proximal Edge distance (front WR, crotch, rear WR): 70 mm
Free height of each inner cuff: 40 mm
Backsheet film joined to nonwoven outer cover with adhesive Styrenic polymer hot melt in slot coat pattern
Dusting layer is joined to core cover-Inner cuff hem fold width 15 mm
Cuff joined to TS with pressure bond
Flap Materials and Dimensions: Table Below:

|  | Material | Basis Weight (gsm) | Transverse distance (mm) | Longitudinal distance (mm) | dtex |
|---|---|---|---|---|---|
| Front Ear (Nonwoven) | Polyolefin | 40 | 70 | 70 per each element |  |
| Back Ear (Nonwoven) | Polyolefin | 45 | 100 | 50 per each element |  |
| Back Ear (Film) | Styrenic polymers | 55 | 100 | 45 per each element |  |
| Back Ear Adhesive | Styrenic polymer hot melt |  |  |  |  |

Diaper 6:
Form: Pant diaper
Size: 3
Brand: Pampers
Tradename: Easy Ups
Manufacturer: The Procter & Gamble Company
Site of assembly: Plant Y
Line type: A
Chassis Materials and Dimensions: Table Immediately Below

|  | Material | Basis Weight (gsm) | Longitudinal Distance (mm) | Transverse Distance (mm) | dtex |
|---|---|---|---|---|---|
| Topsheet (Nonwoven) | Polyolefin | 15 | 440 | 170 |  |
| Backsheet (Film) | Polyolefin | 15 | 440 | 200 |  |
| Backsheet (Nonwoven) | Polyolefin | 15 | 440 | 200 |  |
| Core Wrap (Nonwoven) | Polyolefin | 15 | 360 | 140 |  |
| Core-Super Absorbent Polymer | Sodium Polyacrylate | 9 (g) | Mixed with pulp | Mixed with pulp |  |
| Core-Air Felt | Pulp | 5 (g) | 360 | 120 |  |
| Acquisition Layer (Nonwoven) | Polyester | 40 |  |  |  |

-continued

|  | Material | Basis Weight (gsm) | Longitudinal Distance (mm) | Transverse Distance (mm) | dtex |
|---|---|---|---|---|---|
| Inner Leg Cuff (Nonwoven) | Polyolefin | 15 | 440 | | |
| Inner Leg Cuff Elastics | Spundex | | 280 | | 680 |
| Inner Leg Cuff Adhesive | Styrenic polymer hot melt | | | | |
| Outer Leg Cuff (Nonwoven) | Polyolefin | | 440 | | |
| Outer Leg Cuff Elastics | Spundex | | 260 | | 540 |

Chassis Formation:
Left Outer Cuff Distal Edge to Right Outer Cuff Distal Edge distance (front WR, crotch, rear WR): 200 mm
Left Inner Cuff Distal Edge to Left Outer Cuff Distal Edge distance (front WR, crotch, rear WR): 70 mm
Left Inner Cuff Proximal Edge to Right Inner Cuff Proximal Edge distance (front WR, crotch, rear WR): 70 mm
Free height of each inner cuff: 40 mm Backsheet film joined to nonwoven outer cover with adhesive Styrenic polymer hot melt in slot coat pattern
Dusting layer is joined to core cover-Inner cuff hem fold width: 15 mm
Cuff joined to TS with pressure bond
Flap Materials and Dimensions: Table Immediately Below

|  | Material | Basis Weight (gsm) | Transverse distance (mm) | Longitudinal distance (mm) | dtex |
|---|---|---|---|---|---|
| Front Belt Outer Layer (Nonwoven) | Polyolefin | 10 | 375 | 180 | |
| Front Belt Inner Layer (Nonwoven) | Polyolefin | 10 | 375 | 140 | |
| Front Belt Elastics | Spundex | | 375 (prestretched 100%~270%) | | 540 |
| Back Belt Outer Layer (Nonwoven) | Polyolefin | 10 | 375 | 220 | |
| Back Belt Inner Layer (Nonwoven) | Polyolefin | 10 | 375 | 170 | |
| Back Belt Elastics | Spundex | | 375 (prestretched 100%~270%) | | 540 |

Diaper 7:
Form: Taped diaper
Size: 4
Brand: Luvs
Tradename: Luvs
Manufacturer: The Procter & Gamble Company
Site of assembly: Plant Z
Line type: A
Chassis Materials and Dimensions: Table Immediately Below

|  | Material | Basis Weight (gsm) | Longitudinal Distance (mm) | Transverse Distance (mm) | dtex |
|---|---|---|---|---|---|
| Topsheet (Nonwoven) | Polyolefin | 15 | 440 | 170 | |
| Backsheet (Film) | Polyolefin | 15 | 440 | 200 | |
| Backsheet (Nonwoven) | Polyolefin | 15 | 440 | 200 | |
| Core Wrap (Nonwoven) | Polyolefin | 15 | 360 | 140 | |
| Core-Super Absorbent Polymer | Sodium Polyacrylate | 9 (g) | Mixed with pulp | Mixed with pulp | |
| Core-Air Felt | Pulp | 5 (g) | 360 | 120 | |
| Acquisition Layer (Nonwoven) | Polyester | 40 | | | |
| Inner Leg Cuff (Nonwoven) | Polyolefin | 15 | 440 | | |
| Inner Leg Cuff Elastics | Spundex | | 280 | | 680 |
| Inner Leg Cuff Adhesive | Styrenic polymer hot melt | | | | |

| | Material | Basis Weight (gsm) | Longitudinal Distance (mm) | Transverse Distance (mm) | dtex |
|---|---|---|---|---|---|
| Outer Leg Cuff (Nonwoven) | Polyolefin | | 440 | | |
| Outer Leg Cuff Elastics | Spundex | | 260 | | 540 |

Chassis Formation:
Left Outer Cuff Distal Edge to Right Outer Cuff Distal Edge distance (front WR, crotch, rear WR): 200 mm
Left Inner Cuff Distal Edge to Left Outer Cuff Distal Edge distance (front WR, crotch, rear WR): 70 mm
Left Inner Cuff Proximal Edge to Right Inner Cuff Proximal Edge distance (front WR, crotch, rear WR): 70 mm
Free height of each inner cuff: 40 mm Backsheet film joined to nonwoven outer cover with adhesive Styrenic polymer hot melt in slot coat pattern
Dusting layer is joined to core cover-Inner cuff hem fold width 15 mm
Cuff joined to TS with pressure bond
Flap Materials and Dimensions: Table Immediately Below

| | Material | Basis Weight (gsm) | Transverse distance (mm) | Longitudinal distance (mm) | dtex |
|---|---|---|---|---|---|
| Front Ear (Nonwoven) | Polyolefin | 40 | 70 | 70 per each element | |
| Back Ear (Nonwoven) | Polyolefin | 45 | 100 | 50 per each element | |
| Back Ear (Film) | Styrenic polymers | 55 | 100 | 45 per each element | |
| Back Ear Adhesive | Styrenic polymer hot melt | | | | |

Diaper 8:
Form: Pant diaper
Size: 3
Brand: Private label
Tradename: Private label
Manufacturer: The Procter & Gamble Company
Site of assembly: Plant Z
Line type: C
Chassis Materials and Dimensions: Table Immediately Below

| | Material | Basis Weight (gsm) | Longitudinal Distance (mm) | Transverse Distance (mm) | dtex |
|---|---|---|---|---|---|
| Topsheet (Nonwoven) | Polyolefin | 15 | 440 | 170 | |
| Backsheet (Film) | Polyolefin | 15 | 440 | 200 | |
| Backsheet (Nonwoven) | Polyolefin | 15 | 440 | 200 | |
| Core Wrap (Nonwoven) | Polyolefin | 15 | 360 | 140 | |
| Core-Super Absorbent Polymer | Sodium Polyacrylate | 9 (g) | Mixed with pulp | Mixed with pulp | |
| Core-Air Felt | Pulp | 5 (g) | 360 | 120 | |
| Acquisition Layer (Nonwoven) | Polyester | 40 | | | |
| Inner Leg Cuff (Nonwoven) | Polyolefin | 15 | 440 | | |
| Inner Leg Cuff Elastics | Spundex | | 280 | | 680 |
| Inner Leg Cuff Adhesive | Styrenic polymer hot melt | | | | |
| Outer Leg Cuff (Nonwoven) | Polyolefin | | 440 | | |
| Outer Leg Cuff Elastics | Spundex | | 260 | | 540 |

Chassis Formation:
Left Outer Cuff Distal Edge to Right Outer Cuff Distal Edge distance (front WR, crotch, rear WR): 200 mm
Left Inner Cuff Distal Edge to Left Outer Cuff Distal Edge distance (front WR, crotch, rear WR): 70 mm
Left Inner Cuff Proximal Edge to Right Inner Cuff Proximal Edge distance (front WR, crotch, rear WR): 70 mm
Free height of each inner cuff: 40 mm Backsheet film joined to nonwoven outer cover with adhesive Styrenic polymer hot melt in slot coat pattern
Dusting layer is joined to core cover-Inner cuff hem fold width: 15 mm
Cuff joined to TS with pressure bond
Flap Materials and Dimensions: Table Immediately Below

|  | Material | Basis Weight (gsm) | Transverse distance (mm) | Longitudinal distance (mm) | dtex |
|---|---|---|---|---|---|
| Front Belt Outer Layer (Nonwoven) | Polyolefin | 10 | 375 | 180 |  |
| Front Belt Inner Layer (Nonwoven) | Polyolefin | 10 | 375 | 140 |  |
| Front Belt Elastics | Spundex |  | 375 (prestretched 100%~270%) |  | 540 |
| Back Belt Outer Layer (Nonwoven) | Polyolefin | 10 | 375 | 220 |  |
| Back Belt Inner Layer (Nonwoven) | Polyolefin | 10 | 375 | 170 |  |
| Back Belt Elastics | Spundex |  | 375 (prestretched 100%~270%) |  | 540 |

Example 4

Comparative Example

Example 4 illustrates diaper and pant chassis that don't utilize as many of the same raw materials, specifications, machines, processes, and supply chains as the diapers of Examples 1-3. Thus, the same operators may not be able to make both the taped and pant chassis of Example 4 (that is, separate teams of operators may be required). And, different quality control measures may need to be used for them. The diapers of Example 4, due to the dissimilarity of the chassis, will likely cost more to make, will likely take longer to qualify, will likely increase the management of the supply chain, will likely increase the warehousing needs, and will likely complicate process of equipment change over (if using the same line for both).

Further, unlike the chassis of Diapers 1 and 2, the chassis of Diapers 9 and 10 are not interchangeable. Using the chassis of Diaper 9 with the flaps of Diaper 10 or using the chassis of Diaper 10 with the flaps of Diaper 9, even though they are for the same sized article, would likely result in fit problems, may result in leaks, and will likely have application issues.

Diaper 9 is placed in a first package of absorbent articles and Diaper 10 is placed in a second package of absorbent articles and each of the packages are placed on the same shelf display. Diapers 9 and 10 are not identical and are not substantially identical.

Diaper 9:
Form: Taped diaper
Size: 3
Brand: Pampers
Tradename: Baby Dry
Manufacturer: The Procter & Gamble Company
Site of assembly: Plant X
Line type: A Chassis Materials and Dimensions: Table Immediately Below

| | Material | Basis Weight (gsm) | Longitudinal Distance (mm) | Transverse Distance (mm) | dtex |
|---|---|---|---|---|---|
| Topsheet (Nonwoven) | Polyolefin | 15 | 440 | 170 | |
| Backsheet (Film) | Polyolefin | 15 | 440 | 200 | |
| Backsheet (Nonwoven) | Polyolefin | 15 | 440 | 200 | |
| Core Wrap (Nonwoven) | Polyolefin | 15 | 360 | 140 | |
| Core-Super Absorbent Polymer | Sodium Polyacrylate | 9 (g) | Mixed with pulp | Mixed with pulp | |
| Core-Air Felt | Pulp | 5 (g) | 360 | 120 | |
| Acquisition Layer (Nonwoven) | Polyester | 40 | | | |
| Inner Leg Cuff (Nonwoven) | Polyolefin | 15 | 440 | | |
| Inner Leg Cuff Elastics | Spundex | | 280 | | 680 |
| Inner Leg Cuff Adhesive | Styrenic polymer hot melt | | | | |
| Outer Leg Cuff (Nonwoven) | Polyolefin | | 440 | | |
| Outer Leg Cuff Elastics | Spundex | | 260 | | 540 |

Chassis Formation:
Left Outer Cuff Distal Edge to Right Outer Cuff Distal Edge distance (front WR, crotch, rear WR): 200 mm
Left Inner Cuff Distal Edge to Left Outer Cuff Distal Edge distance (front WR, crotch, rear WR): 70 mm
Left Inner Cuff Proximal Edge to Right Inner Cuff Proximal Edge distance (front WR, crotch, rear WR): 70 mm
Free height of each inner cuff: 40 mm Backsheet film joined to nonwoven outer cover with adhesive Styrenic polymer hot melt in slot coat pattern
Dusting layer is joined to core cover-Inner cuff hem fold width: 15 mm
Cuff joined to TS with pressure bond Flap Materials and Dimensions: Table Immediately Below

| | Material | Basis Weight (gsm) | Transverse distance (mm) | Longitudinal distance (mm) | dtex |
|---|---|---|---|---|---|
| Front Ear (Nonwoven) | Polyolefin | 40 | 70 | 70 per each element | |
| Back Ear (Nonwoven) | Polyolefin | 45 | 100 | 50 per each element | |
| Back Ear (Film) | Styrenic polymers | 55 | 100 | 45 per each element | |
| Back Ear Adhesive | Styrenic polymer hot melt | | | | |

Diaper 10:
Form: Pant diaper
Size: 3
Brand: Pampers
Tradename: Easy Ups
Manufacturer: The Procter & Gamble Company
Site of assembly: Plant X
Line type: B
Chassis Materials and Dimensions: Table Immediately Below

| | Material | Basis Weight (gsm) | Longitudinal Distance (mm) | Transverse Distance (mm) | dtex |
|---|---|---|---|---|---|
| Topsheet (Nonwoven) | Polyolefin | 15 | 480 | 170 | |
| Backsheet (Film) | Polyolefin | 15 | 480 | 120 | |
| Backsheet (Nonwoven) | Polyolefin | 30 | 480 | 290 | |
| Core Wrap (Nonwoven) | Polyolefin | 15 | 420 | 140 | |
| Core-Super Absorbent Polymer | Sodium Polyacrylate | 12 (g) | Mixed with pulp | Mixed with pulp | |
| Core-Air Felt | Pulp | 9 (g) | 420 | 90 | |

-continued

| | Material | Basis Weight (gsm) | Longitudinal Distance (mm) | Transverse Distance (mm) | dtex |
|---|---|---|---|---|---|
| Acquisition Layer (Nonwoven) | Polyester | 40 | | | |
| Inner Leg Cuff (Nonwoven) | Polyolefin | 15 | 480 | | |
| Inner Leg Cuff Elastics | Spundex | | 280 | | 1240 |
| Inner Leg Cuff Adhesive | Styrenic polymer hot melt | | | | |
| Outer Leg Cuff (Nonwoven) | Polyolefin | | 480 | | |
| Outer Leg Cuff Elastics | Spundex | | 260 | | 1100 |

Chassis Formation:
Left Outer Cuff Distal Edge to Right Outer Cuff Distal Edge distance (front WR, crotch, rear WR): 160 mm
Left Inner Cuff Distal Edge to Left Outer Cuff Distal Edge distance (front WR, crotch, rear WR): 60 mm
Left Inner Cuff Proximal Edge to Right Inner Cuff Proximal Edge distance (front WR, crotch, rear WR): 110 mm
Backsheet film joined to nonwoven outer cover with adhesive Styrenic polymer hot melt in slot coat pattern
Dusting layer is joined to core cover-Inner cuff hem fold width: 15 mm
Cuff joined to TS with pressure bond
Flap Materials and Dimensions: Table Immediately Below Material basis weight is measured in accordance with ASTM D 756, ISO 536 or ERT-40.3-90.

FLAP EXAMPLES

Examples 1-8 below are prophetic. Use of current brand and trade names is not an indication that the diapers of the examples have been made and marketed. Examples 1-8 are meant to represent inventive prototypes, designs, and/or arrays conceived of by applicants.

Example 1

Example 1 illustrates diaper and pant articles that may utilize many of the same raw materials, specifications,

| | Material | Basis Weight (gsm) | Transverse distance (mm) | Longitudinal distance (mm) | dtex |
|---|---|---|---|---|---|
| Front Flap Outer Layer (Nonwoven) | Polyolefin (Part of Backsheet nonwoven) | 30 | NA (Part of Backsheet nonwoven) | NA (Part of Backsheet nonwoven) | |
| Front Flap Inner Layer (Nonwoven) | Polyolefin | 25 | 110 | 70 per each element | |
| Front Flap Elastics | Styrene-butadiene copolymer film | 70 | 110 | 60 per each element | NA |
| Back Flap Outer Layer (Nonwoven) | Polyolefin (Part of Backsheet nonwoven) | 30 | NA (Part of Backsheet nonwoven) | NA (Part of Backsheet nonwoven) | |
| Back Flap Inner Layer (Nonwoven) | Polyolefin | 25 | 150 | 70 per each element | |
| Back Flap Elastics | Styrene-butadiene copolymer film | 70 | 150 | 60 per each element | NA |

All dimensions in the above chassis examples are measured in fully stretched conditions in the lateral direction and the transverse direction, either on a finished product or on raw materials. One or more flaps of pant articles may be cut or separated from the chassis so that the measurements of the dimensions can be done in a flat condition. The core width is defined as a width of the pulp deposit and super absorbent polymer, and does not include the nonwoven material and/or tissue material that encapsulates the pulp and/or super absorbent polymer (i.e., does not include the core wrap). If the lateral edges and/or the transverse edges of the core is not straight, the measurement is done at the longest and/or the widest location of the core. The dimensions of the pant article and the taped article should be done under same conditions (e.g., ambient temperature for both, the same measurement apparatus for both) and in the same manner for consistent results. Product specifications, product drawings, and equipment drawings may be substituted for measuring actual products.

Elastic decitex (Dtex) is obtained from suppliers' specification.

machines, processes, and supply chains to fabricate the flaps. Thus, it is expected that the same operators can make the taped and pant flaps of Example 1. And, it is expected that the same quality control measures can be used for them. Another benefit may be greater flexibility of a manufacturer to switch between taped and pant forms to adjust to market demands for one form over the other (versus building larger, more expensive inventories of both forms or alternatively, building and maintaining twice as many expensive taped and pant lines).

Diapers 1 and 2 are placed in different packages and each of the packages are displayed at a common retailer (e.g., Walmart). Diapers 1 and 2 have substantially identical flaps.
Diaper 1:
Form: Taped diaper
Size: 4
Brand: Pampers
Tradename: Baby Dry
Manufacturer: The Procter & Gamble Company
Site of assembly: Plant X
Line type: A
Chassis: Same specifications detailed in Diaper 1 from the Chassis Example section (above).

Flap Materials and Dimensions: Table Below:

| | Material | Basis Weight (gsm) | Transverse distance (mm) | Longitudinal distance (mm) | dtex |
|---|---|---|---|---|---|
| Front Belt Outer Layer (Nonwoven) | Polyolefin | 10 | 375 | 180 | |
| Front Belt Inner Layer (Nonwoven) | Polyolefin | 10 | 375 | 140 | |
| Front Belt Elastics | Spundex | | 375 (prestretched 100%~270%) | | 540 |
| Back Belt Outer Layer (Nonwoven) | Polyolefin | 10 | 375 | 220 | |
| Back Belt Inner Layer (Nonwoven) | Polyolefin | 10 | 375 | 170 | |
| Back Belt Elastics | Spundex | | 375 (prestretched 100%~270%) | | 540 |
| Fastening tab | Polyolefin | 80 | 45 per each element | 30 per each element | |
| Hook | Polyolefin | 60 | 13 per each element | 30 per each element | |

Diaper 2:
Form: Pant diaper
Size: 4
Brand: Pampers
Tradename: Easy Ups
Manufacturer: The Procter & Gamble Company
Site of assembly: Plant YX
Line type: A
Chassis: Same specifications detailed in Diaper 2 from the Chassis Example section (above).
Flap Materials and Dimensions: Table Immediately Below

| | Material | Basis Weight (gsm) | Transverse distance (mm) | Longitudinal distance (mm) | dtex |
|---|---|---|---|---|---|
| Front Belt Outer Layer (Nonwoven) | Polyolefin | 10 | 375 | 180 | |
| Front Belt Inner Layer (Nonwoven) | Polyolefin | 10 | 375 | 140 | |
| Front Belt Elastics | Spundex | | 375 (prestretched 100%~270%) | | 540 |
| Back Belt Outer Layer (Nonwoven) | Polyolefin | 10 | 375 | 220 | |
| Back Belt Inner Layer (Nonwoven) | Polyolefin | 10 | 375 | 170 | |
| Back Belt Elastics | Spundex | | 375 (prestretched 100%~270%) | | 540 |

Example 2

Example 2 illustrates diaper and pant flaps that may utilize many of the same raw materials, specifications, machines, processes, and supply chains. It is expected that the same quality control measures can be used for them.

Diapers 3 and 4 are placed in different packages and each of the packages are displayed at a common retailer (e.g., Walmart). Diapers 3 and 4 have substantially identical flaps.

Diaper 3:
Form: Taped diaper
Size: 4
Brand: Pampers
Tradename: Baby Dry
Manufacturer: The Procter & Gamble Company
Site of assembly: Plant X
Line type: A
Chassis: Same specifications detailed in Diaper 3 from the Chassis Example section (above).
Flap Materials and Dimensions: Table Below:

| | Material | Basis Weight (gsm) | Transverse distance (mm) | Longitudinal distance (mm) | dtex |
|---|---|---|---|---|---|
| Front Belt Outer Layer (Nonwoven) | Polyolefin | 10 | 400 | 160 | |

-continued

| | Material | Basis Weight (gsm) | Transverse distance (mm) | Longitudinal distance (mm) | dtex |
|---|---|---|---|---|---|
| Front Belt Inner Layer (Nonwoven) | Polyolefin | 10 | 400 | 120 | |
| Front Belt Elastics | Spundex | | 400 (prestretched 100%~270%) | | 540 |
| Back Belt Outer Layer (Nonwoven) | Polyolefin | 10 | 450 | 210 | |
| Back Belt Inner Layer (Nonwoven) | Polyolefin | 10 | 450 | 160 | |
| Back Belt Elastics | Spundex | | 450 (prestretched 100%~270%) | | 540 |
| Fastening tab | Polyolefin | 80 | 45 per each element | 30 per each element | |
| Hook | Polyolefin | 60 | 13 per each element | 30 per each element | |

Diaper 4:
Form: Pant diaper
Size: 4
Brand: Pampers
Tradename: Easy Ups
Manufacturer: The Procter & Gamble Company
Site of assembly: PlantX
Line type: A
Chassis: Same specifications detailed in Diaper 4 from the Chassis Example section (above).
Flap Materials and Dimensions: Table Immediately Below

| | Material | Basis Weight (gsm) | Transverse distance (mm) | Longitudinal distance (mm) | dtex |
|---|---|---|---|---|---|
| Front Belt Outer Layer (Nonwoven) | Polyolefin | 10 | 375 | 180 | |
| Front Belt Inner Layer (Nonwoven) | Polyolefin | 10 | 375 | 140 | |
| Front Belt Elastics | Spundex | | 375 (prestretched 100%~270%) | | 540 |
| Back Belt Outer Layer (Nonwoven) | Polyolefin | 10 | 375 | 220 | |
| Back Belt Inner Layer (Nonwoven) | Polyolefin | 10 | 375 | 170 | |
| Back Belt Elastics | Spundex | | 375 (prestretched 100%~270%) | | 540 |

Example 3

Example 3 illustrates diaper and pant flaps that may utilize many of the same raw materials, specifications, machines, processes, and supply chains. It is expected that the same quality control measures can be used for them.

Diapers 5 and 6 are placed in different packages and each of the packages are displayed at a common retailer (e.g., Walmart). Diapers 15 and 16 have substantially identical flaps.

Diaper 5:
Form: Taped diaper
Size: 4
Brand: Pampers
Tradename: Baby Dry
Manufacturer: The Procter & Gamble Company
Site of assembly: Plant X
Line type: A
Chassis: Same specifications detailed in Diaper 1 from the Chassis Example section (above).
Flap Materials and Dimensions: Table Below:

| | Material | Basis Weight (gsm) | Transverse distance (mm) | Longitudinal distance (mm) | dtex |
|---|---|---|---|---|---|
| Back Belt Outer Layer (Nonwoven) | Polyolefin | 10 | 500 | 170 | |
| Back Belt Inner Layer (Nonwoven) | Polyolefin | 10 | 500 | 120 | |

-continued

|  | Material | Basis Weight (gsm) | Transverse distance (mm) | Longitudinal distance (mm) | dtex |
|---|---|---|---|---|---|
| Back Belt Elastics | Spundex |  | 500 (prestretched 100%~270%) |  | 540 |
| Fastening tab | Polyolefin | 80 | 45 per each element | 30 per each element |  |
| Hook | Polyolefin | 60 | 13 per each element | 30 per each element |  |

Diaper 6:
Form: Pant diaper
Size: 4
Brand: Pampers
Tradename: Easy Ups
Manufacturer: The Procter & Gamble Company
Site of assembly: Plant X
Line type: A
Chassis: Same specifications detailed in Diaper 2 from the Chassis Example section (above).
Flap Materials and Dimensions: Table Immediately Below

|  | Material | Basis Weight (gsm) | Transverse distance (mm) | Longitudinal distance (mm) | dtex |
|---|---|---|---|---|---|
| Front Belt Outer Layer (Nonwoven) | Polyolefin | 10 | 375 | 180 |  |
| Front Belt Inner Layer (Nonwoven) | Polyolefin | 10 | 375 | 140 |  |
| Front Belt Elastics | Spundex |  | 375 (prestretched 100%~270%) |  | 540 |
| Back Belt Outer Layer (Nonwoven) | Polyolefin | 10 | 375 | 220 |  |
| Back Belt Inner Layer (Nonwoven) | Polyolefin | 10 | 375 | 170 |  |
| Back Belt Elastics | Spundex |  | 375 (prestretched 100%~270%) |  | 540 |

Example 4

Example 4 illustrates diaper and pant chassis that may utilize many of the same raw materials, specifications, machines, processes, and supply chains. It is expected that the same quality control measures can be used for them.

Diapers 7 and 8 are placed in different packages and each of the packages are displayed at a common retailer (e.g., Walmart). Diapers 7 and 8 have substantially identical flaps.

Diaper 7:
Form: Taped diaper
Size: 4
Brand: Pampers
Tradename: Baby Dry
Manufacturer: The Procter & Gamble Company
Site of assembly: Plant X
Line type: A
Chassis: Same specifications detailed in Diaper 3 from the Chassis Example section (above).
Flap Materials and Dimensions: Table Below:

|  | Material | Basis Weight (gsm) | Transverse distance (mm) | Longitudinal distance (mm) | dtex |
|---|---|---|---|---|---|
| Front Belt Outer Layer (Nonwoven) | Polyolefin | 10 | 375 | 180 |  |
| Front Belt Inner Layer (Nonwoven) | Polyolefin | 10 | 375 | 140 |  |
| Front Belt Elastics | Spundex |  | 250 (prestretched 100%~200%) |  | 540 |
| Back Belt Outer Layer (Nonwoven) | Polyolefin | 10 | 375 | 220 |  |
| Back Belt Inner Layer (Nonwoven) | Polyolefin | 10 | 375 | 170 |  |
| Back Belt Elastics | Spundex |  | 250 (prestretched 100%~200%) |  | 640 |
| Fastening tab | Polyolefin | 80 | 45 per each element | 30 per each element |  |
| Hook | Polyolefin | 60 | 13 per each element | 30 per each element |  |

Diaper 8:
Form: Pant diaper
Size: 4
Brand: Pampers
Tradename: Easy Ups
Manufacturer: The Procter & Gamble Company
Site of assembly: Plant X
Line type: A
Chassis: Same specifications detailed in Diaper 4 from the Chassis Example section (above).
Flap Materials and Dimensions: Table Immediately Below

|  | Material | Basis Weight (gsm) | Transverse distance (mm) | Longitudinal distance (mm) | dtex |
|---|---|---|---|---|---|
| Front Belt Outer Layer (Nonwoven) | Polyolefin | 10 | 375 | 180 |  |
| Front Belt Inner Layer (Nonwoven) | Polyolefin | 10 | 375 | 140 |  |
| Front Belt Elastics | Spundex |  | 375 (prestretched 100%~270%) |  | 540 |
| Back Belt Outer Layer (Nonwoven) | Polyolefin | 10 | 375 | 220 |  |
| Back Belt Inner Layer (Nonwoven) | Polyolefin | 10 | 375 | 170 |  |
| Back Belt Elastics | Spundex |  | 375 (prestretched 100%~270%) |  | 540 |

Example 5

Example 5 illustrates diaper and pant chassis that may utilize many of the same raw materials, specifications, machines, processes, and supply chains. It is expected that the same quality control measures can be used for them.

Diapers 9 and 10 are placed in different packages and each of the packages are displayed at a common retailer (e.g., Walmart). Diapers 9 and 10 have substantially identical flaps.

Diaper 9:
Form: Taped diaper
Size: 4
Brand: Pampers
Tradename: Baby Dry
Manufacturer: The Procter & Gamble Company
Site of assembly: Plant X
Line type: A
Chassis: Same specifications detailed in Diaper 5 from the Chassis Example section (above).
Flap Materials and Dimensions: Table Below:

|  | Material | Basis Weight (gsm) | Transverse distance (mm) | Longitudinal distance (mm) | dtex |
|---|---|---|---|---|---|
| Front Belt Outer Layer (Nonwoven) | Polyolefin | 10 | 375 | 180 |  |
| Front Belt Inner Layer (Nonwoven) | Polyolefin | 10 | 375 | 140 |  |
| Back Belt Outer Layer (Nonwoven) | Polyolefin | 10 | 375 | 220 |  |
| Back Belt Inner Layer (Nonwoven) | Polyolefin | 10 | 375 | 170 |  |
| Back Belt Elastics | Spundex |  | 180 (prestretched 100%~150%) |  | 1100 |
| Fastening tab | Polyolefin | 80 | 45 per each element | 30 per each element |  |
| Hook | Polyolefin | 60 | 13 per each element | 30 per each element |  |

Diaper 10:
Form: Pant diaper
Size: 4
Brand: Pampers
Tradename: Easy Ups
Manufacturer: The Procter & Gamble Company
Site of assembly: Plant X
Line type: A
Chassis: Same specifications detailed in Diaper 6 from the Chassis Example section (above).

Flap Materials and Dimensions: Table Immediately Below

| | Material | Basis Weight (gsm) | Transverse distance (mm) | Longitudinal distance (mm) | dtex |
|---|---|---|---|---|---|
| Front Belt Outer Layer (Nonwoven) | Polyolefin | 10 | 375 | 180 | |
| Front Belt Inner Layer (Nonwoven) | Polyolefin | 10 | 375 | 140 | |
| Front Belt Elastics | Spundex | | 375 (prestretched 100%~270%) | | 540 |
| Back Belt Outer Layer (Nonwoven) | Polyolefin | 10 | 375 | 220 | |
| Back Belt Inner Layer (Nonwoven) | Polyolefin | 10 | 375 | 170 | |
| Back Belt Elastics | Spundex | | 375 (prestretched 100%~270%) | | 540 |

Example 6

Example 6 illustrates diaper and pant chassis that may utilize many of the same raw materials, specifications, machines, processes, and supply chains. It is expected that the same quality control measures can be used for them.

Diapers 11 and 12 are placed in different packages and each of the packages are displayed at a common retailer (e.g., Walmart). Diapers 11 and 12 have substantially identical flaps.

Diaper 11:
Form: Taped diaper
Size: 4
Brand: Pampers
Tradename: Baby Dry
Manufacturer: The Procter & Gamble Company
Site of assembly: Plant X
Line type: A
Chassis: Same specifications detailed in Diaper 7 from the Chassis Example section (above).
Flap Materials and Dimensions: Table Below:

| | Material | Basis Weight (gsm) | Transverse distance (mm) | Longitudinal distance (mm) | dtex | Hook Location |
|---|---|---|---|---|---|---|
| Front Belt Outer Layer (Nonwoven) | Polyolefin | 10 | 375 | 180 | | |
| Front Belt Inner Layer (Nonwoven) | Polyolefin | 10 | 375 | 140 | | |
| Front Belt Elastics | Spundex | | 375 (prestretched 100%~200%) | | 540 | |
| Back Belt Outer Layer (Nonwoven) | Polyolefin | 10 | 375 | 220 | | |
| Back Belt Inner Layer (Nonwoven) | Polyolefin | 10 | 375 | 170 | | |
| Back Belt Elastics | Spundex | | 375 (prestretched 100%~200%) | | 540 | |
| Hook | Polyolefin | 60 | 13 per each element | 150 per each element | | Inboard lateral distal belt edge |

Diaper 12:
Form: Pant diaper
Size: 4
Brand: Pampers
Tradename: Easy Ups
Manufacturer: The Procter & Gamble Company
Site of assembly: Plant Y
Line type: A
Chassis: Same specifications detailed in Diaper 6 from the Chassis Example section (above).
Flap Materials and Dimensions: Table Immediately Below

| | Material | Basis Weight (gsm) | Transverse distance (mm) | Longitudinal distance (mm) | dtex | Hook Location |
|---|---|---|---|---|---|---|
| Front Belt Outer Layer (Nonwoven) | Polyolefin | 10 | 375 | 180 | | |

| | Material | Basis Weight (gsm) | Transverse distance (mm) | Longitudinal distance (mm) | dtex | Hook Location |
|---|---|---|---|---|---|---|
| Front Belt Inner Layer (Nonwoven) | Polyolefin | 10 | 375 | 140 | | |
| Front Belt Elastics | Spundex | | 375 (prestretched 100%~200%) | | 540 | |
| Back Belt Outer Layer (Nonwoven) | Polyolefin | 10 | 375 | 220 | | |
| Back Belt Inner Layer (Nonwoven) | Polyolefin | 10 | 375 | 170 | | |
| Back Belt Elastics | Spundex | | 375 (prestretched 100%~200%) | | 540 | |
| Hook | Polyolefin | 60 | 13 per each element | 150 per each element | | Inboard lateral distal belt edge |

Example 7

Example 7 illustrates diaper and pant chassis that may utilize many of the same raw materials, specifications, machines, processes, and supply chains. It is expected that the same quality control measures can be used for them.

Diapers 13 and 14 are placed in different packages and each of the packages are displayed at a common retailer (e.g., Walmart). Diapers 13 and 14 have substantially identical flaps.

Diaper 13:
Form: Taped diaper
Size: 4
Brand: Pampers
Tradename: Baby Dry
Manufacturer: The Procter & Gamble Company
Site of assembly: Plant X
Line type: A
Chassis: Same specifications detailed in Diaper 1 from the Chassis Example section (above).
Flap Materials and Dimensions: Table Below:

| | Material | Basis Weight (gsm) | Transverse distance (mm) | Longitudinal distance (mm) | dtex | Hook location |
|---|---|---|---|---|---|---|
| Front Belt Outer Layer (Nonwoven) | Polyolefin | 10 | 375 | 180 | | |
| Front Belt Inner Layer (Nonwoven) | Polyolefin | 10 | 375 | 140 | | |
| Front Belt Elastics | Spundex | | 375 (prestretched 100%~200%) | | 540 | |
| Back Belt Outer Layer (Nonwoven) | Polyolefin | 10 | 375 | 220 | | |
| Back Belt Inner Layer (Nonwoven) | Polyolefin | 10 | 375 | 170 | | |
| Back Belt Elastics | Spundex | | 375 (prestretched 100%~200%) | | 540 | |
| Fastening tab | Polyolefin | 80 | 45 per each element | 30 per each element | | |
| Hook | Polyolefin | 60 | 13 per each element | 30 per each element | | Outboard lateral distal belt edge |

Diaper 14:
Form: Pant diaper
Size: 4
Brand: Pampers
Tradename: Easy Ups
Manufacturer: The Procter & Gamble Company
Site of assembly: Plant Y
Line type: A
Chassis: Same specifications detailed in Diaper 2 from the Chassis Example section (above).
Flap Materials and Dimensions: Table Immediately Below

| | Material | Basis Weight (gsm) | Transverse distance (mm) | Longitudinal distance (mm) | dtex | Hook Location |
|---|---|---|---|---|---|---|
| Front Belt Outer Layer (Nonwoven) | Polyolefin | 10 | 375 | 180 | | |

-continued

| | Material | Basis Weight (gsm) | Transverse distance (mm) | Longitudinal distance (mm) | dtex | Hook Location |
|---|---|---|---|---|---|---|
| Front Belt Inner Layer (Nonwoven) | Polyolefin | 10 | 375 | 140 | | |
| Front Belt Elastics | Spundex | | 375 (prestretched 100%~200%) | | 540 | |
| Back Belt Outer Layer (Nonwoven) | Polyolefin | 10 | 375 | 220 | | |
| Back Belt Inner Layer (Nonwoven) | Polyolefin | 10 | 375 | 170 | | |
| Back Belt Elastics | Spundex | | 375 (prestretched 100%~200%) | | 540 | |
| Hook | Polyolefin | 60 | 13 per each element | 150 per each element | | Inboard lateral distal belt edge |

Example 8

Example 8 illustrates diaper and pant chassis that may utilize many of the same raw materials, specifications, machines, processes, and supply chains. It is expected that the same quality control measures can be used for them.

Diapers 15 and 16 are placed in different packages and each of the packages are displayed at a common retailer (e.g., Walmart). Diapers 15 and 16 have substantially identical flaps.

Diaper 15:
Form: Taped diaper
Size: 4
Brand: Pampers
Tradename: Baby Dry
Manufacturer: The Procter & Gamble Company
Site of assembly: Plant X
Line type: A
Chassis: Same specifications detailed in Diaper 3 from the Chassis Example section (above).
Flap Materials and Dimensions: Table Below:

| | Material | Basis Weight (gsm) | Transverse distance (mm) | Longitudinal distance (mm) | dtex | Hook location |
|---|---|---|---|---|---|---|
| Front Belt Outer Layer (Nonwoven) | Polyolefin | 10 | 375 | 180 | | |
| Front Belt Inner Layer (Nonwoven) | Polyolefin | 10 | 375 | 140 | | |
| Front Belt Elastics | Spundex | | 375 (prestretched 100%~200%) | | 540 | |
| Back Belt Outer Layer (Nonwoven) | Polyolefin | 10 | 375 | 220 | | |
| Back Belt Inner Layer (Nonwoven) | Polyolefin | 10 | 375 | 170 | | |
| Back Belt Elastics | Spundex | | 375 (prestretched 100%~200%) | | 540 | |
| Fastening tab | Polyolefin | 80 | 60 per each element | 140 per each element | | |
| Hook | Polyolefin | 60 | 30 per each element | 13 per each element | | Outboard lateral distal belt edge |

Diaper 16:
Form: Pant diaper
Size: 4
Brand: Pampers
Tradename: Easy Ups
Manufacturer: The Procter & Gamble Company
Site of assembly: Plant X
Line type: A
Chassis: Same specifications detailed in Diaper 4 from the Chassis Example section (above).
Flap Materials and Dimensions: Table Immediately Below

| | Material | Basis Weight (gsm) | Transverse distance (mm) | Longitudinal distance (mm) | dtex |
|---|---|---|---|---|---|
| Front Belt Outer Layer (Nonwoven) | Polyolefin | 10 | 375 | 180 | |

| Material | Basis Weight (gsm) | Transverse distance (mm) | Longitudinal distance (mm) | dtex |
|---|---|---|---|---|
| Front Belt Inner Layer (Nonwoven) | Polyolefin | 10 | 375 | 140 | |
| Front Belt Elastics | Spundex | | 375 (prestretched 100%~270%) | | 540 |
| Back Belt Outer Layer (Nonwoven) | Polyolefin | 10 | 375 | 220 | |
| Back Belt Inner Layer (Nonwoven) | Polyolefin | 10 | 375 | 170 | |
| Back Belt Elastics | Spundex | | 375 (prestretched 100%~270%) | | 540 |

All dimensions in the above flap examples are measured in fully stretched conditions in the lateral direction and the transverse direction, either on a finished product or on raw materials. One or more flaps of pant articles may be cut or separated from the chassis so that the measurements of the dimensions can be done in a flat condition. Flap length is defined at the lateral distance between lateral distal edges of the flap. Flap width is defined as the longitudinal distance between longitudinal distal edges of the flap. In cases where the flap is shaped the maximum width and/or length should be used. Measurements should be taken using a Using a ruler calibrated against a certified NIST ruler and accurate to 0.5 mm. Measurements should be recorded to the nearest 0.1 mm. The dimensions of the pant article and the taped article should be done under same conditions (e.g., ambient temperature for both, the same measurement apparatus for both) and in the same manner for consistent results. Product specifications, product drawings, and equipment drawings may be substituted for measuring actual products.

Elastic decitex (Dtex) is obtained from suppliers' specification.

Material basis weight is measured in accordance with ASTM D 756, ISO 536 or ERT-40.3-90.

Test Methods

Opacity Method

Opacity is measured using a 0° illumination/45° detection, circumferential optical geometry, spectrophotometer with a computer interface such as the HunterLab LabScan XE running Universal Software (available from Hunter Associates Laboratory Inc., Reston, Va.) or equivalent instrument. Instrument calibration and measurements are made using the standard white and black calibration plates provided by the vendor. All testing is performed in a room maintained at 23±2° C. and 50±2% relative humidity.

The spectrophotometer is configured for the XYZ color scale, D65 illuminant, 10° standard observer, with UV filter set to nominal. The instrument is standardized according to the manufacturer's procedures using the 0.7 inch port size and 0.5 inch area view. After calibration, the software is set to the Y opacity procedure which prompts the operator to cover the sample with either the white or black calibration tile during the measurement.

Articles are pre-conditioned at 23° C.±2° C. and 50%±2% relative humidity for two hours prior to testing. To obtain a specimen, the article is stretched flat on a bench, body facing surface upward, and the total longitudinal length of the article is measured. A testing site on the inner and outer cuffs is selected at the longitudinal midpoint of the article. Using scissors, a test specimen is cut 60 mm long by the entire height of the inner cuff centered at the longitudinal midpoint of the left cuff. Next, a second test specimen is cut, this time from the outer cuff, 60 mm long by the entire height of the outer cuff, centered at the longitudinal midpoint of the left outer cuff. In like fashion, inner and outer cuff specimens are prepared from the cuffs on the right side of the article.

The specimen is placed over the measurement port. The specimen should completely cover the port with the surface corresponding to the inner-facing surface of the cuff directed toward the port. The specimen is gently extended until taut in its longitudinal direction so that the cuff lies flat against the port plate. Adhesive tape is applied to secure the cuff to the port plate in its extended state for testing. Tape should not cover any portion of the measurement port. The specimen is then covered with the white standard plate. A reading is taken, then the white tile is removed and replaced with the black standard tile without moving the specimen. A second reading is taken, and the opacity is calculated as follows:

$$\text{Opacity} = (Y \text{ value}_{(black\ backing)}/Y \text{ value}_{(white\ backing)}) \times 100$$

Specimens from five identical articles (10 inner cuff (5 left and 5 right) and 10 outer cuff (5 left and 5 right)) are analyzed and their opacity results recorded. The average opacity for the inner cuffs and the outer cuffs are calculated and report separately, each to the nearest 0.01%.

Water Vapor Transmission Rate Method

Water Vapor Transmission Rate (WVTR) is measured using the wet cup approach. A cylindrical cup is filled with water, maintaining a constant headspace between the water surface and a specimen sealed over the cup's upper opening. The vapor loss is measured gravimetrically after heating the assembled cup for a specified time in an oven. All testing is performed in a room maintained at 23° C.±2° C. and 50%±2% relative humidity.

Articles are preconditioned at 23° C.±2° C. and 50%±2% relative humidity for two hours prior to testing. The article stretched flat on a bench, body facing surface upward, and the total longitudinal length of the article is measured. A testing site on the inner and outer cuffs is selected at the longitudinal midpoint of the article. Using scissors, a test specimen is cut 60 mm long by the entire height of the inner cuff centered at the longitudinal midpoint of the left cuff. Next, a second test specimen is cut, this time from the outer cuff, 60 mm long by the entire height of the outer cuff, centered at the longitudinal midpoint of the left outer cuff. In like fashion, inner and outer cuff specimens from the cuffs on the right side of the article are prepared.

Glass straight walled, cylindrical vials, 95 mm tall with a 17.8 mm internal diameter at the opening are used as WVTR test vials. Each test vial is filled with distilled water accurately to a level 25.0 mm±0.1 mm from the upper lip of the vial's opening. The specimen is placed, inner-facing surface of the cuff downward, over the vial's opening. The specimen is gently pulled taut and secured around the vial's circumference with an elastic band. The specimen is further sealed by wrapping Teflon tape around the vial's circumference. A preferred Teflon tape is a thread sealant tape 0.25" wide available from McMaster Carr (cat. No. 4591K11) or equivalent. The Teflon tape is applied up to the top edge of the vial but should not cover any portion of the vial's opening. The mass of the vial assembly (vial+specimen+ sealing tape) is weighed to the nearest 0.0001 gram. This is the starting mass.

The vial assemblies are placed upright in a mechanical convection oven (e.g. Lindberg/BlueM oven available from ThermoScientific or equivalent) maintained at 38±1° C. for 24 hours, taking care to avoid contact between the water in the vials and the specimens. After 24 hours has elapsed, the vial assemblies are removed from the oven and allowed to come to room temperature. The mass of each vial assembly is measured to the nearest 0.0001 gram. This is the final mass.

The WVTR is calculated using the following equation:

WVTR (g/m²/24 hrs)=([starting mass (g)−final mass (g)]/surface area (m²))/24 hrs Specimens from five identical articles (10 inner cuff (5 left and 5 right) and 10 outer cuff (5 left and 5 right)) are analyzed and their WVTR results recorded. The average WVTR for the inner cuffs and the outer cuffs are each reported separately to the nearest 1 g/m²/24 hrs.

Air Permeability Test

Air permeability is tested using a TexTest FX3300 Air Permeability Tester (available from Advanced Testing Instruments, Greer, S.C.) with a custom made 1 cm² circular aperture (also available from Advanced Testing Instruments) or equivalent instrument. The instrument is calibrated according to the manufacturer's procedures. All testing is performed in a room maintained at 23° C.±2° C. and 50%±2% relative humidity.

The articles are pre-conditioned at 23° C.±2° C. and 50%±2% relative humidity for two hours prior to testing. To obtain a specimen, the article is stretched flat on a bench, body facing surface upward, and the total longitudinal length of the article is measured. A testing site on the inner and outer cuffs is selected at the longitudinal midpoint of the article. Using scissors, a test specimen is cut 60 mm long by the entire height of the inner cuff centered at the longitudinal midpoint of the left cuff. Next, a second test specimen is cut, this time from the outer cuff, 60 mm long by the entire height of the outer cuff, centered at the longitudinal midpoint of the left outer cuff. In like fashion, inner and outer cuff specimens are prepared from the cuffs on the right side of the article.

The specimen is centered over the measurement port. The specimen should completely cover the port with the surface corresponding to the inward-facing surface of the cuff directed toward the port. The specimen is gently extended in its longitudinal direction until taut so that the cuff lies flat across the port. Adhesive tape is applied to secure the cuff across the port in its extended state for testing. Tape should not cover any portion of the measurement port. The test pressure is set to allow air to pass through the specimen. For non-woven cuffs the pressure is typically set for 125 Pa and for cuffs containing films typically 2125 Pa is used. The sample ring is closed and the measuring range is adjusted until the range indicator shows green to indicate that the measurement is within the accepted limits of the instrument. The air permeability is recorded to the nearest 0.1 m³/m²/min.

Hydrostatic Head Test

Hydrostatic head is tested using a TexTest FX3000 Hydrostatic Head Tester (available from Advanced Testing Instruments, Greer, S.C.) with a custom made 1.5 cm² circular measurement port (also available from Advanced Testing Instruments). Two annular sleeve rings, the same dimensions as the gaskets around the measurement ports, are cut from the standard protective sleeves for fine nonwovens (part FX3000-NWH, available from Advanced Testing Instruments). The sleeve rings are then adhered with two-sided adhesive tape to the sample facing surfaces of the upper and lower gaskets of the TexTest instrument to protect the specimen during clamping. Standardize the instrument according to the manufacturer's procedures. All testing is performed in a room maintained at about 23° C.±2° C. and about 50%±2% relative humidity.

Precondition the articles at about 23° C.±2° C. and about 50%±2% relative humidity for two hours prior to testing. To obtain a specimen, lay the article stretched flat on a bench, body facing surface upward, and measure the total longitudinal length of the article. Select a testing site on the inner and outer cuffs, at the longitudinal midpoint of the article. Using scissors cut a test specimen 70 mm long by the entire height of the inner cuff centered at the longitudinal midpoint of the left cuff. Next cut a second test specimen, this time from the outer cuff, 70 mm long by the entire height of the outer cuff, centered at the longitudinal midpoint of the left outer cuff. In like fashion, prepare inner and outer cuff specimens from the cuffs on the right side of the article.

Place the specimen centered over the port of the upper test head. The specimen should completely cover the port with the surface corresponding to the outward-facing surface of the cuff directed toward the port (inner-facing surface will then be facing the water). Gently extend the specimen taut in its longitudinal direction so that the cuff lies flat against the upper test plate. Adhesive tape is applied to secure the cuff to the test plate in its extended state for testing. Tape should not cover any portion of the measurement port.

Fill the TexTest syringe with distilled water, adding the water through the measurement port of the lower test plate. The water level should be filled to the top of the lower gasket. Mount the upper test head onto the instrument and lower the test head to make a seal around the specimen. The test speed is set to 3 mbar/min for samples that have a hydrostatic head of 50 mbar or less and a speed of 60 mbar/min for samples with a hydrostatic head above 50 mbar. Start the test and observe the specimen surface to detect water droplets penetrating the surface. The test is terminated when one drop is detected on the surface of the specimen or the pressure exceeds 200 mbar. Record the pressure to the nearest 0.5 mbar or record as >200 mbar if there was no penetration detected.

A total of five identical articles (10 inner cuff and 10 outer cuff specimens) are analyzed and their hydrostatic head results recorded. Calculate and report the average hydrostatic head for the inner cuffs and the outer cuffs and report each to the nearest 0.1 mbar.

Low Surface Tension Fluid Strikethrough Time Test

The low surface tension fluid strikethrough time test is used to determine the amount of time it takes a specified quantity of a low surface tension fluid, discharged at a prescribed rate, to fully penetrate a sample of a web (and other comparable barrier materials) which is placed on a reference absorbent pad.

For this test, the reference absorbent pad is 5 plies of Ahlstrom grade 989 filter paper (10 cm×10 cm) and the test fluid is a 32 mN/m low surface tension fluid.

This test is designed to characterize the low surface tension fluid strikethrough performance (in seconds) of webs intended to provide a barrier to low surface tension fluids, such as runny BM, for example.

Lister Strikethrough Tester: The instrumentation is like described in EDANA ERT 153.0-02 section 6 with the following exception: the strike-through plate has a star-shaped orifice of 3 slots angled at 60 degrees with the narrow slots having a 10.0 mm length and a 1.2 mm slot width. This equipment is available from Lenzing Instruments (Austria) and from W. Fritz Metzger Corp (USA). The unit needs to be set up such that it does not time out after 100 seconds.

Reference Absorbent Pad: Ahlstrom Grade 989 filter paper, in 10 cm×10 cm areas, is used. The average strikethrough time is 3.3+0.5 seconds for 5 plies of filter paper using the 32 mN/m test fluid and without the web sample. The filter paper may be purchased from Empirical Manufacturing Company, Inc. (EMC) 7616 Reinhold Drive Cincinnati, Ohio 45237.

Test Fluid: The 32 mN/m surface tension fluid is prepared with distilled water and 0.42+/−0.001 g/liter Triton-X 100. All fluids are kept at ambient conditions.

Electrode-Rinsing Liquid: 0.9% sodium chloride (CAS 7647-14-5) aqueous solution (9 g NaCl per 1 L of distilled water) is used.

Test Procedure

All testing is performed in a room maintained at about 23° C.±2° C. and about 50%±2% relative humidity. The Ahlstrom filter paper and test articles are conditioned in this controlled environment for 24 hours and 2 hours before testing.

Ensure that the surface tension is 32 mN/m+/−1 mN/m. Otherwise remake the test fluid.

Prepare the 0.9% NaCl aqueous electrode rinsing liquid.

Ensure that the strikethrough target (3.3+/−0.5 seconds) for the Reference Absorbent Pad is met by testing 5 plies with the 32 mN/m test fluid as follows:

Neatly stack 5 plies of the Reference Absorbent Pad onto the base plate of the strikethrough tester.

Place the strikethrough plate over the 5 plies and ensure that the center of the plate is over the center of the paper. Center this assembly under the dispensing funnel.

Ensure that the upper assembly of the strikethrough tester is lowered to the pre-set stop point.

Ensure that the electrodes are connected to the timer.

Turn the strikethrough tester "on" and zero the timer.

Using the 5 mL fixed volume pipette and tip, dispense 5 mL of the 32 mN/m test fluid into the funnel.

Open the magnetic valve of the funnel (by depressing a button on the unit, for example) to discharge the 5 mL of test fluid. The initial flow of the fluid will complete the electrical circuit and start the timer. The timer will stop when the fluid has penetrated into the Reference Absorbent Pad and fallen below the level of the electrodes in the strikethrough plate.

Record the time indicated on the electronic timer.

Remove the test assembly and discard the used Reference Absorbent Pad. Rinse the electrodes with the 0.9% NaCl aqueous solution to "prime" them for the next test. Dry the depression above the electrodes and the back of the strikethrough plate, as well as wipe off the dispenser exit orifice and the bottom plate or table surface upon which the filter paper is laid.

Repeat this test procedure for a minimum of 3 replicates to ensure the strikethrough target of the Reference Absorbent Pad is met. If the target is not met, the Reference Absorbent Pad may be out of spec and should not be used.

After the Reference Absorbent Pad performance has been verified, nonwoven web samples may be tested.

Precondition the test articles at about 23° C.±2° C. and about 50%±2% relative humidity for two hours prior to testing. To obtain a specimen, lay the article stretched flat on a bench, body facing surface upward, and measure the total longitudinal length of the article. Select a testing site on the inner and outer cuffs, at the longitudinal midpoint of the article. Using scissors cut a test specimen 70 mm long by the entire height of the inner cuff centered at the longitudinal midpoint of the left cuff. Next cut a second test specimen, this time from the outer cuff, 70 mm long by the entire height of the outer cuff, centered at the longitudinal midpoint of the left outer cuff. In like fashion, prepare inner and outer cuff specimens from the cuffs on the right side of the article.

Place the specimen centered over the port of the strike through plate. The specimen should completely cover the port with the surface corresponding to the body-facing surface of the cuff directed toward the port. Gently extend the specimen taut in its longitudinal direction so that the cuff lies flat against the upper test plate. Adhesive tape is applied to secure the cuff to the test plate in its extended state for testing. Tape should not cover any portion of the measurement port.

Ensure that the upper assembly of the strikethrough tester is lowered to the pre-set stop point.

Ensure that the electrodes are connected to the timer. Turn the strikethrough tester "on" and zero the timer.

Run as described above.

Repeat this procedure for three articles. Average the six values and report as the 32 mN/m low surface tension strikethrough time to the nearest 0.1 seconds.

All documents cited in the Detailed Description of the Invention are, in relevant part, incorporated herein by reference; the citation of any document is not to be construed as an admission that it is prior art with respect to the present invention. To the extent that any definition or meaning of a term in this written document conflicts with any definition or meaning of the term in a document incorporated by reference, the definition or meaning assigned to the term in this document shall govern.

While particular embodiments of the present invention have been illustrated and described, it would be obvious to those skilled in the art that various other changes and modifications can be made without departing from the spirit and scope of the invention. It should be apparent that combinations of such embodiments and features are possible and can result in executions within the scope of this invention. It is therefore intended to cover in the appended claims all such changes and modifications that are within the scope of this invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An array of taped and pant articles comprising:
a first package comprising a taped article comprising a first chassis and a first belt flap, the first belt flap comprising a first and a second nonwoven and a first elastic layer disposed therebetween, and the taped article comprising a first chassis;
wherein at least a portion of the first elastic layer extends continuously from a first side edge of the first belt flap to a second, laterally opposed, sided edge of the first belt flap;
wherein the first belt flap is joined to the first chassis by a first flap adhesive, and wherein the first belt flap extends continuously in a transverse direction across the first chassis;
wherein the second nonwoven is wearer-facing;
a second package comprising a pant article comprising a second chassis and a second belt flap, the second belt flap comprising a third and a fourth nonwoven and a second elastic layer disposed therebetween, and the pant article comprising a second chassis;
wherein at least a portion of the second elastic layer extends continuously from a first side edge of the second belt flap to a second, laterally opposed, sided edge of the second belt flap;
wherein the second belt flap is joined to the second chassis by a second flap adhesive; and wherein the second belt flap extends continuously in a transverse direction across the second chassis;
wherein the fourth nonwoven is wearer-facing;
wherein:
  each of the first and second chassis comprise the same dimensions of one or more of: core width at the lateral centerline, core width at one of the front or rear core end, a distance from a left outer cuff distal edge to a right outer cuff distal edge, a distance from a left inner cuff distal edge to a left outer cuff distal edge, a distance from a left inner cuff proximal edge to a right inner cuff proximal edge, a distance from a left inner cuff proximal edge to a left outer cuff distal edge, a free height of the inner cuff, inner cuff hem fold width, inner cuff elastics length, outer cuff elastics length, core length, and backsheet width;
  each of the first and second chassis comprise identical chemical compositions of one or more of a topsheet, backsheet film, backsheet nonwoven, core super absorbent polymers, core pulp, core nonwoven, core tissue, leg cuff film, leg cuff nonwoven, super absorbent polymer adhesive, core nonwoven adhesive, leg cuff elastic adhesive, and backsheet nonwoven/film adhesive;
  each of the first and second chassis comprise the same basis weight of one or more of the topsheet, backsheet film, backsheet nonwoven, core super absorbent polymers, core pulp, leg cuff nonwoven, leg cuff film, super absorbent polymer adhesive, leg cuff adhesive, and backsheet nonwoven/film adhesive;
wherein each of the first and second belt flaps comprise one or more of the following:
  each of the first and second belt flaps comprise a same longitudinal distance m;
  each of the first and second belt flaps comprise a same transverse distance n;
  each of the first and second belt flaps comprise a same longitudinal distance, o, between an end edge of the first chassis and an end edge of the first belt flap and an end edge of the second chassis and an end edge of the second belt flap;
  each of the first and second belt flaps comprise a same longitudinal distance, p, between the end edge of the first chassis and a proximal edge of the first belt flap and the end edge of the second chassis and a proximal edge of the second belt flap;
  each of the first and second belt flaps comprise a same longitudinal distance, q, between an end edge of a first flap-to-chassis adhesive pattern and the end edge of the first belt flap and the end edge of the second chassis and an end edges of the second belt flap;
  each of the first and second belt flaps comprise a same transverse distance, r, between the end edge of a first flap-to-chassis adhesive pattern and the end edge of the first belt flap and the end edge of the second chassis and the end edges of the second belt flap;
  each of the first and second belt flaps comprise identical chemical compositions of the first and third nonwovens;
  each of the first and second belt flaps comprise identical chemical compositions of the second and fourth nonwovens;
  each of the first and second belt flaps comprise identical chemical compositions of the first and second adhesives;
  each of the first and second belt flaps have the same basis weights of the first and third nonwovens;
  each of the first and second belt flaps have the same basis weights of the second and fourth nonwovens;
  each of the first and second belt flaps have the same basis weights of the first and second adhesives;
wherein the taped article is not pre-closed and wherein the pant article is pre-closed to form a waist opening and leg openings;
wherein the taped and pant articles are manufactured by the same manufacturer; and
wherein the first package comprises a first weight range of a prospective wearer, and wherein said second package comprises a second weight range of a prospective wearer, wherein said first and second weight ranges overlap, at least in part.

2. The array of taped and pant articles of claim 1, wherein each of the first and second belt flaps comprise two or more of the following:
  each of the first and second belt flaps comprise a same longitudinal distance m;
  each of the first and second belt flaps comprise a same transverse distance n;
  each of the first and second belt flaps comprise a same longitudinal distance, o, between an end edge of the first chassis and an end edge of the first belt flap and an end edge of the second chassis and an end edge of the second belt flap;

each of the first and second belt flaps comprise a same longitudinal distance, p, between the end edge of the first chassis and a proximal edge of the first belt flap and the end edge of the second chassis and a proximal edge of the second belt flap;

each of the first and second belt flaps comprise a same longitudinal distance, q, between an end edge of a first flap-to-chassis adhesive pattern and the end edge of the first belt flap and the end edge of the second chassis and an end edges of the second belt flap;

each of the first and second belt flaps comprise a same transverse distance, r, between the end edge of a first flap-to-chassis adhesive pattern and the end edge of the first belt flap and the end edge of the second chassis and the end edges of the second belt flap;

each of the first and second belt flaps comprise identical chemical compositions of the first and third nonwovens;

each of the first and second belt flaps comprise identical chemical compositions of the second and fourth nonwovens;

each of the first and second belt flaps comprise identical chemical compositions of the first and second adhesives;

each of the first and second belt flaps have the same basis weights of the first and third nonwovens;

each of the first and second belt flaps have the same basis weights of the second and fourth nonwovens; and each of the first and second belt flaps have the same basis weights of the first and second adhesives.

3. The array of taped and pant articles of claim 2, wherein each of the first and second chassis comprise the same dimensions of two or more of: core width at the lateral centerline, core width at one of the front or rear core end, a distance from a left outer cuff distal edge to a right outer cuff distal edge, a distance from a left inner cuff distal edge to a left outer cuff distal edge, a distance from a left inner cuff proximal edge to a right inner cuff proximal edge, a distance from a left inner cuff proximal edge to a left outer cuff distal edge, a free height of the inner cuff, inner cuff hem fold width, inner cuff elastics length, outer cuff elastics length, core length, and backsheet width.

4. The array of taped and pant articles of claim 3, wherein each of the first and second chassis comprise the same dimensions of three or more of: core width at the lateral centerline, core width at one of the front or rear core end, a distance from a left outer cuff distal edge to a right outer cuff distal edge, a distance from a left inner cuff distal edge to a left outer cuff distal edge, a distance from a left inner cuff proximal edge to a right inner cuff proximal edge, a distance from a left inner cuff proximal edge to a left outer cuff distal edge, a free height of the inner cuff, inner cuff hem fold width, inner cuff elastics length, outer cuff elastics length, core length, and backsheet width.

5. The array of taped and pant articles of claim 4, wherein the first belt flap is joined to the back waist region of the first chassis and wherein the second belt flap is joined to the back waist region of the second chassis, and wherein the first belt flap is joined to a garment-facing surface of the first chassis and wherein the second belt flap is joined to a garment-facing surface of the second chassis.

6. The array of taped and pant articles of claim 5, wherein the first belt flap is joined to a portion of a backsheet film of the first chassis and a portion of a backsheet nonwoven of the first chassis, and wherein the second belt flap is joined to a portion of a backsheet film of the second chassis and a portion of a backsheet nonwoven of the second chassis.

7. The array of taped and pant articles of claim 4, wherein the first and/or second elastic layers comprise elastic strands.

8. The array of taped and pant articles of claim 4, wherein the first and/or second elastic layers comprise elastic film, and wherein the elastic film is apertured.

9. The array of taped and pant articles of claim 4, wherein the first belt flap comprises first fasteners that extend beyond side edges of the first belt, wherein the first fasteners are folded.

10. The array of taped and pant articles of claim 9, wherein the second belt flap comprises second fasteners that are refastenably engaged to form waist and leg openings.

11. The array of taped and pant articles of claim 4, wherein side edges of the second belt flap are permanently joined to side edges of the third belt flap to form waist and leg openings.

12. The array of taped and pant articles of claim 4, wherein the core super absorbent polymers of the first and second chassis are compositionally identical.

13. The array of taped and pant articles of claim 4, wherein the first and second chassis have identical component cross sectional order and disposition in at least one of the front waist region, back waist region, and crotch region.

14. The array of taped and pant articles of claim 13, wherein inner leg cuffs of the first and second chassis are composed of the compositionally identical materials.

15. The array of taped and pant articles of claim 3, wherein a third belt flap is joined to a front waist region of the second chassis, and wherein the third belt flap is joined to a garment-facing surface of the second chassis.

16. The array of taped and pant articles of claim 15, wherein the third belt flap is joined to a portion of a backsheet film of the second chassis and a portion of a backsheet nonwoven of the second chassis.

17. The array of taped and pant articles of claim 3, wherein each of the taped and pant articles comprise a first and second wetness indicator, respectively, and wherein the first and second wetness indicators are compositionally identical.

18. The array of taped and pant articles of claim 3, wherein the inner leg cuffs of the first and second chassis have identical component cross sectional order and disposition in at least one of the front waist region, back waist region, and crotch region.

19. The array of taped and pant articles of claim 1, wherein each of the first and second belt flaps comprise three or more of the following:

each of the first and second belt flaps comprise a same longitudinal distance m;

each of the first and second belt flaps comprise a same transverse distance n;

each of the first and second belt flaps comprise a same longitudinal distance, o, between an end edge of the first chassis and an end edge of the first belt flap and an end edge of the second chassis and an end edge of the second belt flap;

each of the first and second belt flaps comprise a same longitudinal distance, p, between the end edge of the first chassis and a proximal edge of the first belt flap and the end edge of the second chassis and a proximal edge of the second belt flap;

each of the first and second belt flaps comprise a same longitudinal distance, q, between an end edge of a first flap-to-chassis adhesive pattern and the end edge of the first belt flap and the end edge of the second chassis and an end edges of the second belt flap;

each of the first and second belt flaps comprise a same transverse distance, r, between the end edge of a first flap-to-chassis adhesive pattern and the end edge of the first belt flap and the end edge of the second chassis and the end edges of the second belt flap;

each of the first and second belt flaps comprise identical chemical compositions of the first and third nonwovens;

each of the first and second belt flaps comprise identical chemical compositions of the second and fourth nonwovens;

each of the first and second belt flaps comprise identical chemical compositions of the first and second adhesives;

each of the first and second belt flaps have the same basis weights of the first and third nonwovens;

each of the first and second belt flaps have the same basis weights of the second and fourth nonwovens; and each of the first and second belt flaps have the same basis weights of the first and second adhesives.

20. The array of taped and pant articles of claim 1, wherein the first belt flap of the taped article comprises a greater transverse distance n than the second belt flap of the pant article, and wherein the second belt flap of the pant article comprises a greater longitudinal distance m than the first belt flap of the taped article, and wherein the longitudinal distance m is measured adjacent to side edges of first and second belt flaps.

* * * * *